(12) United States Patent
Etemad et al.

(10) Patent No.: US 10,327,670 B2
(45) Date of Patent: Jun. 25, 2019

(54) SYSTEMS, METHODS AND DEVICES FOR EXERCISE AND ACTIVITY METRIC COMPUTATION

(71) Applicant: GestureLogic Inc., Ottawa (CA)

(72) Inventors: Seyed Ali Etemad, Ottawa (CA); Roshanak Houmanfar, Ottawa (CA); Mark Klibanov, Ottawa (CA); Leonard MacEachern, Ottawa (CA); Kaveh Firouzi, Ottawa (CA)

(73) Assignee: GestureLogic Inc., Ottawa (CA)

( * ) Notice: Subject to any disclaimer, the term of this patent is extended or adjusted under 35 U.S.C. 154(b) by 0 days.

(21) Appl. No.: 14/669,726

(22) Filed: Mar. 26, 2015

(65) Prior Publication Data

US 2015/0272483 A1 Oct. 1, 2015

Related U.S. Application Data

(60) Provisional application No. 61/970,454, filed on Mar. 26, 2014, provisional application No. 61/970,482, filed on Mar. 26, 2014.

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/0488* (2013.01); *A61B 5/05* (2013.01);
(Continued)

(58) Field of Classification Search
CPC ............... G06F 19/3418; Y10S 128/92; Y10S 128/925; G08B 21/0453; A61B 5/7264; A61B 5/0488; A61B 5/1123; A61B 5/11; A61B 5/486; A61B 5/681; A61B 5/0024; A61B 5/04; A61B 5/1124; A61B 5/6804;
(Continued)

(56) References Cited

U.S. PATENT DOCUMENTS 8,909,332 B2 12/2014 Vitali et al.
9,510,789 B2 * 12/2016 Houmanfar .......... A61B 5/7267
(Continued)

FOREIGN PATENT DOCUMENTS

CA 2818020 A1 12/2012
EP 2698099 A1 2/2014
(Continued)

OTHER PUBLICATIONS

Chen, Xiang, et al. "Hand gesture recognition research based on surface EMG sensors and 2D-accelerometers." Wearable Computers, 2007 11th IEEE International Symposium on. IEEE, 2007.*
(Continued)

*Primary Examiner* — David J. McCrosky
(74) *Attorney, Agent, or Firm* — Bereskin & Parr LLP/S.E.N.C.R.L., s.r.l.

(57) ABSTRACT

Systems, methods and devices that facilitate determination of enhanced exercise or physical activity metrics by considering multiple types of data. Metrics are computable by pre-processing, and in some cases segmenting, a variety of input signals, such as acceleration signals, electromyography signals or other signals from a wearable device.

16 Claims, 27 Drawing Sheets

(51) Int. Cl.
| | |
|---|---|
| A61B 5/0488 | (2006.01) |
| A61B 5/05 | (2006.01) |
| H04B 1/3827 | (2015.01) |
| A61B 5/053 | (2006.01) |
| H04B 1/3888 | (2015.01) |
| A61B 5/04 | (2006.01) |
| A61B 5/22 | (2006.01) |
| A61B 5/0205 | (2006.01) |

(52) U.S. Cl.
CPC .......... *A61B 5/0531* (2013.01); *A61B 5/6801* (2013.01); *A61B 5/7225* (2013.01); *A61B 5/7267* (2013.01); *H04B 1/385* (2013.01); *H04B 1/3888* (2013.01); *A61B 5/0022* (2013.01); *A61B 5/0024* (2013.01); *A61B 5/02055* (2013.01); *A61B 5/04012* (2013.01); *A61B 5/1123* (2013.01); *A61B 5/22* (2013.01); *A61B 5/4875* (2013.01); *A61B 5/6831* (2013.01); *A61B 5/7203* (2013.01); *A61B 5/7275* (2013.01); *H04B 2001/3855* (2013.01)

(58) Field of Classification Search
CPC ... A61B 5/6824; A61B 5/6825; A61B 5/7267; A63B 2220/80; A63B 2220/836
See application file for complete search history.

(56) References Cited

U.S. PATENT DOCUMENTS

| | | | |
|---|---|---|---|
| 2005/0113703 A1 | 5/2005 | Farringdon et al. | |
| 2005/0177059 A1 | 8/2005 | Koivumaa et al. | |
| 2011/0301441 A1 | 12/2011 | Bandic et al. | |
| 2012/0071743 A1 | 3/2012 | Todorov et al. | |
| 2012/0271121 A1 | 10/2012 | Della Torre et al. | |
| 2014/0278229 A1 | 9/2014 | Hong et al. | |
| 2014/0288435 A1 | 9/2014 | Richards et al. | |
| 2015/0133823 A1* | 5/2015 | Houmanfar | A61B 5/1122 600/595 |
| 2015/0272457 A1 | 10/2015 | Etemad et al. | |
| 2015/0272482 A1 | 10/2015 | Houmanfar et al. | |
| 2015/0272501 A1 | 10/2015 | MacEachern et al. | |
| 2016/0206921 A1 | 7/2016 | Szabados et al. | |
| 2016/0213323 A1 | 7/2016 | Proud | |

FOREIGN PATENT DOCUMENTS

| | | |
|---|---|---|
| WO | 2006053290 A2 | 5/2006 |
| WO | 2009152608 A1 | 12/2009 |

OTHER PUBLICATIONS

Shin, et al. (Dec. 2013). Developing a device using accelerometers and EMG for hand movement recognition. In Biomedical Engineering and Informatics (BMEI), 2013 6th International Conference on (pp. 398-402). IEEE.*

Georgakis, et al. "Fatigue analysis of the surface EMG signal in isometric constant force contractions using the averaged instantaneous frequency." IEEE Transactions on Biomedical Engineering 50.2 (2003): 262-265.*

Pogorelc, e al. "Home-based health monitoring of the elderly through gait recognition." Journal of Ambient Intelligence and Smart Environments 4.5 (2012): Abstract.*

Chen, Ruizhi, et al. "Sensing strides using EMG signal for pedestrian navigation." GPS solutions 15.2 (2011): 161-170.*

Document relating to PCT Application No. PCT/CA2016/050348, dated Jun. 30, 2016 (International Search Report and Written Opinion).

Duda et al., Pattern Classification (2nd Edition), Wiley-Interscience, 2000.

Gelman, "Analysis of Variance—Why It Is More Important Than Ever", Annals of Statistics, vol. 33 (1), pp. 1-53, 2005.

Kulić et al., "Incremental Learning of Full Body Motion Primitives and Their Sequencing Through Human Motion Observation", The International Journal of Robotics Research. SAGE Publications, 0278364911426178, 2011.

Rabiner, "A Tutorial on Hidden Markov Models and Selected Applications in Speech Recognition", Proceedings of the IEEE, vol. 77 (2), pp. 257-286, 1989.

Smith, A Tutorial on Principal Components Analysis, 2002.

Wang, "Recent Developments in Human Motion Analysis." Pattern Recognition, vol. 36 (3), pp. 585-601, Elsevier, 2003.

Lin et al., "Full-Body Multi-Primitive Segmentation Using Classifiers", Humanoid Robotics, Proceedings of the 14th RAS International Conference, IEEE, pp. 874-880, 2014.

Document relating to PCT Application No. PCT/CA2016/050345, dated Jul. 18, 2016 (International Search Report & Written Opinion).

Document relating to PCT Application No. PCT/CA2016/050346, dated Jul. 19, 2016 (International Search Report & Written Opinion).

Document relating to PCT Application No. PCT/CA2016/050347, dated Jun. 8, 2016 (International Search Report & Written Opinion).

Lin, Chia-Hua, "A Real-Time Human Posture Classifier and Fall-Detector," Electronic Thesis or Dissertation, Case Western Reserve University, Aug. 2014, OhioLINK Electronic Theses and Dissertations Center, pp. 1-30 (*pp. 7-8, 6, 12-13, 19-21, 26-26, 32, 49, 66).

Quwaider, Muhannad and Subir Biswas, "Body posture identification using hidden Markov model with a wearable sensor network," BODYNETS (2008).

Document relating to U.S. Appl. No. 14/669,781, dated May 11, 2016 (Office Action).

Document relating to U.S. Appl. No. 14/669,781, dated Dec. 16, 2016 (Final Office Action).

Document relating to U.S. Appl. No. 14/669,635, dated Aug. 9, 2016 (Office Action).

Document relating to U.S. Appl. No. 14/669,689, dated Mar. 6, 2017 (Office Action).

Document relating to U.S. Appl. No. 14/669,689, dated Jul. 21, 2017(Final Office Action).

Altun et al., "Comparative study on classifying human activities with miniature inertial and magnetic sensors," Pattern Recognition, v. 43, pp. 3605-3620, 2010.

Avci et al., "Activity recognition using inertial sensing for healthcare, wellbeing and sports applications: A survey," 23rd International Conference on Architecture of Computing Systems, 2010.

Tapia et al., "Real-time recognition of physical activities and their intensities using wireless accelerometers and a heart rate monitor," 11th IEEE International Symposium on Wearable Computers, 2007.

* cited by examiner

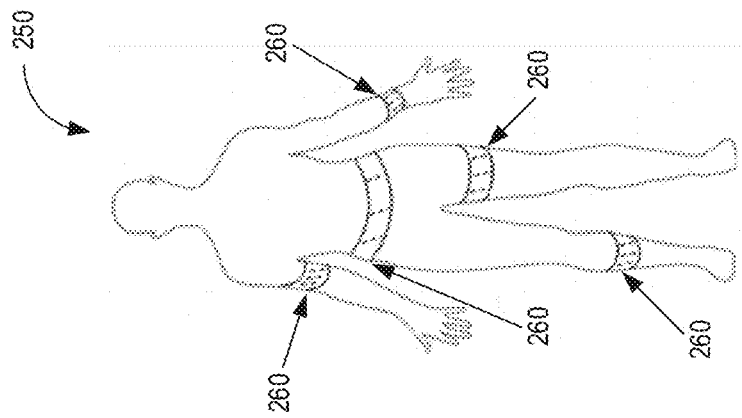
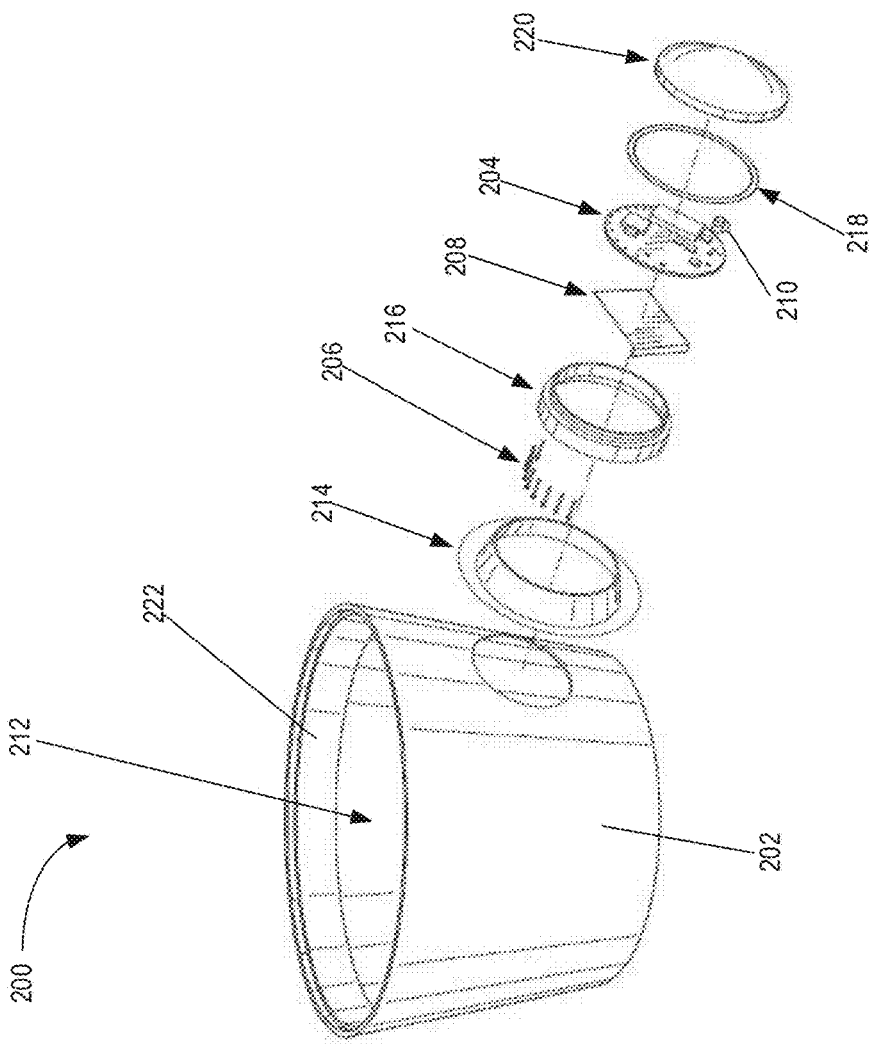
FIG. 2A
FIG. 2B

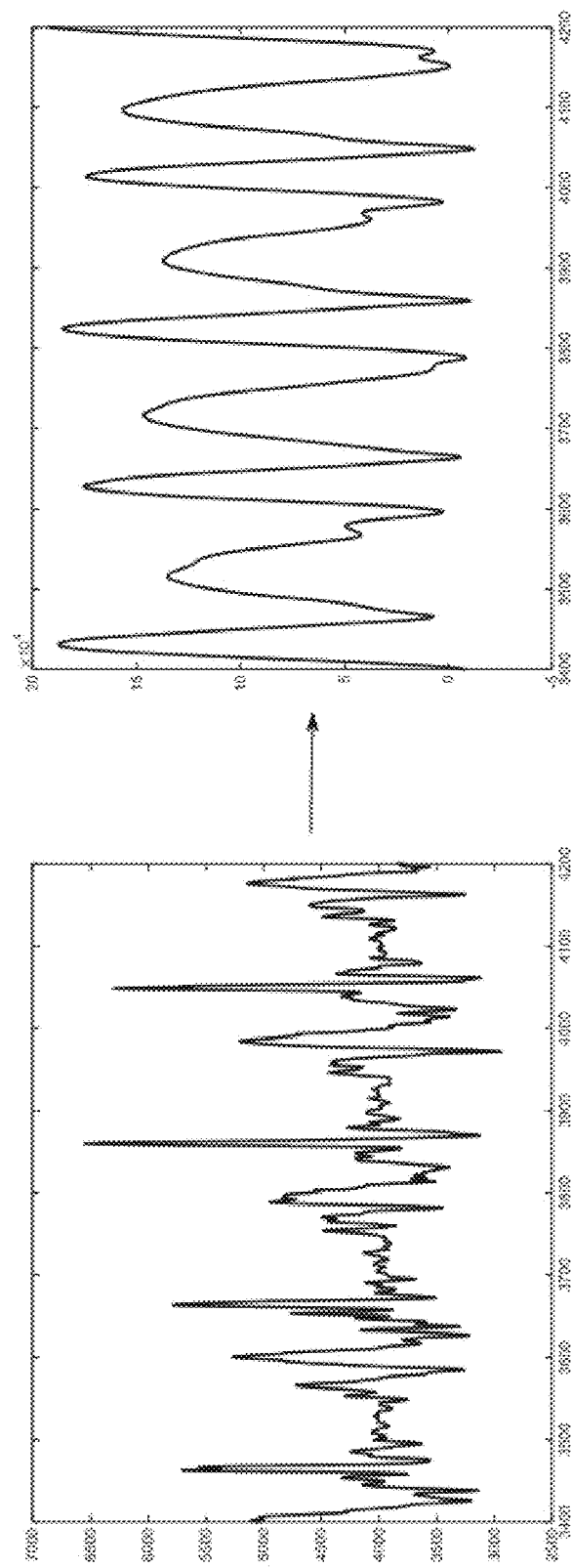

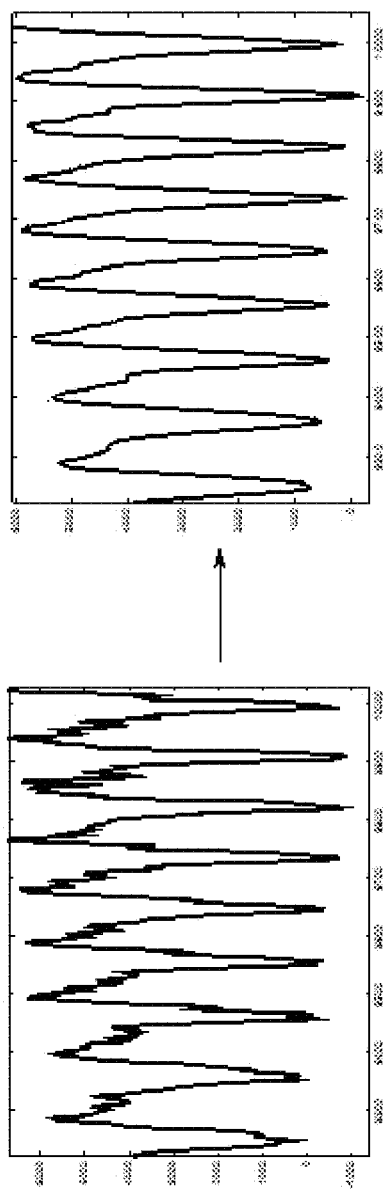

SYSTEMS, METHODS AND DEVICES FOR EXERCISE AND ACTIVITY METRIC COMPUTATION

CROSS-REFERENCE TO RELATED APPLICATIONS

This application claims the benefit of U.S. Provisional Patent Application No. 61/970,454, filed Mar. 26, 2014 and U.S. Provisional Patent Application No. 61/970,482, filed Mar. 26, 2014. The entire contents of U.S. Provisional Patent Application Nos. 61/970,454 and 61/970,482 are hereby incorporated by reference.

FIELD

The various embodiments described herein generally relate to systems, methods and devices for exercise metric computation. In particular, the various embodiments described herein relate to computation of exercise and physical activity metrics using a wearable device.

BACKGROUND

Wearable computing systems are an emerging category of devices. These devices enable users to perform a variety of tasks. For example, users may virtually interact with online accounts; record and/or observe information such as videos, images, and sounds; control other computing systems and other connected appliance; interact with other people; and in some instances monitor the current conditions, state and performance of an individual's body.

Devices capable of monitoring an individual's fitness have become increasingly popular. Monitoring and maintaining physical fitness is an ongoing concern for individuals with busy lifestyles, and this concern is becoming more pronounced with an aging population. As a result, demand is increasing for devices that can track physical activities and individual fitness.

SUMMARY OF VARIOUS EMBODIMENTS

In a broad aspect, at least one embodiment described herein provides a method of determining exercise metrics for a user's body using a wearable device, the method comprising: receiving a plurality of signals from at least one sensor of the wearable device; pre-processing the plurality of signals to generate a plurality of pre-processed signals; using a processor, discriminating the plurality of pre-processed signals to generate a plurality of signal segments for each of the plurality of pre-processed signals; computing at least one exercise metric based on the plurality of signal segments of the plurality of pre-processed signals.

In some embodiments, the at least one sensor comprises an accelerometer, and the plurality of signals comprise acceleration signals.

In some embodiments, the at least one sensor comprises a plurality of EMG sensors and at least two of the EMG sensors are positioned to detect EMG signals from different muscles of the user.

In some embodiments, the at least one exercise metric comprises a muscle intensity metric. In some embodiments, the at least one exercise metric comprises a muscle coordination metric. In some embodiments, the at least one exercise metric comprises a muscle ratio metric. In some embodiments, the at least one exercise metric comprises a muscle fatigue metric, and the computing comprises computing a shift in a frequency characteristic of at least one EMG signal.

In some embodiments, generating the plurality of signal segments comprises determining a temporal distance between the plurality of signal segments.

In some embodiments, the at least one sensor comprises a sensor selected from the group consisting of a gyroscope and a magnetometer.

In some embodiments, filtering the plurality of signals comprises low pass filtering each of the plurality of signals.

In some embodiments, generating the plurality of signal segments comprises generating a plurality of feature vectors based on the plurality of pre-processed signals, wherein each feature vector comprises a plurality of feature values, and wherein each feature vector is associated with a time step of the pre-processed signals.

In some embodiments, each feature vector comprises time domain and frequency domain data based on the plurality of pre-processed signals. In some embodiments, each feature vector is computed over a moving time window.

In some embodiments, generating the plurality of signal segments further comprises mapping the plurality of feature vectors onto a predetermined feature space.

In some embodiments, the mapping is predetermined by ANOVA computation over a training data set.

In some embodiments, the predetermined feature space is predetermined by Principal Component Analysis of a training data set.

In some embodiments, computing at least one exercise metric comprises performing, using the processor, hierarchical classification to compute a likeliest class for a current time step.

In some embodiments, generating the plurality of signal segments comprises applying an adaptive threshold.

In another broad aspect, at least one embodiment described herein provides a wearable device for determining exercise metrics for a user's body, the wearable device comprising: at least one sensor positionable on the user's limb; a processor operatively coupled to the at least one sensor, the processor configured to: receive a plurality of signals from at least one sensor of the wearable device; pre-process the plurality of signals to generate a plurality of pre-processed signals; discriminate the plurality of pre-processed signals to generate a plurality of signal segments for each of the plurality of pre-processed signals; compute at least one exercise metric based on the plurality of signal segments of the plurality of pre-processed signals.

In another broad aspect, at least one embodiment described herein provides a non-transitory computer readable medium storing computer-executable instructions, which, when executed by a computer processor, cause the computer processor to carry out a method of analyzing activity of a user's body using a wearable device positioned on a user's limb, the method comprising: receiving a plurality of signals from at least one sensor of the wearable device; pre-processing the plurality of signals to generate a plurality of pre-processed signals; using a processor, discriminating the plurality of pre-processed signals to generate a plurality of signal segments for each of the plurality of pre-processed signals; computing at least one exercise metric based on the plurality of signal segments of the plurality of pre-processed signals.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described:

FIG. 2A is a diagram illustrating an exploded view of an example embodiment of a wearable device that can be used in the system of FIG. 1;

FIG. 2B is a diagram illustrating various examples of the placement on a user's body of example embodiments of a wearable device;

FIGS. 14A and 14B illustrate example acceleration signals and pre-processed acceleration signals, respectively;

FIGS. 15A and 15B illustrate example acceleration signals and filtered acceleration signals, respectively;

Figure 1:
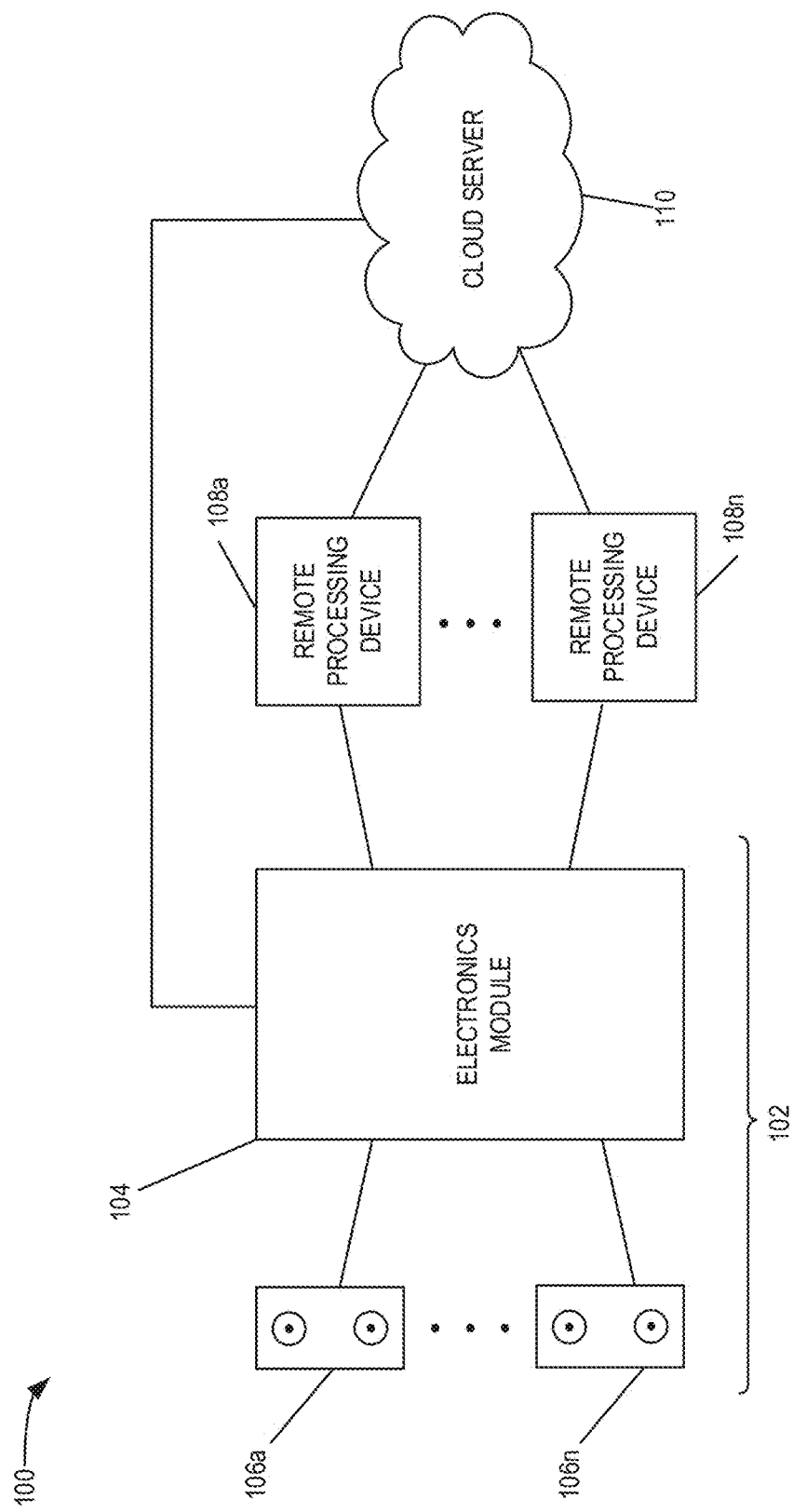
FIG. 1 is a block diagram illustrating an example embodiment of a system for activity tracking.

Further aspects and features of the embodiments described herein will appear from the following description taken together with the accompanying drawings.

DETAILED DESCRIPTION OF THE EMBODIMENTS

Various systems or methods will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" may be used to indicate that an element or device can electrically, optically, or wirelessly send data to another element or device as well as receive data from another element or device.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are example embodiments of systems, methods and wearable devices for determining various exercise metrics for an individual user. Generally, the various metrics can be determined by capturing movement or position data (e.g., using an accelerometer), or a plurality of electrical signals from a skin surface of the user, or both. Calibration data can be generated based on a subset of the captured electrical signals, and in some cases electromyography signals can be processed using the calibration data to determine at least one biometric. Examples of biometric features that may be determined in various embodiments described herein include muscle intensity, muscle coordination, muscle ratio, muscle fatigue, lactate levels, and hydration.

The example embodiments of the systems and methods described herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a pushbutton keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level computer programming language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Electromyography (EMG) measures electromyographic signals, which are electrical signals associated with muscle contractions. There are generally two methods for acquiring EMG signals. The first method may be referred to as needle electromyography, and is an invasive method that involves inserting electrical probes (needles) into target muscle tissues in order to acquire the EMG signal from the muscle. While needle electromyography has been used to measure and analyze muscle contractions and activity; this application has typically been limited to hospital or laboratory settings.

The second method is referred to as surface electromyography (sEMG) and involves placing sensors at the skin surface close to target muscles. While less invasive than needle EMG, sEMG has much lower specificity than needle EMG. Surface EMG signals result from the superposition of the sensed motor unit action potentials (MUAPs) from all the muscle fibers within sensing distance of the acquiring electrode. The MUAPs seen in the sEMG signal may be generated by the same muscle or may originate in different muscles. This can result in signal cross-talk where the sEMG energy from one particular muscle is sensed at an electrode location for a different muscle.

Acquired sEMG signals may also contain other undesirable components that are sensed along with the desired muscle activity. For instance, the undesirable components may include environmental noise (e.g. 60 Hz power line "hum") and/or body-produced signals such as electrical signals from the heart (electrocardiograph (ECG) signals).

Surface EMG may also be susceptible to "motion artifact" noise which results from the relative motion of the sEMG electrode and the muscle tissue. Motion artifact noise can result from muscle fibres moving underneath the surface of the skin relative to a fixed sensor position during a dynamic contraction (e.g. Bicep curl). This type of motion artifact is independent of the sensor used because the muscle always moves underneath the skin.

Motion artifacts may also occur where electrodes are positioned at the surface of the skin and can shift position relative to the muscles being targeted due to the skin's pliability. The "motion artifact" effect may be more pronounced when using electrodes embedded in a wearable device (such as textile electrodes or conductive polymers) as compared with sensors adhered to the surface of the skin. This may affect the signal contribution from target muscles as well as undesirable signal components acquired from nearby non-targeted muscles. In some cases, the "motion artifact" noise may appear as a low frequency component of the desired sEMG signal, while in other cases it may partially overlap signal components that include the desired frequency content of the sEMG signal. Examples of signal processing methods described in accordance with the teachings herein can be applied to remove the unwanted interference from acquired sEMG signals. Using compressive garments may also mitigate some of the motion artifact noise by reducing the motion of the electrodes in the garment relative to the targeted muscles.

Wearable devices and systems incorporating wearable devices have recently been developed for a variety of purposes. Wearable devices can be used for controlling and interacting with multimedia and other electronic devices, as well as for fitness and athletic applications. Described herein are example embodiments of wearable devices, systems incorporating one or more wearable devices, and methods for activity recognition and analysis. The systems, methods and devices described herein can be applied for fitness and athletic applications such as monitoring and analyzing performance, and avoiding injury.

The systems, methods and devices described herein can acquire a plurality of electrical signals, for example, from an accelerometer, and analyze those signals to recognize an exercise activity being performed by a user. In some cases, sEMG signals may also be analyzed in conjunction with the identified exercise activity to provide physiological insights to users. In addition to EMG signals, other electrical signals such as skin impedance signals and bio-impedance signals may be acquired. A user's biometric features, as well as other metrics, may be monitored and stored during physical activity and at other times. The biometric features and other metrics may be provided as real-time feedback to a user and/or tracked over time to monitor and illustrate a user's progress.

A user's body impedance provides a measure of how well the user's body impedes the flow of electric current. A user's body impedance can be separated into the impedance of the user skin surface, referred to as skin impedance, and the impedance of the user's body below the skin surface, referred to as bio-impedance. EMG signals acquired from a user's skin surface will be affected by the skin impedance.

A user's skin impedance generally depends on the condition of the surface of the user's skin. As a result, the user's skin impedance can change as the user performs an activity, for example when the user perspires. In general, a user's skin impedance will be lower when the skin surface is wet than when the skin surface is dry.

Bio-impedance can be affected by a user's body composition, as different tissue types tend to have different levels of resistivity. For example, fat tissue has high resistivity, while tissues with high water content will tend to have low resistivity. A user's bio-impedance can also fluctuate as the user performs an activity, for example due to changes in the user's hydration level, which can affect the user's intra-cellular and extra-cellular water content.

The various biometric features and metrics determined for a user may be analyzed to identify trends and alert users to those trends. This may enable users to adjust the activities they are performing, or how they are performing activities in response to the trends. For instance, the signal amplitude and frequency content of acquired EMG signals may be analyzed over time to identify muscle growth or muscle efficiency trends. Similarly, muscle coordination (the sequence in which an individual's muscles are operating) may be analyzed to provide recommendations to improve individual performance. Muscle balance (cross-body) may be tracked and recommendations may be provided to users to adjust their training if muscles appear to be unbalanced. The various biometric features and metrics may also be analyzed to identify an injury risk trend, provide feedback to a user indicating a potential risk of injury, and provide recommendations to avoid the potential risk of injury.

Muscle fatigue may be tracked and a fatigue alert may be provided to the user when a fatigue trend is identified. A fatigue alert may be used to prevent overtraining. In some embodiments, fatigue may be determined by measuring decreases in mean and median frequencies of EMG signals. For example, this may be done using machine learning algorithms pre-trained on a plurality of collected EMG signals.

Similarly, hydration may be tracked to provide feedback to a user to drink water or other fluids when their body exhibits signs of low hydration. Lactate levels may also be monitored to provide feedback to a user, and may provide a recommendation of reducing activity intensity when lactate levels are identified above a particular threshold.

Referring now to FIG. 1, shown therein is block diagram illustrating an example embodiment of a system 100 for biometric analysis. System 100 includes a wearable device 102, one or more remote processing devices 108 and a remote cloud server 110. In other embodiments, systems for biometric analysis in accordance with the teachings herein may not require any remote processing devices 108 or remote cloud server 110. In such embodiments, the processing of the bio-signals acquired from a user may be performed by electronic components included in wearable device 102.

Wearable device 102 can be removeably securable to a user skin surface with a skin-facing surface of the wearable device positioned to make contact with the skin surface. Wearable device 102 can generally be manufactured of a fabric, cloth or polymer material suitable for being worn in contact with a user's skin. A portion, or all, of the wearable device 102 can be made of breathable materials to increase comfort while a user is performing an activity.

In some embodiments, the wearable device 102 may be formed into a garment or form of apparel such as a band, shirts, shorts, and sleeves for example. In some cases, wearable device 102 may be a compression garment manufactured from a material that is compressive. A compression garment may minimize the impact from "motion artifacts" by reducing the relative movement of the wearable device 102 with respect to a target muscle. In some cases, wearable device 102 may also include anti-slip components on the skin-facing surface. For example, a silicone grip may be provided on the skin-facing surface of the wearable device 102 to further reduce the potential for motion artifacts. In some cases, the weave of a compression garment textile can be optimized to minimize motion artifacts by reducing motion in preferred directions of the textile weave. For example, additional compression (in addition to the compression elsewhere in the garment) can be added to a compression garment in locations having electrodes.

In some embodiments, wearable device 102 includes a plurality of electrodes 106a-106n positioned to acquire an electrical signal from the user's skin surface. In some embodiments, the electrodes 106 can be integrated into the material of the wearable device 102. Alternatively, the electrodes 106 can be affixed or attached to the wearable device 102, e.g., printed, glued, laminated or ironed onto the skin-facing surface. In some cases, the electrodes 106 may be provided separately from the wearable device 102 as an iron-on component that a user can then apply to the wearable device 102. Various other methods of affixing the electrodes 106 to the wearable device 102 may also be used.

Wearable device 102 may also be provided without electrodes 106a to 106n. In such embodiments, wearable device 102 may omit the acquisition and analysis of electromyography and other bio-signals, and may instead provide movement data. In some embodiments, the compression garment may also be omitted, and wearable device 102 may instead be provided as a small module that can be fastened, e.g., to a user's clothing using a clip, a hook and loop fastener, adhesive, or the like.

Various different electrodes 106 may be used with wearable device 102. For example, the electrodes 106 may be metallic, conductive polymers, conductive inks, or conductive textiles for example.

Wearable device 102 also includes an electronics module 104 coupled to the plurality of electrodes 106. Generally, the electronics module 104 can include a power supply, a controller, a memory, a signal acquisition unit operatively coupled to the controller and to the plurality of electrodes 106, and a wireless communication module operatively coupled to the controller. The signal acquisition unit may include a skin impedance acquisition module and an electromyography acquisition module. In some cases, the signal acquisition unit may also include a bio-impedance acquisition module and/or an analog-to-digital converter. Example embodiments of the wearable device 102 will be described in further detail below, with reference to FIGS. 2 to 4.

The electronics module 104 of the wearable device 102 can be communicatively coupled to one or more remote processing devices 108a-108n, e.g., using a wireless communication module (e.g., Bluetooth, IEEE 802.11, etc.). The remote processing devices 108 can be any type of processing device such as a personal computer, a tablet, and a mobile device such as a smartphone or a smartwatch for example. The electronics modules 104 can also be communicatively coupled to the cloud server 110 over, for example, a wide area network such as the Internet.

Each remote processing device 108 and remote cloud server 110 can include a processing unit, a display, a user interface, an interface unit for communicating with other devices, Input/Output (I/O) hardware, a wireless unit (e.g. a radio that communicates using CDMA, GSM, GPRS or Bluetooth protocol according to standards such as IEEE 802.11a, 802.11b, 802.11g, or 802.11n), a power unit and a memory unit. The memory unit can include RAM, ROM, one or more hard drives, one or more flash drives or some other suitable data storage elements such as disk drives, etc.

The processing unit controls the operation of the remote processing device 108 or the remote cloud server 110 and can be any suitable processor, controller or digital signal processor that can provide sufficient processing power processor depending on the desired configuration, purposes and requirements of the system 100.

The display can be any suitable display that provides visual information. For instance, the display can be a cathode ray tube, a flat-screen monitor and the like if the remote processing device 108 or remote cloud server 110 is a desktop computer. In other cases, the display can be a display suitable for a laptop, tablet or handheld device such as an LCD-based display and the like.

System 100 can generally be used for tracking biometric features, identifying activity, and measuring other metrics for a user. For example, the activity, biometric features and other metrics may be monitored, stored, and analyzed for the user. In different embodiments, aspects of the monitoring, storage and analysis of the different biometric features and other metrics may be performed by the wearable device 102, a remote processing device 108, or the cloud server 110.

The cloud server 110 may provide additional processing resources not available on the wearable device 102 or the remote processing device 108. For example, some aspects of processing the signals acquired by the electrodes 106 may be delegated to the cloud server 110 to conserve power resources on the wearable device 102 or remote processing device 108. In some cases, the cloud server 110, wearable device 102 and remote processing device 108 may communicate in real-time to provide timely feedback to a user regarding their current biometrics and any trends identified.

For example, one of the controller (on the wearable device 102) and the remote processing device 108 can be configured to capture a plurality of electrical signals including at least one sensor signal using the plurality of electrodes 106. The controller or the remote processing device 108 can generate calibration data based on a subset of the plurality of sensor signals acquired.

In some embodiments, the acquired electrical signals may include at least one skin impedance signal. The controller or the remote processing device 108 can generate the calibration data based on a subset of the electrical signals that includes the at least one skin impedance signal. Thus, the calibration data may be used to adjust the processing of the acquired electromyography signals to account for changes in skin impedance.

In embodiments where electromyography is used, the acquired sEMG signals may be variable depending on skin condition, accordingly calibrating the processing to respond to changes in skin impedance may account for changes in skin condition that affect the raw EMG signal acquired. For example, as a user begins to perspire, moisture accumulates on the skin surface, changing the skin's effective impedance. This can affect the acquired EMG signal, or it may be used as an indication of exertion. Therefore a "skin impedance signal" can be acquired and used to identify the skin impedance.

The skin impedance signal is a form of electrical signal that can be acquired by injecting a probe signal at a first electrode and receiving a resulting signal at a second electrode. Generally, skin impedance signals are injected and received through neighboring or proximate electrodes, to maximize the effect of skin impedance. The skin impedance signal can be analyzed periodically or continuously to account for the changes in the acquired EMG signal due to perspiration.

In some embodiments, bio-impedance signals may also be acquired by wearable device 102. Bio-impedance signals are another form of body impedance, which can be affected by changes in a user's hydration levels, among other factors. Dehydration can cause an increase in the body's electrical resistance, and the bio-impedance signals can be used to analyze an individual's hydration levels.

The bio-impedance signal is a form of electrical signal that can be acquired using a tetra-polar electrode configuration. A probe signal can be injected using a first pair of electrodes and a resulting signal can be received at a second pair of electrodes. The bio-impedance signal can be analyzed periodically or continuously to determine biometrics for the user such as changes in hydration levels. In some cases, bio-impedance signals may be injected and received through cross-body or otherwise distant electrode pairs. This may provide a broader view of the state of the user's body, as compared with a localized view that may be provided if the electrode pairs are close together. Accordingly, using cross-body or otherwise distant electrodes may improve the accuracy of the hydration analysis.

EMG signals can be collected using a differential pair of electrodes. That is, two electrodes can be used to acquire a differential signal for a single EMG acquisition channel. Typically, EMG signal collection can be paused while skin impedance signals and/or bio-impedance signals are acquired. The signal injection used to measure the skin impedance or bio-impedance may saturate the analog front end components of the EMG acquisition unit. Accordingly, the EMG signal collection can be paused while skin impedance or bio-impedance signals are acquired to avoid interference.

In some cases, a single set of electrodes can be used to acquire skin impedance signals, bio-impedance signals, and EMG signals. In such cases, the signal acquisition unit may include multiplexers (or switching networks) that can be used to switch between the skin impedance acquisition unit, bio-impedance acquisition unit and EMG acquisition unit. Example embodiments of signal acquisition units employing multiplexers will be discussed in further detail below with reference to FIGS. 4A to 4C.

In some embodiments, system 100 may include a plurality of wearable devices 102 that can be removeably secured to the user's skin surface. In some cases, each of the wearable devices 102 may communicate with each other or with remote processing device 108 or cloud server 110. Using a plurality of wearable devices 102 may better facilitate cross-body or contralateral comparisons of EMG signals and other acquired signals. This may facilitate additional biometric features to be determined from the acquired signals.

In some cases, prior to using a wearable device 102 a user may populate a user profile. The user profile may include user demographic data such as sex, height, weight, age, and other demographic details. In some embodiments, a user's demographic data may affect the processing used to determine activities, biometric features or other metrics for that user. For example, determined calorie expenditure may be affected by a user's height and weight, while lactate levels may be affected by a user's sex.

The user profile may also track the various activities, biometric features and other metrics determined for a user over time. Accordingly, a user's profile may include a historical record of one or more activities, biometrics or other metrics for that user.

The user profile may be stored in various locations. For example, in some embodiments a user's profile can be stored in a memory module of the wearable device 102 or in a remote processing device 108. A user's profile may also be stored in a cloud storage module on cloud server 110 in some embodiments. Where user profiles are stored in multiple locations, the various components may communicate to update features of the user's profile.

In some cases, different aspects of a user's profile may be stored in different locations due to storage limitations. For example, the wearable device 102 or remote processing device 108 may store limited portions of a user's profile necessary for determining activities, biometric features and other metrics. Additional portions of the user's profile could then be stored on the remote cloud server 110 for retrieval by (and syncing with) wearable device 102 and remote processing device 108.

In some cases, baseline initialization data may be generated for a user when they first use a wearable device 102. For example, the wearable device 102 or remote processing device 108 may indicate to the user basic activities to perform in an initialization routine. The initialization routine may include the individual performing activities that result in a maximum voluntary contraction (MVC) of target muscles with the wearable device 102 positioned to collect EMG signals from those muscles. The user may be instructed to perform particular activities with maximum strength, and the acquired EMG signals can be used as a reference for analysis of subsequently acquired signals. In some cases, muscle strength/power may be initialized through a standard cycling power meter and stored in the user profile for future reference.

The initialization process can be repeated for different target muscles and used to generate baseline physiological data. In some cases, some baseline physiological data may be provided with the wearable device 102 without requiring the user to perform a calibration routine. This baseline physiological data may be pre-generated based on aggregate calibration data from a number of other users. The baseline physiological data also may be adjusted based on demographic data provided in the user's profile. Baseline physiological data can be stored in the user's profile and used to identify changes or trends in the user's physiological state or physiological responses. In some cases, the baseline physiological data may be updated over time to account for changes in the user's physiology, as detected by system 100.

In some cases, the remote cloud server 110 may store a unique user profile for each user in a plurality of users. Each unique user profile may be associated with one or more wearable devices 102 used by the corresponding user. In some cases, the unique user profile may be associated with a particular remote processing 108 used by a user. The remote cloud server 110 may provide an interactive community for various users of the wearable devices 102 to compare activities, biometric features and other features determined by wearable devices 102.

The remote cloud server 110 may also enable longer term trends or patterns to be identified for a user or a collective of users. For example, remote cloud server 110 may analyze activity or biometric data acquired from a particular user over a period of time (e.g., several days, weeks, months or even years) to identify a patter indicative of potential injury or existing injuries. The remote cloud server 110 may then provide an alert to remote processing device 108 or wearable device 102 associated with that user alerting them to the identified trend. Monitoring and tracking various biometrics and metrics for a user over time can also be used to monitor rehabilitation progress and/or to monitor performance improvements over time. For example, trends can be used to ascertain training goals leading up to a set date, such as a competition date. This trend data can be used to facilitate the athlete "peaking" at the competition date.

Referring now to FIG. 2A, shown therein is an exploded view of an example embodiment of a wearable device 200, which may be an embodiment of wearable device 102. Wearable device 200 is an example of a band-type wearable device that can be worn at various positions on a user's body, as shown in FIG. 2B.

As shown, wearable device 200 is manufactured of an elastic or compressive material, such as neoprene, elastane or the like, with a plurality of electrodes interwoven into the material 202 of the wearable device. For example, the electrodes may be manufactured of conductive fabrics, to maintain the flexibility of wearable device 200. In one example embodiment, the material 202 may be an elastane polyester blend and the electrodes may be manufactured of conductive nylon.

However, in other embodiments, wearable device 200 may be manufactured of non-compressive material, or without interwoven electrodes. For example, electrodes may be fastened on the interior surface of wearable device 200 using a suitable adhesive, stitching or other fastener. In some cases, the electrodes can be secured in wearable device 200 by overmolding.

The electrodes may be located in specific regions of the wearable device 200 so as to be positioned proximate to target muscles. For example, where wearable device 200 is a thigh band, a set of electrodes may be positioned to overlie the vastus lateralis (VL) muscle of the quadriceps. In some cases, another set of electrodes may be positioned to overlie muscles of the hamstring. In other embodiments where wearable device 200 is intended to be worn over another limb, or another portion of a limb, electrodes may be positioned differently to overlie muscles of interest. In some cases, the electrodes can be configured to acquire an aggregate signal from a group of targeted muscles.

To ensure that a user has the wearable device 200 in a proper position for the embedded electrodes, wearable device 200 may also include an alignment guide to indicate the optimal orientation of the wearable device 200 when being worn. In some cases, the electrical signals received using the electrodes in the wearable device 200 may be compared to stored alignment data. Based on this comparison, an alert may be provided to the user to adjust the wearable device 200 for optimal sensor placement. In some cases, the stored alignment data may be dependent on the particular activity being performed by the user.

For example, the acquired electrical signals can be monitored for an expected sequence of muscle activations for a known movement associated with the activity. The acquired electrical signals can be compared with stored alignment data to identify any discrepancies in a received muscle coordination pattern. Based on the detection of a discrepancy, it can be determined that the sensors are not located in the optimal locations. In some cases, the amplitude of the acquired electrical signals can be analyzed. If the amplitude is below a predetermined amplitude threshold, it can be determined that the sensors are not proximal to the target muscle(s). In some cases, the frequency content of the received electrical signals can be analyzed to determine if motion artifact signal components are outside expected values. If so, this may indicate that the wearable device 200 is not being worn correctly.

In some cases, the alignment data can be generated by a user performing a baseline initialization routine. For example, the system 100 (e.g. wearable device 102 or remote processing device 108) may indicate to the user a sequence of actions that require the user to contract one or more muscles in a particular manner. The electrical signals acquired while the user performs the sequence of actions can be used to generate the alignment data. The alignment data can then be stored in the user profile on the wearable device 102, remote processing device 108 or remote cloud server 110. In some cases, the predetermined amplitude threshold can be determined based on the electrical signals acquired during the training routine and be stored as part of the alignment data.

In some cases, the plurality of electrodes in the wearable device 200 may include a greater number of electrodes than needed. This can be done to provide an even distribution of electrodes throughout the wearable device 200 to minimize the potential for misalignment. In such cases, the signals received from the plurality of electrodes can be compared with stored alignment data, and a subset of electrodes having desired signal components can be identified for use, based on the comparison.

Conductive wires 206 are coupled to the electrodes to convey the acquired signals to circuit board 204. In some cases, the conductive wires 206 may be conductive textile threads. The conductive wires 206 may be gold-plated to improve conductivity. Circuit board 204 contains the various electronic components of wearable device 200 such as a signal acquisition unit and controller. Electronic components of wearable device 200 will be described in further detail below with regard to FIGS. 3 and 4.

The wearable device 200 also includes a battery 208 to power the circuit board 204. In some cases, one or more user inputs 210 may be provided to allow a user to activate/deactivate the wearable device 200 or adjust parameters of the wearable device. For example, the user input 210 may be a push button or capacitive sensor that can be used to activate the wearable device 200.

One or more status indicators, such as light emitting diodes (LEDs), or a display, may be provided on outer cover 220 to indicate the status of wearable device 200 to the user. In some cases, a display integrated into outer cover 220 may also provide additional feedback to a user that may include biometrics or other metrics determined according to the teachings described herein. The wearable device 200 may also include haptic feedback modules to provide haptic feedback to a user regarding the status of the wearable device 200 or alerts regarding the biometrics or other metrics determined for that user.

The various electronic components of the wearable device 200, such as a controller, communication unit and accelerometer, can be contained within a waterproof casing. The waterproof casing can be provided by water-tight casing 216, outer cover 220 and an O-ring 218 between the water-tight casing 216 and the outer cover 220. The waterproof casing can prevent malfunctioning of the electronic components of the wearable device 200 by preventing liquids such as sweat or rain water from coming into contact with the circuit board 204. This may also allow the wearable device 200 to be cleaned after use to improve hygiene. In some cases, the electronic components in the water-tight casing can be removed from wearable device 200 to ensure that they are not damaged when wearable device 200 is cleaned.

In some embodiments, wearable device 200 may omit the sleeve, and be contained within water-tight casing 216. In such embodiments, water-tight casing 216 may be provided with a fastener for attachment to a user's body or clothing. For example, the fastener may be a clip, an adhesive strip, part of a hook and loop closure, or the like.

Wearable device 200 may also include an electronics module seat 214. The seat 214 can be used to join the electronic components of the wearable device to the materials to be worn on the user's skin surface. The seat 214 may be a rubberized ring to minimize the rigidity felt by a user. This may minimize the discomfort felt by a user, and reduce potential interference with normal range of motion. In some cases, the electronic components of the wearable device may be environmentally sealed and joined to the material 202 of the wearable device 200 using an overmold process. This may also provide a waterproof casing for the electronic components of wearable device 200.

Referring now to FIG. 2B, shown therein is a diagram 250 illustrating some examples of locations where a wearable device 260, such as wearable device 200, may be removeably secured to a user's skin surface. In the example shown in FIG. 2B, wearable devices 260 are shown attached to the user skin surface at the upper arm, lower arm, waist, thigh and lower leg. A skilled person will appreciate that other suitable placements may also be selected for a wearable device 260.

In some cases, the particular placement of a wearable device 260 may be determined based on a particular activity being undertaken by an individual. In some cases, an individual may select a particular placement based on nearby muscle groups the individual wishes to track. For example, a user may select the thigh or lower leg when targeting different muscles in the legs, and the lower or upper arm when performing activities that target the muscles of the arms.

In some cases, an individual may select a particular placement for a wearable device 260 because it is close to or distant from large muscle groups. For example, a user may select a hip bone as a placement for a wearable device as that region does not have high intensity muscle activity in its immediate vicinity. In some cases, one or more electrodes in a wearable device 260 may be used as reference electrodes that are not intended to capture EMG signals. For example, a reference electrode may be placed on the user's hip bone, at a location distant from most muscle activity, thereby minimizing the contribution of EMG signals to the electrical signals acquired by the reference electrode.

In some cases, the particular placement of a wearable device 260 may be dependent on the size or shape of that particular wearable device. For example, a wearable device 260 that can be placed around a user's waist may be different from a wearable device 260 that can be placed around a user's calf or forearm.

Figure 3:
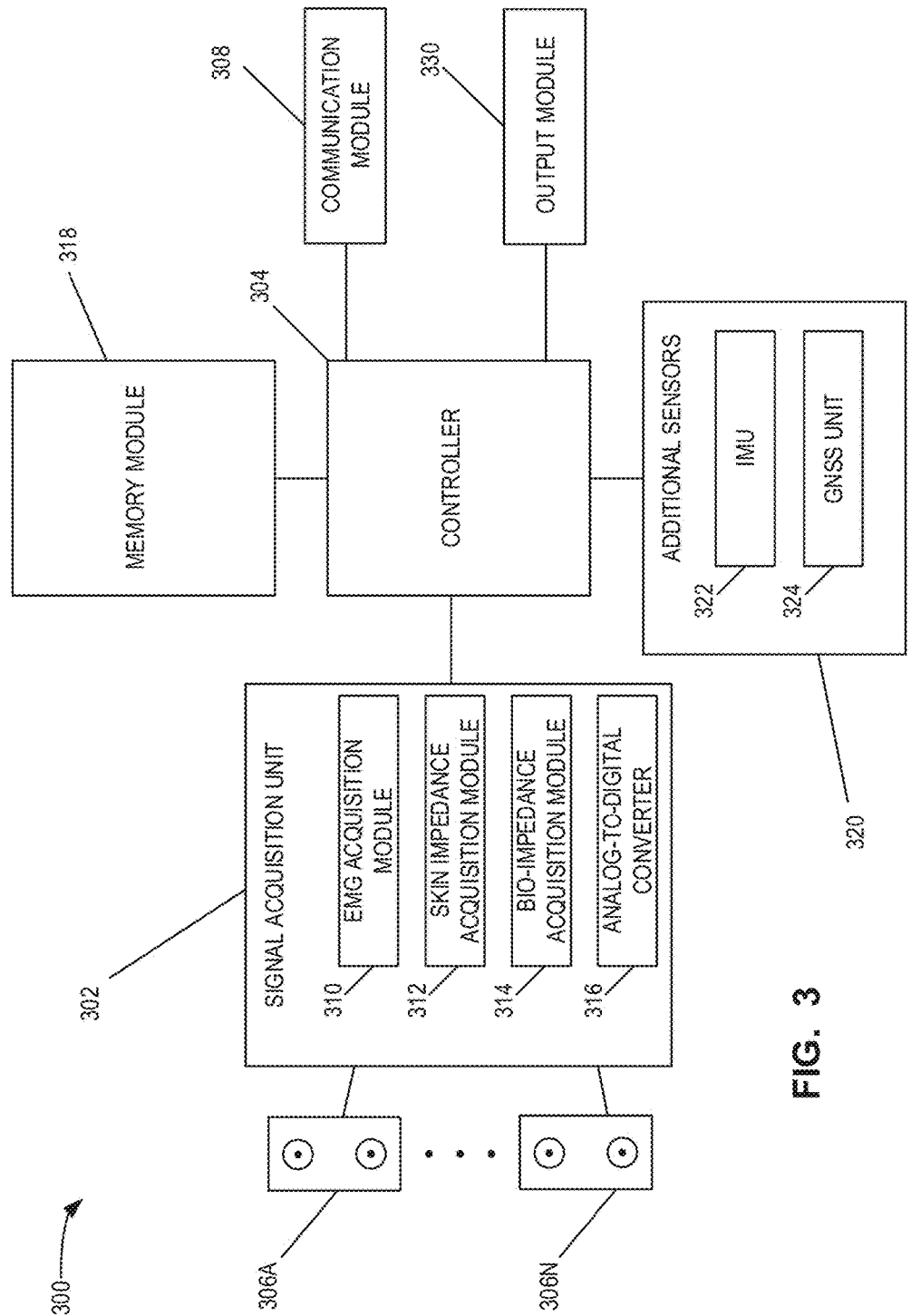
FIG. 3 is a block diagram illustrating various components of an example embodiment of a wearable device.

Referring now to FIG. 3, shown therein is a block diagram of an example embodiment of a wearable device 300. Wearable device 300 is an example embodiment of a wearable device 102, 200 or 260 that can be used in activity tracking system 100. In various embodiments, wearable device 300 can include additional components not shown in FIG. 3, such as a battery module, an input module or user interface.

In some embodiments, wearable device 300 includes a plurality of electrodes 306A-306N. The plurality of electrodes 306 are positioned in wearable device 300 to acquire an electrical signal from a user's skin surface when wearable device 300 is secured to the user's skin surface. For example, the electrodes 306 may be exposed on the skin-facing side of the wearable device 300 such that they are in contact with the user skin surface when the wearable device 300 is secured to the user skin surface. In some embodiments, some or all of the electrodes 306 may be capacitively coupled to the user skin surface, in which case they may not make electrical contact with the skin surface (e.g., due to an insulating coating).

In some embodiments, the electrodes 306 may be passive electrodes. In other embodiments, some or all of the electrodes 306 may be active sensors or electrodes, which contain active electronics that may require power to operate. Examples of active electronics include front-end amplifiers or filters. Given the low signal-to-noise ratio (SNR) often found with sEMG signals, active sensors may be used to increase front-end gain and reject common-mode noise. This can increase SNR of the acquired electrical signals before further processing.

Passive electrodes may be preferred in some applications due to the low-energy associated with their use. This can prolong the battery life of wearable device 300 thereby improving its utility for tracking a user's activity over prolonged periods. Passive electrodes may also be more easily integrated in garments.

In some embodiments, electrodes may be omitted.

In some embodiments, wearable device 300 can incorporate a compression garment or compressible garment. A compression garment can be used to reduce the relative movement between the location of the electrodes 306 and muscles being targeted. This can minimize the effect of motion artifacts on the EMG signals acquired. In other embodiments, the compression or compressible garment may be omitted.

In some embodiments, wearable device 300 also includes signal acquisition unit 302. Signal acquisition unit 302 can be used to receive and process, or pre-process, the signals acquired using electrodes 306. In other embodiments, for example when electrodes are not provided, signal acquisition unit 302 may be omitted.

Signal acquisition unit 302 can include an EMG acquisition module 310, a skin impedance acquisition module 312, a bio-impedance acquisition module 314 and an analog-to-digital converter 316 (A/D converter). In some embodiments, analog-to-digital converter 316 can be implemented using a high resolution, high dynamic range A/D converter. For example, the analog-to-digital converter 316 may sample the electrical signals acquired by electrodes 306 at, for example, 500 to 8000 samples per second and convert the signals to discrete time series data signals.

In some cases, one or more of EMG acquisition module 310, skin impedance acquisition module 312, bio-impedance acquisition module 314 may amplify the analog signal (to increase SNR) before providing the analog signal to A/D 316. In some cases, EMG acquisition module 310, skin impedance acquisition module 312, bio-impedance acquisition module 314 may provide unfiltered signals to analog-to-digital converter 316. Example embodiments of signal acquisition unit 302 will be described in further detail below with reference to FIG. 4.

Signal acquisition unit 302 may be configured to acquire a plurality of analog electrical signals using the plurality of electrodes 306 and to convert the acquired electrical signals in unfiltered form to digital signals using analog-to-digital converter 316. For example, A/D converter 316 may sample a continuous time analog EMG signal or other electrical signal and convert them to discrete time samples digital signals. This may provide a high quality digital signal with high levels of both undesirable signal components (e.g., noise) and EMG signals of interest (or skin impedance signal or bio-impedance signals). Various digital signal processing techniques can then be used to extract the desired signal components for analysis in determining biometric features and other metrics.

In some embodiments, signal acquisition unit 302 may not require A/D converter 316. For example, where controller 304 has a built-in A/D converter, A/D converter 316 may not be necessary. In such cases, the EMG acquisition module 310, skin impedance acquisition module 312, and bio-impedance acquisition module 314 may be coupled directly to controller 304.

Signal acquisition unit 302 is operatively coupled to controller 304. Controller 304 can be configured to control the signal acquisition unit 302 and to acquire a plurality of electrical signals using the plurality of electrodes 306. In some embodiments, controller 304 may also be configured to process the acquired electrical signals to determine at least one biometric feature or other metric. Controller 304 may be, for example, a microcontroller or a microprocessor, such as an ARM-based processor.

Controller 304 may be operatively coupled to memory module 318. In some cases, memory module 318 may include volatile and/or non-volatile memory. Non-volatile memory can be used to store program data, such as executable instructions, and signal data such as raw and/or processed electrical signal data (e.g. EMG data, skin impedance data, bio-impedance data), motion sensor data, calibration data, and operational parameters for example. Similarly, volatile memory may be used to store program data and signal data on a temporary basis.

Controller 304 may also be operatively coupled to a communication module 308. Communication module 308 may be a wireless communication module used to communication with remote processing device 108 or cloud server 110. In some cases, controller 304 may communicate the unprocessed digital signals received from analog-to-digital converter 316 to remote processing device 108 for further processing. For example, communication module 308 may communicate with remote processing device 108 using various communication protocols such as Bluetooth™ Low-Energy (BTLE), ANT+ or IEEE 802.11 (WiFi™).

Communication module 308 may also include other interfaces for communicating with remote processing devices 108 and cloud server 110. For example, communication module 308 may include ports for wired connections such as a Universal Serial Bus (USB) or other port. In some cases, wearable device may also include removable storage modules such as an SD card for transferring acquired data to a remote processing device 108.

Controller 304 can operate as an interface between the signal acquisition unit and the processing of the acquired signals. In some cases, controller 304 may process the acquired signals itself in real-time or near real-time. In some cases, controller 304 may store the unprocessed signals or transmit processed or unprocessed signals to a remote processing device 108 or cloud server 110 for analysis using communication module 308.

Controller 304 can be coupled to additional sensor module 320. Motion sensor module 320 may include one or more motion sensors used to acquire data regarding an activity being undertaken. In wearable device 300 as shown, the motion sensor module 320 includes an inertial measurement unit (IMU) 322 and a Global Navigation Satellite System (GNSS) unit 324, however other sensors may also be used.

IMU 322 can include one or more sensors for measuring the position and/or motion of the wearable device. For example, IMU 322 may include sensors such as a gyroscope, accelerometer (e.g., a three-axis accelerometer), magnetometer, orientation sensors (for measuring orientation and/or changes in orientation), angular velocity sensors, or inclination sensors. Generally, IMU 322 includes at least an accelerometer.

GNSS unit 324 may also include one or more sensors or devices used to determine the GNSS coordinates of the wearable device using one or more GNSS system, such as the Global Positioning System (GPS), Galileo, GLONASS, or the like. GNSS coordinates can be used to track a user's movement or determine location, and supplement the motion data from IMU 322 and the analysis performed by controller 304. GNSS coordinates can also be provided to cloud server 110 to facilitate comparisons or communication with other users in close proximity. GNSS coordinates can also be used to determine various metrics related to the user activity, such as weather and other atmospheric information.

Wearable device 300 may also include an output module 330 coupled to controller 304. Output module 330 may include one or more output or feedback devices that can provide a user of wearable device 300 with information regarding the status of wearable device 300 as well as feedback on the user's biometrics and other metrics. For example, output module 330 may include one or more status indicators such as an LED, light, or a haptic feedback module. Output module 330 may also include a display such as an OLED or LSC display for providing feedback and indications of status to the user.

Figure 4A:
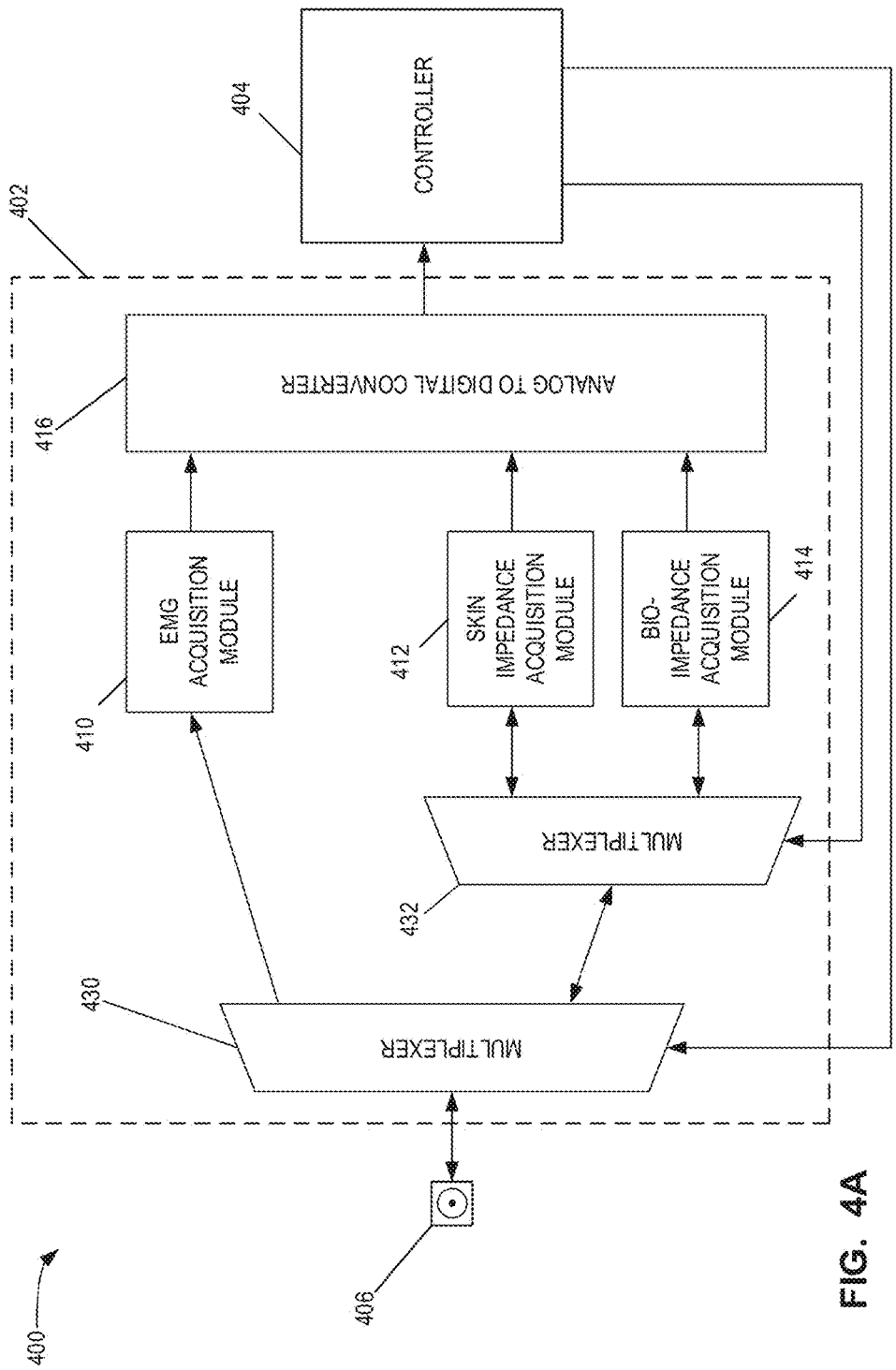
FIG. 4A is a block diagram illustrating various components of an example embodiment of a signal acquisition unit for a wearable device.

Referring now to FIG. 4A, shown therein is a block diagram 400 illustrating components in an example embodiment of a signal acquisition sub-unit 402, which may be used in an embodiment of signal acquisition unit 302.

Signal acquisition sub-unit 402 illustrates how multiplexers can be used to allow skin impedance signals, bio-impedance signals, and EMG signals to be acquired using the same electrodes. In some cases, a signal acquisition unit may include two signal acquisition sub-units such as signal acquisition sub-unit 402, each coupled to a separate electrode pair. In some cases, each signal acquisition sub-unit may have a separate A/D converter, while in other embodiments a single A/D converter can be used to convert the electrical signals acquired by each signal acquisition sub-unit. Another example embodiment of a signal acquisition unit employing multiplexers will be described with reference to FIG. 4B.

Signal acquisition sub-unit 402 is coupled to an electrode pair 406 and a controller 404. As shown in block diagram 400, the signal acquisition unit 402 includes a primary multiplexer 420 and the signal acquisition unit 402 is coupled to electrode pair 406 by primary multiplexer 430. Signal acquisition sub-unit 402 also includes EMG acquisition module 410, skin impedance acquisition module 412, bio-impedance acquisition module 414 and A/D converter 416. The EMG acquisition module 410 is coupled directly to the primary multiplexer 430.

Signal acquisition sub-unit 402 further includes a secondary multiplexer 432. Each of the skin impedance acquisition module 412 and the bio-impedance acquisition module 414 is coupled to the primary multiplexer 430 by the secondary multiplexer 432. The primary multiplexer 430 and secondary multiplexer 432 can be used to switch the acquisition units that are currently sampling the electrodes of electrode pair 406. This can enable the same electrodes to be used by the EMG acquisition module 410, skin impedance acquisition module 412, and bio-impedance acquisition module 414.

Figure 4B:
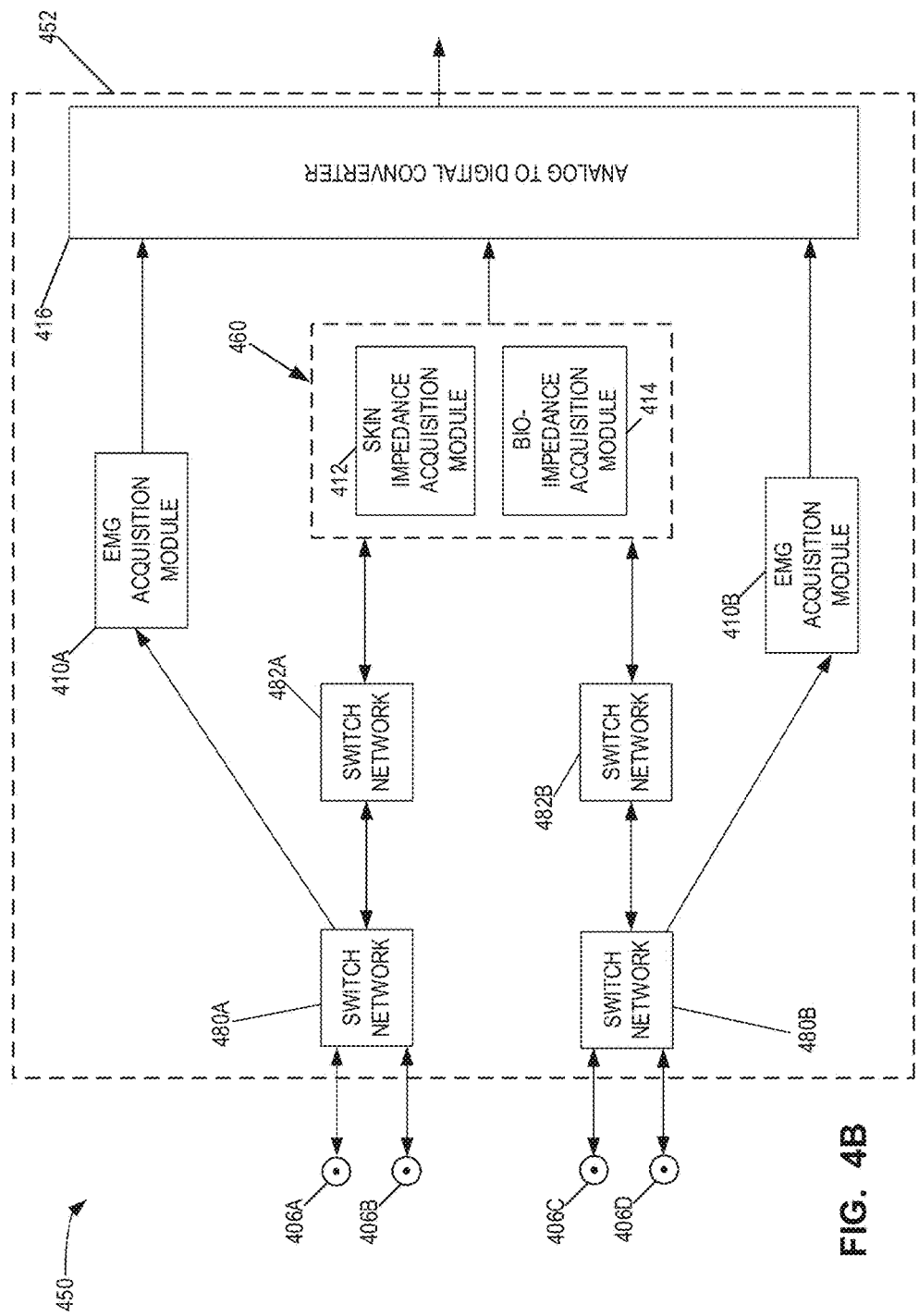
FIG. 4B is a block diagram illustrating various components of another example embodiment of a signal acquisition unit for a wearable device.

Referring now to FIG. 4B, shown therein is block diagram 450 showing components in an example embodiment of a signal acquisition unit 452, which may be an embodiment of signal acquisition unit 302. In the example shown in block diagram 450, signal acquisition unit 452 is coupled to 4 electrodes 406A, 406B, 406C and 406D. When a wearable device is secured to a user skin surface, the electrodes 406 can be positioned to acquire electrical signals from the skin surface.

As shown in block diagram 450, the electrodes may be configured as a first electrode pair 406A and 406B, and a second electrode pair 406C and 406D. Each electrode pair is coupled to a primary switch network 480 (i.e. multiplexer) of the signal acquisition unit 452. The primary switch networks 480A and 480B may be referred to as a primary multiplexer module. The primary multiplexer module can be used to switch between an EMG signal acquisition mode where EMG signals are collected and an impedance signal acquisition modes where impedance signals (i.e. skin impedance or bio-impedance) are collected.

As mentioned above, EMG signals can be acquired using a pair of electrodes to collect a differential signal. Accordingly, signal acquisition unit 452 includes a first EMG acquisition module 410A coupled to a first pair of electrodes (406A and 406B) by primary switch network 480A, and a second EMG acquisition module 410B coupled to a second pair of electrodes (406C and 406D) by primary switch network 480B. Accordingly, signal acquisition unit 452 may be used to collect EMG signals using the first electrode pair or the second electrode pair.

Signal acquisition unit 452 also includes secondary switch networks 482A and 482B. The secondary switch networks 482A and 482B may be referred to as a secondary multiplexer module. The secondary multiplexer module can be used to switch between a skin impedance acquisition mode and a bio-impedance acquisition mode, using the same set of electrodes 406.

The controller (not shown) can transmit multiplexer controller signals to the primary multiplexer module and the secondary multiplexer module to switch the signal type being sampled. The primary multiplexer module can be used to switch between acquiring an EMG signal using EMG acquisition module 410 and one of a skin impedance signal and a bio-impedance signal depending on the state of the secondary multiplexer module. Secondary multiplexer module can be used to switch between acquiring a skin impedance signal using skin impedance acquisition module 412 and a bio-impedance signal using bio-impedance acquisition module 414.

When signal acquisition unit 452 operates in a skin impedance acquisition mode, a signal can be injected using a first electrode of one of the electrode pairs (e.g. electrode 406A) and then a corresponding skin impedance signal can be received using a second electrode of the electrode pair (e.g. electrode 406B). The injected and received signals can be compared to determine the user skin impedance. When signal acquisition unit 452 operates in a bio-impedance acquisition mode, a signal can be injected using the first electrode pair and then a corresponding bio-impedance signal can be received using the second electrode pair. The injected and received signals can then be compared to determine the user bio-impedance In some cases, the skin impedance acquisition module 412 and bio-impedance acquisition module 414 may be provided in a combined impedance module 460. The impedance module 460 may be provided as multi-channel signal injection and sensing module (as is shown in FIG. 4B). In alternate embodiments, the impedance module 460 may be a single-channel signal injection and sensing module, in which case the secondary multiplexer module may include an additional cascade of multiplexers.

In the signal acquisition unit 452, A/D converter 416 can switch between the input channels from the EMG acquisition module 410, skin impedance acquisition module 412, and bio-impedance acquisition module 414 and provide the corresponding digital signals to the controller.

In some embodiments, A/D converter 416 may have sufficient input and output channels to process multiple signals in parallel. In some cases, multiple A/D converters can be used in parallel to increase the number of channels that can be digitized at the same time or to increase the effective sampling rate.

Figure 4C:
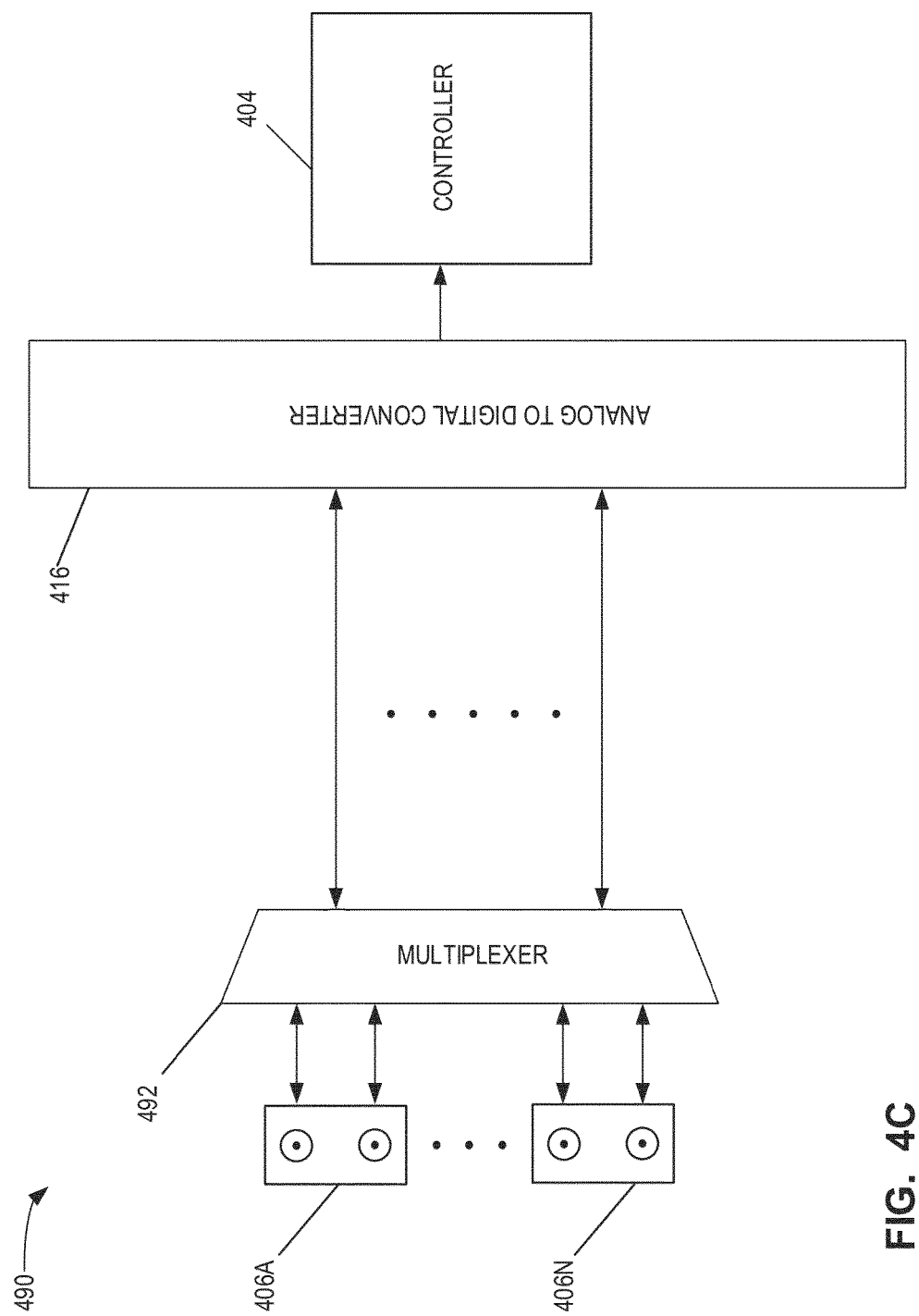
FIG. 4C is a block diagram illustrating various components of a multiplexer configuration that may be used in an example embodiment of a signal acquisition unit for a wearable device.

Referring now to FIG. 4C, shown therein is a block diagram 490 illustrating components of an example multiplexer configuration that can be used in an example embodiment of a signal acquisition unit to reduce the number of input channels of the A/D converter 416. In block diagram 490, various components of the signal acquisition unit, such as the skin impedance, bio-impedance and EMG acquisition modules have been excluded for ease of understanding.

Block diagram 490 illustrates an alternate configuration of a signal acquisition unit where one or more multiplexers 492 can be used to couple a plurality of N electrodes 406 to an A/D converter having M channels, where M is less than N. This can reduce the cost of the A/D converter used to produce a wearable device such as wearable device 300.

The controller 404 and signal acquisition unit (the details of which are not shown in FIG. 4C for clarity) can be configured to oversample the electrical signals acquired by the plurality of electrodes 406 to accommodate multiplexing performed by multiplexer 492. Where a wearable device includes N electrodes 406 and the A/D converter 416 has M input channels, a sampling rate ($f_{sampling}$) determined using equation (1) can be used to sample the electrical signals acquired by electrodes 406 (using acquisition frequency $f_{acquisition}$).

$$f_{sampling} \geq 2\left(\frac{N}{M}\right)f_{acquisition} \qquad (1)$$

For example, if an acquisition frequency of 1 kHz is specified to acquire electrical signals using four electrodes 406 (i.e. N=4), and the A/D converter 416 has a single input channel (i.e. M=1) the controller 404 and signal acquisition unit may be configured to sample the electrical signals acquired by the electrodes at eight times the acquisition frequency (i.e., 8 kHz).

Figure 5:
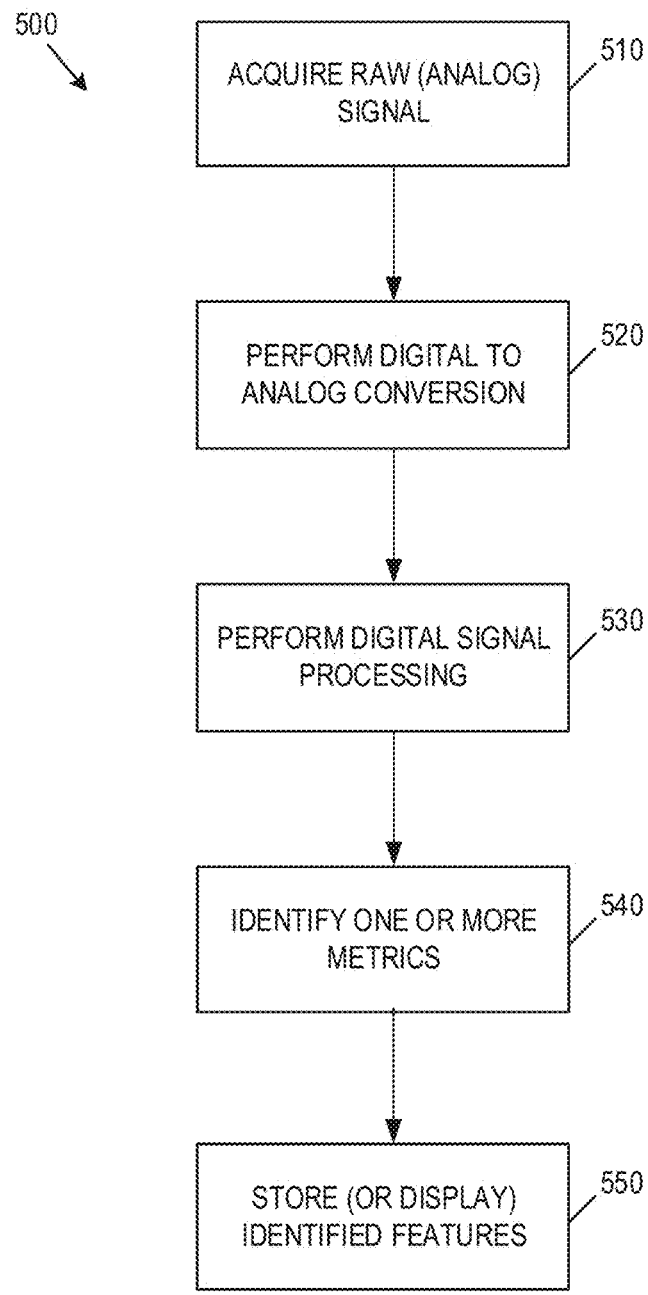
FIG. 5 is a flowchart illustrating an example embodiment of the processing that may be performed on acquired signals when using the system of FIG. 1.

Referring now to FIG. 5, shown therein is a process flow 500, illustrating various biometric acquisition and processing steps that may be performed using the described embodiments, such as wearable device 300 or system 100. Flow 500 may be performed using embodiments in which electrodes and a signal acquisition unit are provided.

At 510, one or more raw analog electrical signal is acquired from one or more electrodes. Generally, a plurality of electrical signals will be acquired in this fashion. Each signal can be acquired using one of a plurality of electrodes such as electrodes 106, 306 and 406. In some cases, each electrical signal may be amplified before being provided to an A/D converter. In other cases, each acquired electrical signal may be provided directly to the A/D converter.

At 520, each acquired analog signal is converted to a digital signal. For example, an A/D converter such as A/D converters 316 and 416 can be used to sample and convert each analog signal to respective discrete time digital signals.

At 530, various digital signal processing techniques can be used to filter undesired components from each digital signal. For example, traditional digital signal processing techniques in either the time or frequency domain can be used to filter unwanted noise such as power line hum, motion artifacts, radio frequency etc. Examples of time domain processing techniques that may be used at 530 includes digital filters such as finite impulse response (FIR), infinite impulse response (IIR) and moving average (MA) filters.

In some cases, the acquired EMG signals may be filtered to exclude frequency content outside of a frequency range associated with EMG signals. For example, the acquired EMG signals may be filtered using a band-pass filter tuned to pass a predetermined frequency range associated with EMG signals. In some cases, the predetermined frequency range may include frequencies between 30 Hz and 180 Hz.

At 540, each processed signal can be analyzed to classify the signal and extract signal components of interest and to identify biometric features and other features of an activity being tracked. In some cases, one or more of the processed electrical signals may be combined with motion sensor signals from motion sensors such as IMU 322 and GNSS 324 for example. Analysis of the various received signals can be used to determine biometric features and other metrics for the user.

Additional signal information such as motion or position information (e.g., acquired from the IMU or GNSS unit) and other electrical signals such as skin impedance signals and bio-impedance signals can be analyzed along with the acquired EMG signals to determine biometrics and other metrics for a user. In some embodiments, data from the EMG signal and secondary signals can be assessed together. Alternatively, in some embodiments, data from the EMG signal and secondary signals can be assessed separately. Optionally, analysis of the EMG and secondary sources can be conducted concurrently or consequently. In embodiments where the analysis is conducted consequently, results from the analysis of the first parameter can inform the analysis of the second parameter.

For example, a processed EMG signal may be analyzed in conjunction with analysis of other signals such as a skin impedance signal and/or a bio-impedance signal. The skin impedance signal can be used to generate calibration data that can be used when analyzing the processed EMG signal. The calibration data may allow the analysis to account for changes in the user's physiology that are not apparent from the EMG signal alone.

Examples of biometric features may include muscle intensity, muscle coordination, muscle ratio, muscle balance, muscle fatigue, activity intensity, lactate, hydration, muscle efficiency, heart rate, respiratory rate, blood pressure, and breathing volume among others. Examples of other metrics for a user may include location, weather time, distance, calories, Vo2 max, body temperature, glucose levels, acceleration, speed, cadence, activity, pedal position, mechanical power, seat height, inclination, wind velocity, ambient temperature, humidity, air pressure, altitude among others. In some cases, the particular activity being performed by the user can also be identified based on the acquired signals being analyzed.

When multiple muscles are monitored, especially from opposite sides of the body, a comparison between electrical signals received from sensors near identical muscles (on opposite sides of the body) may be used to detect a possible muscle imbalance in one of the muscles. This can be done by comparing the temporal length and intensities of the received EMG signals for those muscles, in combination with sensor signals related to motion and/or position.

For example, to monitor muscle balance while a user is running, a pair of wearable devices 102 may be used. Each device may be positioned on the upper thigh of each user's leg with the plurality of electrodes positioned to acquire an EMG signal from the vastus lateralis (VL) muscle of the quadricep complex on both legs. The amplitude of the EMG signals may be assessed in combination with motion signals from the IMUs in each wearable device to determine whether the user's running stride is balanced. Muscle imbalance may be indicative of improper form or an impending injury. Various other features could be extracted from EMG signals to give users valuable feedback on other biometrics.

In various embodiments, the digital signal processing performed at 530 and the feature extraction and classification performed at 540 can be performed by various components of activity tracking system 100. For example, in some embodiments, the digital signal generated at 520 may be provided directly to remote processing device 108 or a cloud server 110 without any digital processing being performed by wearable device 102.

In different embodiments, the signals may be processed at 530 by either remote processing devices 108 or cloud server 110. Similarly, the feature extraction and classification preformed at 540 can also be performed by the remote processing device 108 or the cloud server 110. In some cases, cloud server 110 may perform feature analysis in addition to feature analysis performed by a remote processing device 108, for example to identify longer term trends for a user.

In some embodiments, the controller of the wearable device 102 can perform the signal processing at 530. In some cases, the wearable device 102 can then provide the processed signal data to a remote processing device 108 or cloud server 110. In other cases, the controller may also perform some or all of the feature extraction and classification at 540. In embodiments where multiple wearable devices are used to assess biometrics or other metrics, one or more of the multiple wearable devices may perform the signal processing, including feature extraction and classification.

At 550, the biometric features and other metrics identified at 540 can be stored or provided to a user as feedback. In various embodiments the features identified at 540 may be stored in memory module 318 on wearable device 300, in a memory module of remote processing devices 108, in a cloud storage module of cloud server 110, or in a combination of these storage locations.

Examples of biometric features may include muscle intensity, muscle coordination, muscle ratio, muscle balance, fatigue, activity intensity, lactate, hydration, muscle efficiency, heart rate, respiratory rate, body temperature, blood pressure, breathing volume, Vo2 max, and glucose levels among others.

Other metrics that do not require electromyography may also be acquired, as described herein. Examples of other metrics for a user may include location, weather time, distance, calories, acceleration, speed, cadence, activity, pedal position, mechanical power, seat height, inclination, wind velocity, ambient temperature, humidity, air pressure, altitude among others. In some cases, the particular activity being performed by the user can also be identified based on the acquired signals being analyzed In some cases, the wearable device or a remote processing device (e.g., a mobile phone) may include a display. The wearable device or remote processing device can be configured to display feedback based on the at least one biometric identified at 540. For example, the feedback provided to a user may be a report or a visualization of the at least one biometric.

In some cases, the remote processing device or wearable device may include a user interface for changing or adjusting the display being provided. For example, the display may include different reports or visualizations, and a user may be able to scroll or browse through the different feedback available. In some cases, the configuration of the feedback on the display can also be customized based on a user's preferences.

In some cases, the display on the remote processing device or wearable device can be placed into a sleep mode to reduce battery consumption. The display may be activated based on input received from a user. In some cases, the display can be automatically activated where the processing performed by the wearable device, remote processing device or cloud server generates an alert for the user, such as an indication of fatigue, dehydration, or potential injury.

The display may also provide summary information to a user regarding a completed activity. In some cases, historical records stored on a remote processing device or cloud server can be displayed to a user to illustrate progress trends in the user's activity and physiological response.

Figure 6:
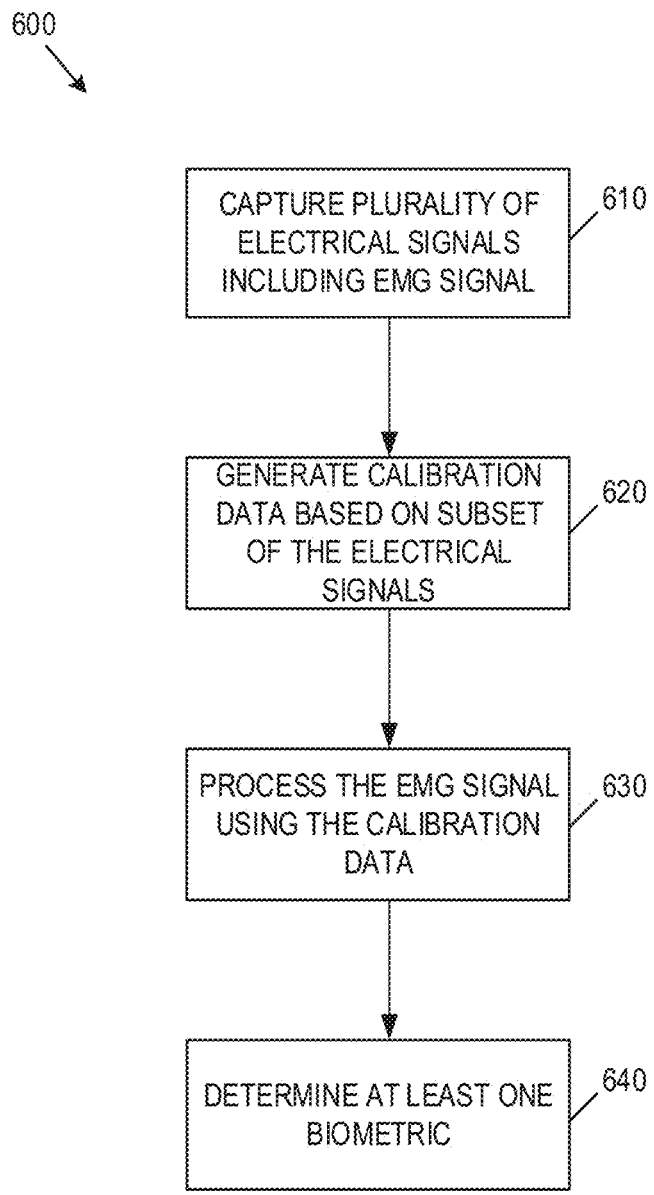
FIG. 6 is a flowchart illustrating an example embodiment of a method for activity tracking.

Referring now to FIG. 6, shown therein is a flowchart illustrating an example embodiment of a method 600 for biometric tracking. Method 600 can be performed using components of system 100 and wearable devices 102 and 300 in which electrodes and a signal acquisition unit are provided.

At 610, a plurality of electrical signals, including at least one EMG signal, are captured using the electrodes on the wearable device. The signals can be digitized by an A/D converter of the signal acquisition unit and provided to the controller on the wearable device. As mentioned above, in some cases the signals may be amplified prior to being digitized. As well, the signals may be provided to the controller unfiltered such that all filtering of the acquired signals is performed after digitization.

In some cases, the plurality of electrical signals can include skin impedance signals or bio-impedance signals. In some cases, skin impedance signals can be acquired using two electrodes positioned on the user's skin surface. For example, a small current signal can be injected into the user's skin surface using a first electrode of an electrode pair (e.g. electrode 406A) and received by a second electrode of the electrode pair (e.g. electrode 406B). In some cases, the electrodes in the electrode pair can be positioned nearby (e.g. within −1 cm) to one another to maximize the conduction that occurs through the user's skin. The amplitude of the signal received by the second electrode may be compared to the amplitude of the injected signal to calculate the impedance of the user skin surface. The phase of the received signal may also be compared across differing frequencies.

Bio-impedance signals can be acquired by measuring signals using a tetrapolar electrode configuration. A signal can be injected into the user's body using a first electrode pair (e.g. 406A and 406B). The signal received by a second electrode pair (e.g. 406C and 406D) can be measured. A comparison of the injected signal to the received signal can be used to determine bio-impedance for the user.

In some cases, the electrode pairs can be positioned at far apart locations on the user skin surface, such as cross-body or at opposite ends of a limb such that skin conduction in negligible. This may also provide an indication of the user's bio-impedance that is more representative of the hydration levels throughout the user's body, rather than in a localized region. In some cases, the electrodes may be placed on the same limb, such as a first electrode pair on the front of a user's thigh and a second electrode pair on the back of the user's thigh.

To acquire both the bio-impedance signal and the skin impedance signal, a similar process can be used. In each case, an AC injection signal can be generated, e.g. a 50 kHz signal. The injection signal can be current limited (e.g. less than 1 mA) to prevent a build-up of capacitance. A multiplexer configuration, such as the configuration described above with reference to FIG. 4B, can be used to route the injection signal to a first electrode (in the case of skin impedance sensing) or to a first electrode pair (in the case of bio-impedance sensing).

The impedance signal received by the second electrode (or electrode pair) can be provided as an input to a differential amplifier. As well, the injected signal can be tapped to the differential amplifier. The output of the differential amplifier can be fed into a full wave rectifier module which removes the AC component of the differential amplifier output signal to obtain a root mean square (RMS) value of the output signal. The RMS value can be passed through a low pass filter to obtain a DC voltage level. The DC voltage level can be used to determine the magnitude of the impedance signal.

In other cases, an inphase/quadrature (I/Q) demodulator can be used to determine impedance. An injection signal can be generated and injected to the user skin surface using a first electrode (for skin impedance) or first pair of electrodes (for bio-impedance) as described above. An impedance signal can then be acquired using a second electrode (skin impedance signal) or second pair of electrodes (bio-impedance signal) as described above. The impedance signal can be provided to a differential amplifier, and the differential amplifier output signal can be provided to the inphase/quadrature demodulator. The in-phase and quadrature components of the voltage can then be extracted from the amplified voltage signal.

An oscillator can be used to demodulate the amplified voltage signal. The oscillator source signal can be configured to correspond to the generated injection signal. That is, the oscillator in-phase signal can have the same frequency and phase as the injected signal. An oscillator quadrature phase signal can then be generated by delaying the in-phase signal by 90°. The in-phase and quadrature phase oscillator signals can be switched and fed to a mixer.

The mixer can combine the in-phase and quadrature phase oscillator signals with the amplified voltage signal to generate in-phase and quadrature phase voltage signals respectively. Each of the in-phase voltage signal and the quadrature voltage signal can be passed through a low pass filter to obtain DC values for the in-phase and quadrature signals. These signals can then be used to determine the real and imaginary components of the impedance.

At 620, calibration data is generated based on a subset of the electrical signals acquired at 610. For example, the plurality of electrical signals acquired at 610 may include one or more skin impedance signals and/or one or more bio-impedance signals. The calibration data can be generated based on acquired skin impedance signals to account for changes in the EMG signal that may be caused by changes in the conductivity of the user's skin surface. As described above, in different embodiments the calibration data may be determined by any one or more of the wearable device, remote processing device or cloud.

At 630, the calibration data is used to process the EMG signal using the calibration data. As mentioned, the calibration data may account for changes in conductivity of the skin surface that affect the EMG signals acquired at 610.

At 640, at least one biometric is determined from the processed EMG signal. For example, the biometric may be one or more of muscle intensity, muscle coordination, muscle ratio and muscle fatigue for targeted muscles. In some cases the biometrics may be determined from analyzing the EMG signal in combination with additional sensor information such as motion data or bio-impedance data, for example.

Once the at least one biometric has been determined at 640, additional biometrics and other metrics may also be determined in a similar manner as described in methods 500 and 600, for example. The at least one biometric may then be stored or displayed as described above at 550 of method 500.

Figure 7:
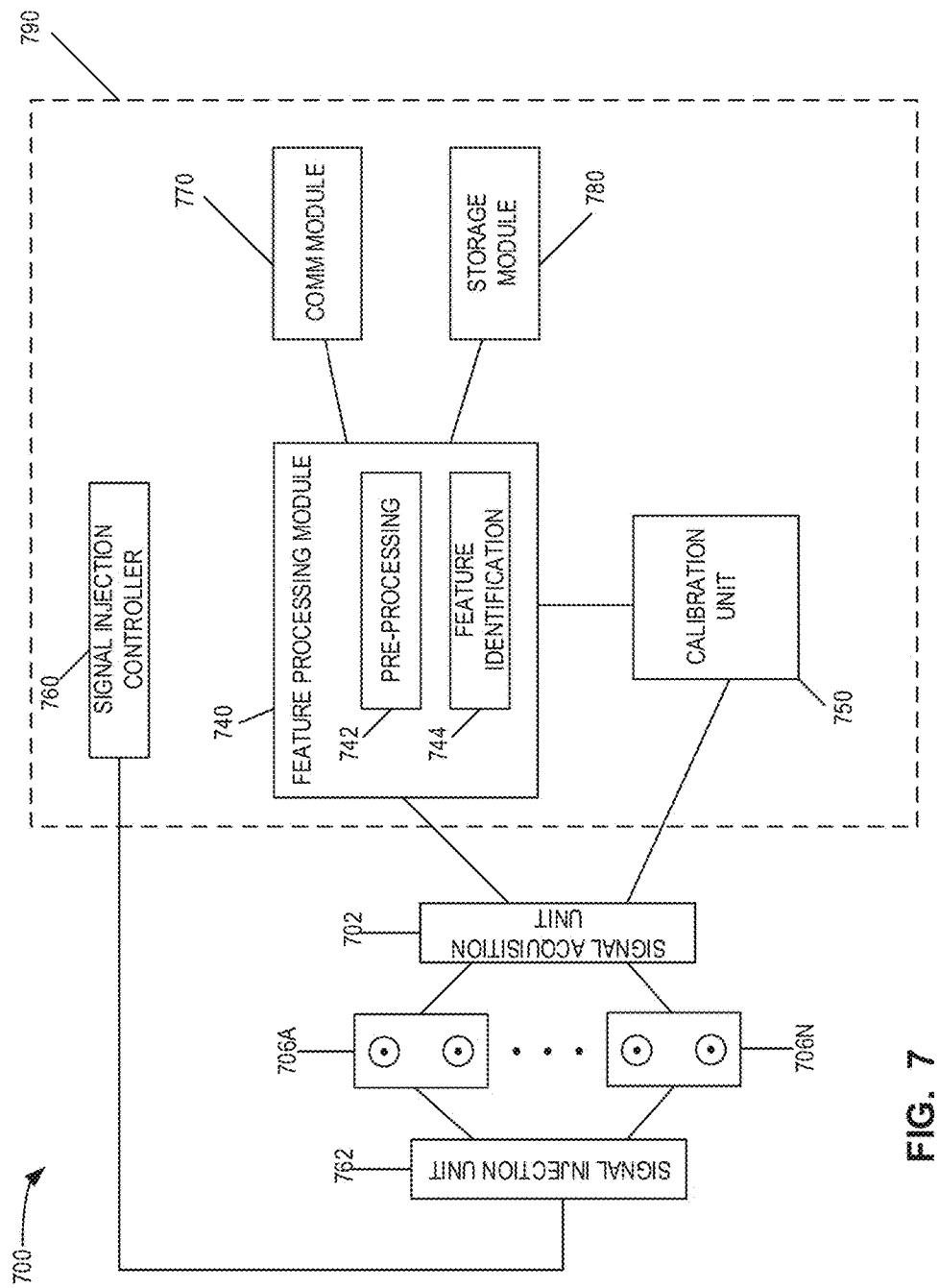
FIG. 7 is a block diagram illustrating various components used to acquire and process bio-signals in an example embodiment of the activity tracking system of FIG. 1.

Referring now to FIG. 7, shown therein is a diagram illustrating various components of system 700 that can be used to acquire and process electrical bio-signals, for example as described with reference to FIG. 6.

Generally, system 700 includes a wearable device that is generally analogous to wearable devices 200 and 300, and which includes a plurality of electrodes 706a-706n positioned to acquire an electrical signal from a user skin surface when the wearable device is secured to the user skin surface. The electrodes 706 are coupled to a signal acquisition unit 702 and a signal injection unit 762. Signal acquisition unit 702 may correspond generally to the signal acquisition unit described herein with reference to FIGS. 3 and 4.

The system 700 may also include a processing module 790. The various components of processing module 790 can be distributed between a wearable device, remote processing device and cloud server in different embodiments. Processing module 790 includes a calibration unit 750, a feature processing module 740, one or more communication module 770, one or more storage modules 780 and a signal injection controller 760.

Signal acquisition unit 702 is operatively coupled to the calibration unit 750 and the feature processing module 740. Feature processing module 740 includes a pre-processing unit 742 and a feature identification module 744. Signal acquisition unit 702 may acquire electrical signals using the electrodes 706 and digitize the acquired signals as described herein. These signals may then be provided to the calibration unit 750 and/or the feature processing module 740 for further processing.

In some embodiments, one or both of the feature processing module 740 and the calibration unit 750 may be provided on the wearable device itself. In other embodiments, the feature processing module 740 and the calibration unit 750 may be located on a remote processing device or cloud server, and the digitized signals may be communicated without any processing from the wearable device to the feature processing module 740 and calibration unit 750 using one of the communication modules 770. In some cases, aspects of the feature processing module 740 and the calibration unit can be distributed among the wearable device, remote processing device and cloud server.

For example, signal acquisition unit 702 may acquire digitized skin impedance signals provide these to the calibration unit 750. The calibration unit 750 may generate or update calibration data based on the received signals. The calibration data can then be provided to the feature processing module 740 for use in processing the acquired signals and identifying various biometrics from the acquired signals. In some cases, the calibration unit 750 may also use pre-processing unit 742 to pre-process the received signals to remove noise and other undesired signal components before generating the calibration data.

Generally, the pre-processing unit 742 can be used to remove undesirable signal components from the received digital signals. In some embodiments, the pre-processing unit 742 may also be used to calibrate the received digital signals using the calibration data generated by the calibration unit 750.

The feature identification module 744 can be used to analyze the received electrical signals (and other sensor signals) to identify at least one biometric for the user. In some cases, the feature identification module 744 can be used to determine a plurality of biometrics and other metrics for the user. The feature identification module 744 may also be used to analyze trends and provide feedback and alerts to a user based on the analysis.

Skin conditions, such as perspiration, and other constantly changing environmental factors can impact the strength and other properties of the EMG signals. Calibration data can thus be used to enable reliable comparison between EMG signals acquired throughout the performance of an activity, and over time as these parameters change.

Signal injection controller 760 may be used to generate and provide precursor signals used in acquiring a skin impedance signal and/or a bio-impedance signal. Signal injection controller 760 may inject small electrical pulses into particular electrodes 706 using signal injection unit 762. The corresponding electrical signals received at other electrodes 706 can be analyzed to determine features such as skin impedance and bio-impedance, as discussed above.

For example, the relative amplitude of the received signals can be compared with the amplitude of the injected signals. This can be used to generate calibration data, which can in turn be used to process the EMG signals and determine various biometrics. For example, hydration may be determined by analyzing a bio-impedance signal acquired from an injected electrical pulse. Hydration may be determined in various ways, such as using existing hydration vs. bio-impedance models, lookup tables, or trained machine learning models.

Signal injection controller 760 may also be used to detect when one or more electrodes 706 have become disconnected or are not in contact with a user skin surface. By detecting an open circuit in an electrode 706, system 700 may determine that the electrode has lost contact either with the user skin surface, or has become disconnected from the wearable device. Accordingly, an alert may be provided to the user indicating that the lead has been disconnected.

In some embodiments, it may be desirable to supplement biometric data acquired from electrodes proximate to the user's skin with other data, such as motion or position data. In still other embodiments, electrodes may not be provided and therefore only motion or position data may be available. Nevertheless, in such embodiments it may still be desirable to recognize or identify a specific activity being performed by the user. Recognition of the specific activity may provide additional insights into the data acquired from the electrodes, or may be used independently to measure other metrics, such as activity type.

In at least some of the described embodiments, user activity can be recognized and distinguished from other activities using data from an accelerometer sensor.

In particular, some of the described embodiments facilitate recognition and distinguishing of activity based on data from a three-dimensional accelerometer sensor of a wearable device.

Conventionally, distinguishing between different activity types on a wearable device can be challenging, because the sensors are mounted locally and are affected significantly by their orientation as well as adjacent joints and muscles. Furthermore, wearable devices are typically small in size and lightweight, and do not have significant processing capability compared to a laptop or desktop computer, for example.

The described embodiments provide activity recognition and are capable of being performed even using the limited processing capability of a wearable device. Two example embodiments are described below, however other variations are possible.

In a first example embodiment, here called a "feature-based" approach, various values and statistical features can be extracted from input signals from the accelerometer, and projected onto a space that is selected to facilitate better segregation of data points that correspond to different activity types. Classifiers can then be used to identify the regions in this projected space in which the data points fall, and thereby distinguish between the different activity types. Generally, in such embodiments, accelerometer data is collected during different activities, and first pre-processed to reduce the effects of noise. Features are extracted from a moving window of the data, and are projected onto the space that separates the activity classes the most or at least better than unprocessed data. Finally, classifiers are trained and used on this space.

In another example embodiment, here called a "model-based" approach, a generative model is trained for each activity type. After training, the generative model is capable of capturing the temporal and spatial characteristics of each activity type. Different activity types can be distinguished by identifying similarities between the input data with the generative models.

Figure 8A:
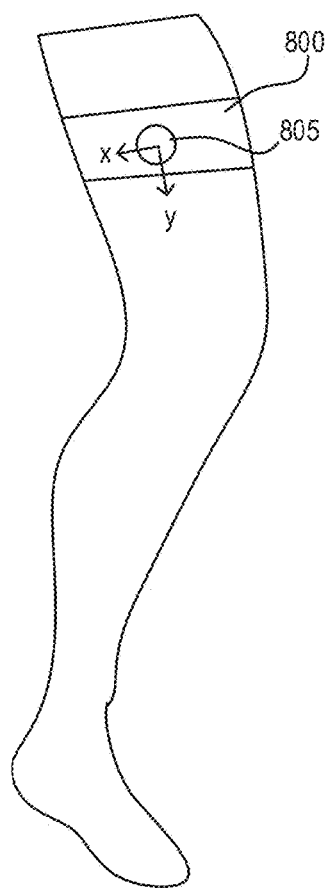
FIGS. 8A and 8B are side and front views, respectively, of a user's leg illustrating an example positioning of a wearable device.
Figure 8B:
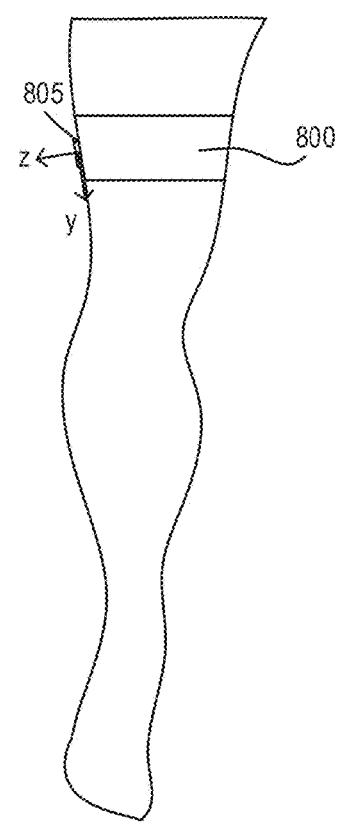

Referring now to FIGS. 8A and 8B, there are illustrated side and front views of a wearable device 800 positioned on the leg of a user. Wearable device 800 is generally analogous to wearable device 200 and 300 as described herein, and includes an IMU with an accelerometer 805. Although shown here as positioned on a leg, in other embodiments, wearable device 800 may be positioned on different limbs or body portions.

As shown in FIGS. 8A and 8B, the accelerometer 805 may be positioned laterally along the limb, so as not to interfere with an ordinary range of motion. In other embodiments, accelerometer 805 may be positioned elsewhere along the limb.

As shown, a coordinate space for accelerometer 805 is chosen such that a positive x-axis extends in an anterior direction, the positive y-axis extends in an inferior direction and the positive z-axis extends in a lateral direction relative to the user's body. Other coordinate spaces and orientations may also be used with suitable modification of the described embodiments.

Figure 9:
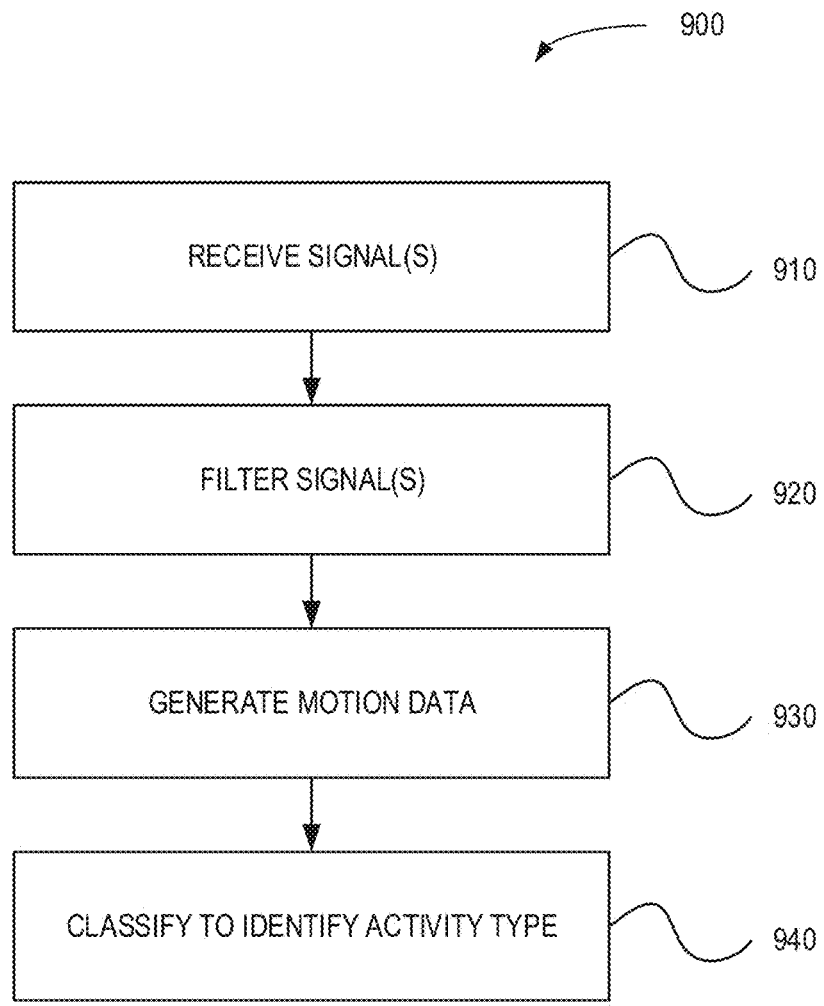
FIG. 9 illustrates an example process for analyzing activity of a user's body using a wearable device positioned on a user's limb.

Referring now to FIG. 9, there is illustrated an example process for analyzing activity of a user's body using a wearable device positioned on a user's limb. Process flow 900 may be carried out using a wearable device provided with an accelerometer as described herein.

Process flow 900 begins at 910, with a wearable device receiving a plurality of signals from at least one sensor, e.g., accelerometer, of the wearable device. The plurality of signals generally comprises at acceleration signals for at least one axis and generally at least three axes (e.g., x-, y- and z-axis). In some embodiments, the plurality of signals may also include gyroscope signals, magnetometer signals, electromyography signals, as described herein.

At 920, each of the plurality of signals may be initially filtered to generate a plurality of filtered signals. For example, the plurality of signals may be low-pass filtered to remove noise. In some cases, the plurality of signals may also be high-pass or band-pass filtered to remove undesired signal components. Specific examples of filtering are described with reference to FIGS. 10 and 11.

At 930, a controller of the wearable device generates motion data from the plurality of filtered signals.

Motion data includes processed (e.g., filtered) signals received from, for example, an IMU 322, along with derivations from the filtered signals, such as velocity and position signals, mean, standard deviation, maximum, minimum and the like.

In some alternative embodiments, a different processor, such as a remote processing device processor or a cloud server processor, may receive the plurality of filtered signals via wired or wireless communication and may generate the motion data from the plurality of filtered signals.

At 940, the motion data may be classified to identify activity type. Examples of classification approaches are described with reference to FIGS. 10A and 11A.

Figure 10A:
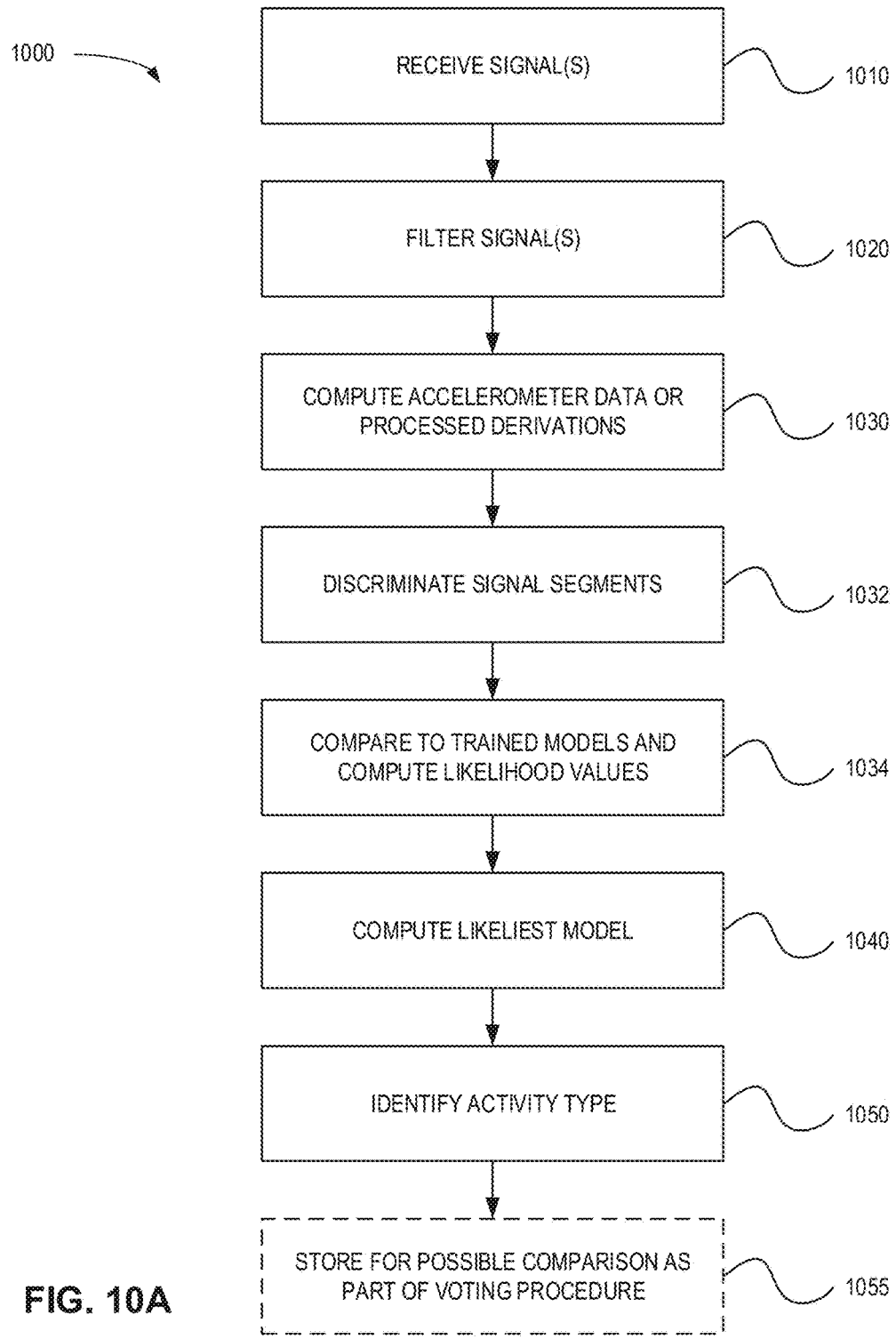
FIG. 10A illustrates another example process for analyzing activity of a user's body using a model-based approach.

Referring now to FIG. 10A, there is illustrated an example process for analyzing activity of a user's body using a wearable device positioned on a user's limb. Process flow 1000 is an example embodiment of process flow 900, and may be carried out using a wearable device provided with an accelerometer as described herein.

Process flow 1000 is an example of a model-based approach. Initially, the plurality of acceleration signals are processed to compute position signals. Optionally, the acceleration signals may be filtered or smoothed to remove noise before further processing. To improve performance, the position signals may be segmented to identify repeated or quasi-periodic signal patters which may correspond to repetitions of an activity (e.g., steps, cycling repetitions).

Figure 10B:
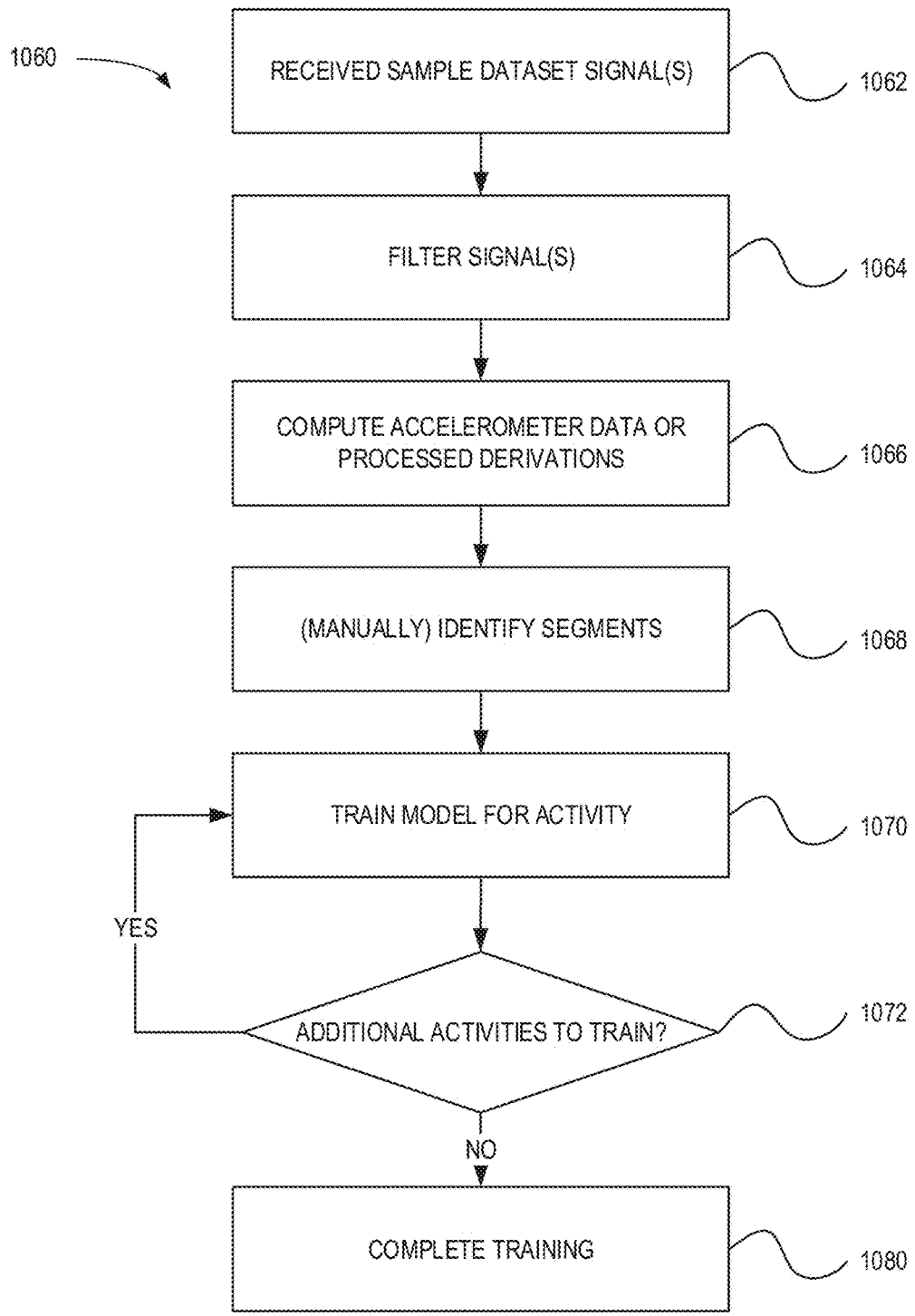
FIG. 10B illustrates an example process for training models for use in the process of FIG. 10A.

Pre-trained generative models, for example those that can be generated using the process described with reference to FIG. 10B, are then used. In the described example, Hidden Markov Models (HMM) are used.

Process flow 1000 begins at 1010, with a wearable device receiving a plurality of signals from at least one sensor, e.g., accelerometer, of the wearable device. The plurality of signals includes an acceleration signal for at least one axis and generally signals for at least three axes (e.g., x-, y- and z-axis). In some cases, the plurality of signals may include other signals, such as gyroscopic signals, magnetometer signals, electromyography signals, and the like.

Acceleration signals received from the sensors contain information about the motion being performed. In particular, the shape of the acceleration signals over time is characteristic of the motion being performed, and each individual's strategy/technique may be observed in the acceleration signals.

The acceleration signals may be affected by environmental noise and local vibrations of the sensor. To reduce the effects of environmental noise, filtering may be performed at 1020. For example, a moving average filter may be applied to each acceleration signal (for each axis of the accelerometer):

$$acc(t) = \frac{1}{2N+1}\left(\sum_{j=t-N}^{t+N} acc_{raw}(j)\right)$$

where $acc_{raw}(j)$ is the signal data collected from the sensors at time j, acc(t) is the moving average result for time t, and N is the window length of the moving average filter. Other types of low-pass filtering may also be performed in addition to, or in lieu of the moving average filter.

One example of a raw acceleration signal is shown in FIG. 14A. A corresponding pre-processed acceleration signal is shown in FIG. 14B.

Next, position signals may be computed at 1030. To compute the position signals, the DC component of the acceleration signals may be removed:

$$acc_{zm}(t) = acc_{raw}(t) - \frac{1}{2N+1}\left(\sum_{j=t-N}^{t+N} acc_{raw}(j)\right)$$

where $acc_{zm}(t)$ is the zero mean output at time t, $acc_{raw}(t)$ is the sensor reading at time t, and N is the width of the window and should be large enough to include at least one local maximum and one local minimum. In the example embodiments, N may be set to 1 second, however other window lengths may also be used.

An intermediate velocity signal can be obtained for each acceleration signal by integrating the zero mean acceleration data:

$$vel(t) = \int_0^t acc_{zm} dt$$

where vel(t) is the velocity at time t.

Position signals may then be computed by repeating the above-mentioned procedure for each velocity signal:

$$vel_{zm}(t) = vel(t) - \frac{1}{2N+1}\left(\sum_{j=t-N}^{t+N} vel(j)\right)$$

$$pos(t) = \int_0^t vel_{zm} dt$$

where pos(t) is the position at time t.

At 1032, a discrimination routine may be used to discriminate signal patterns or "segments" that correspond to repetitions within the activity. For example, segments may be discriminated by applying an adaptive thresholding technique. For example, a threshold may be computed as the midway point between a local maximum and a local minimum in the position signal. Alternatively, other linear or non-linear functions of mean, midean, minimum, and maximum can be used. Signal values that exceed the threshold can be identified as belonging to a segment. Signal values that fall below the threshold can be discarded. In other embodiments, the threshold may be pre-specified. In still other embodiments, the discrimination routine may be omitted, although this may diminish performance in some cases.

At 1034, the segmented (or non-segmented, if discrimination is not applied) position signals are input to a plurality of pre-trained generative models that correspond to a plurality of possible activity classes. Each of the plurality of pre-trained generative models is pre-trained using data corresponding to a unique activity class, as described with reference to FIG. 10B.

A forward algorithm, such as the Viterbi algorithm, can be used to compute the probability that the observation sequence is generated by each of the pre-trained generative models.

At 1050, the model with the largest log likelihood value can be selected. The activity class that corresponds to the selected model can be selected, that is, identified, as the current activity class.

In some cases, error can be reduced by using, for example, a voting procedure based on previously selected activity classes. Accordingly, at 1055, the selected current selected activity class can be stored in a memory, and compared to previously stored activity classes. For example, the voting procedure may compare 3 previously stored activity classes with the current activity class.

Referring now to FIG. 10B, there is illustrated an example process for training models for use in process 1000 of FIG. 10A.

Modelling signals (e.g., time series data) allows capturing the main attributes and information of a signal and representing them in a useful and compact manner. Hidden Markov Models, a type of generative model, are described by Rabiner, Lawrence R., "A Tutorial on Hidden Markov Models and Selected Applications in Speech Recognition," *Proceedings of the IEEE* 77 (2), IEEE: 257-86 (1989). HMMs are a stochastic modelling approach that characterizes the statistical properties of a signal. This modelling technique captures both temporal and spatial variability of the time series, and has been therefore applied in modelling human motion as described by Kulić, Dana, Christian Ott, Dongheui Lee, Junichi Ishikawa, and Yoshihiko Nakamura, "Incremental Learning of Full Body Motion Primitives and Their Sequencing Through Human Motion Observation," *The International Journal of Robotics Research*, SAGE Publications, 0278364911426178 (2011), and Wang, Liang, Weiming Hu, and Tieniu Tan, "Recent Developments in Human Motion Analysis," *Pattern Recognition* 36 (3), Elsevier: 585-601 (2003).

Figure 10C:
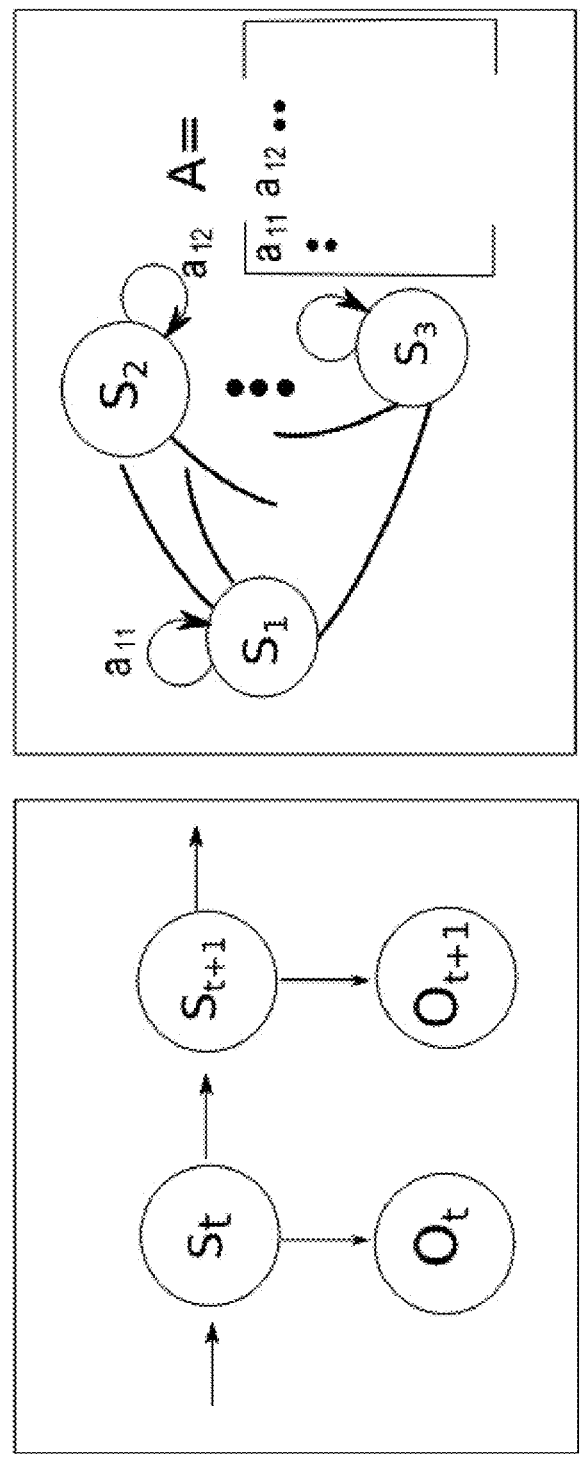
FIG. 10C illustrates an example Hidden Markov Model structure.

A HMM represents a time series signal by an evolving unobservable state variable. The state variable transitions through a discrete set of values, and the probability of these transitions is determined by a state transition matrix. At each time step the system either remains in its current state or transitions to another state. HMMs are trained on a sample dataset of signals. Where segmentation is used, the HMMs are trained on the segmented portions of the signal. An example of an HMM structure is illustrated in FIG. 10C. In the HMM structure of FIG. 10C, the signal is modelled by unobservable states (S1, S2, . . . Sn). At each timestep, the system either remains in its current state or transitions into another state with a probability.

HMMs are used as the generative models described herein. The HMMs can be trained using a training dataset obtained from multiple users, or over multiple sessions, or both, and which may include motion data such as acceleration and position signals. HMMs are generally capable of capturing the temporal and spatial variations in human motion.

Separate HMMs are trained for each separate activity class. Accordingly, each signal segment of interest is modeled by each of the plurality of HMMs, which may be used to distinguish between the activity types of walking, running and cycling.

In the example embodiments, five states are modeled: State 1 corresponds to accelerating from the initial posture (e.g., default posture); state 2 corresponds to decelerating to reach the "halfway through" posture; state 3 corresponds to reaching and remaining halfway through the posture where velocity in the z-axis becomes zero; state 4 corresponds to accelerating towards the initial posture; and state 5 corresponds to decelerating and reaching the initial posture. The observations (i.e., inputs) of the HMMs can be the position signals from a three-axis accelerometer. In some embodiments, acceleration signals themselves may also be used as observations. Based on the inputs at each timestep, the HMM either remains in its current state or transitions into another state with a probability.

Referring now to FIG. 10B, there is described an example process 1060 for training generative models (e.g., HMM) for use with process 1000 to identify activity classes.

Process 1060 begins at 1062 with the receipt of a sample dataset that can include sampled sensor signals from multiple users, or multiple sessions of users, or both.

At 1064, the signals may be filtered using an approach similar to 1020 of process 1000.

Likewise, at 1066, position signals can be computed from the filtered signals using an approach similar to 1030 of process 1000.

At 1068, the computed position signals can be analyzed, e.g., by a user, to identify signal segments in the computed position signals. The signal segments can be marked or tagged by a technician user, who may be trained to identify signal segments, and the resulting signal segments stored by the processor. In some embodiments, the signal segments may be automatically identified using segmentation algorithms. In the latter case, segments may be identified automatically, and the technician user or end user may be prompted to label or tag a corresponding activity class. The HMM can be updated accordingly.

At the same time, the activity class for each identified signal segment may also be marked or tagged.

At 1070, HMMs may be trained on signal segments corresponding to each known activity class. The process may be repeated at 1072 for each activity class that is desired to be identified. Once there are no further activity classes, training may be completed at 1080 and the HMM parameters stored for each model.

The model-based approach is described with reference to HMM generative models, however other generative models, may also be used such as Mixture of Gaussians, dynamic movement primitives and the like.

Figure 11A:
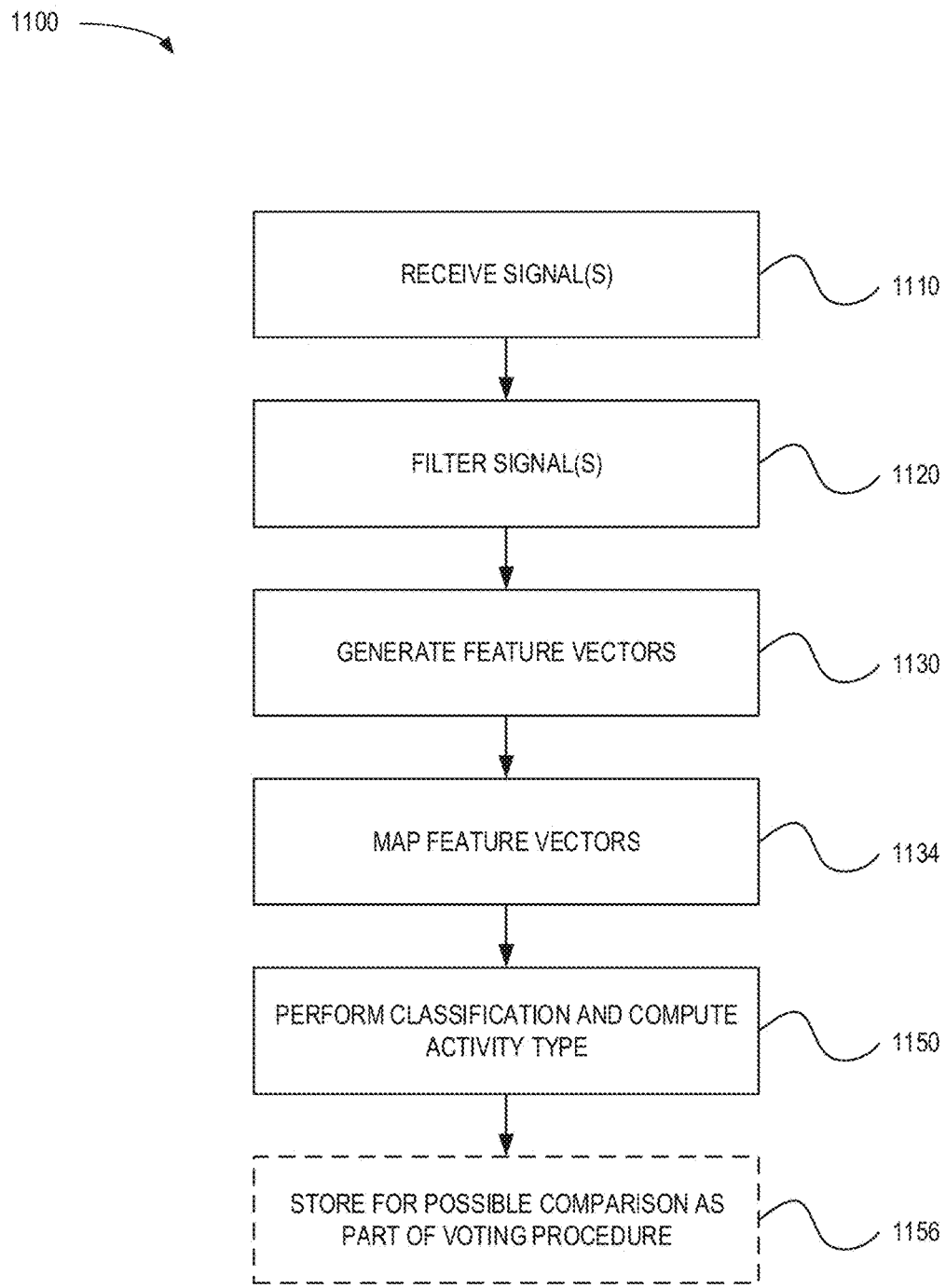
FIG. 11A illustrates another example process for analyzing activity of a user's body using a feature-based approach.

Referring now to FIG. 11A, there is illustrated another example process for analyzing activity of a user's body using a wearable device positioned on a user's limb. Process flow 1100 is an example embodiment of process flow 900, and may be carried out using a wearable device provided with an accelerometer as described herein.

Process flow 1100 is an example of a feature-based approach. In this approach, signal values and statistical features can be extracted from the plurality of acceleration signals. Feature selection or feature projection can be utilized to project or map the extracted features into a predetermined feature space, where data for each activity is more readily separable. Predetermined feature spaces may be determined as described with reference to blocks 1166, 1168 and 1170 of a process such as process 1160 of FIG. 11B. Finally, a classifier is used to determine the region of the space in which the data points are projected, and thereby the likely activity.

Process flow 1100 begins at 1110, with a wearable device receiving a plurality of signals from at least one sensor, e.g., accelerometer, of the wearable device. The plurality of signals includes an acceleration signal for at least one axis and generally signals for at least three axes (e.g., x-, y- and z-axis).

The acceleration signals received from the sensors contain information about the motion being performed. In particular, the shape, amplitude and frequency components of the acceleration signals over time is characteristic of the motion being performed, and each individual's strategy/technique may be observed in the acceleration signals.

The acceleration signals may be affected by environmental noise and local vibrations of the sensor. To reduce the effects of environmental noise, filtering may be performed at 1120.

One example of a raw acceleration signal is shown in FIG. 15A. A corresponding filtered acceleration signal is shown in FIG. 15B. Filtering may include, for example, lowpass filtering with cut-off frequency between 7-10 Hz.

At 1130, a plurality of feature vectors is generated based on the plurality of filtered signals. Each feature vector includes a plurality of feature values representative of some feature of the input signal for some time step of the filtered (or unfiltered) input signal. Each feature vector can include time domain and frequency domain data based on the plurality of filtered signals. In some embodiments, each feature vector can include values computed from other time steps, for example within a moving time window, mean, average, maximum or minimum within the window and others.

The feature vector may be defined as:

$$v_{f_t} = [f_{1_t} \ldots f_{n_t}]$$

where $f_{i_t}$ is the ith feature calculated at time t, and n is the number of features calculated at each time step. At each time step values such as mean, minimum, maximum, range, variance, Fourier transform coefficients of the accelerometer signal (e.g., the first five coefficients) and others may be computed and used as feature values of the feature vector. Signal amplitude may be represented as d. The rate of change in the accelerometer signal value, $\dot{d}$, in time window T may be computed and included in the feature vector:

$$d_W = [d_{t-T} \ldots d_t]$$

$$\dot{d}_W = [\dot{d}_{t-T} \ldots \dot{d}_t]$$

$$v_{f_t} = \begin{bmatrix} \min(d_W) & \max(d_W) & \mathrm{mean}(d_W) & \mathrm{range}(d_W) & FFT(d_W) \\ \min(\dot{d}_W) & \max(\dot{d}_W) & \mathrm{mean}(\dot{d}_W) & \mathrm{range}(\dot{d}_W) & FFT(\dot{d}_W) \end{bmatrix}$$

where $d_t$ is the data at time t, $\dot{d}_t$ is the rate of change in the data at time t, T is the window length, and FFT is the Fast Fourier Transformation.

Fast Fourier Transformations (FFT) can be computed using the following formula:

$$X(k) = \sum_{j=1}^{N} x(j)\omega_N^{(j-1)(k-1)}$$

where X(k) is the k th frequency component, N is the length of the input data x, and $$\omega_N = e^{\frac{-2\pi i}{N}}$$

is the Nth root of unity. The number of frequency components may be, for example, k=1 . . . 5.

Figure 11B:
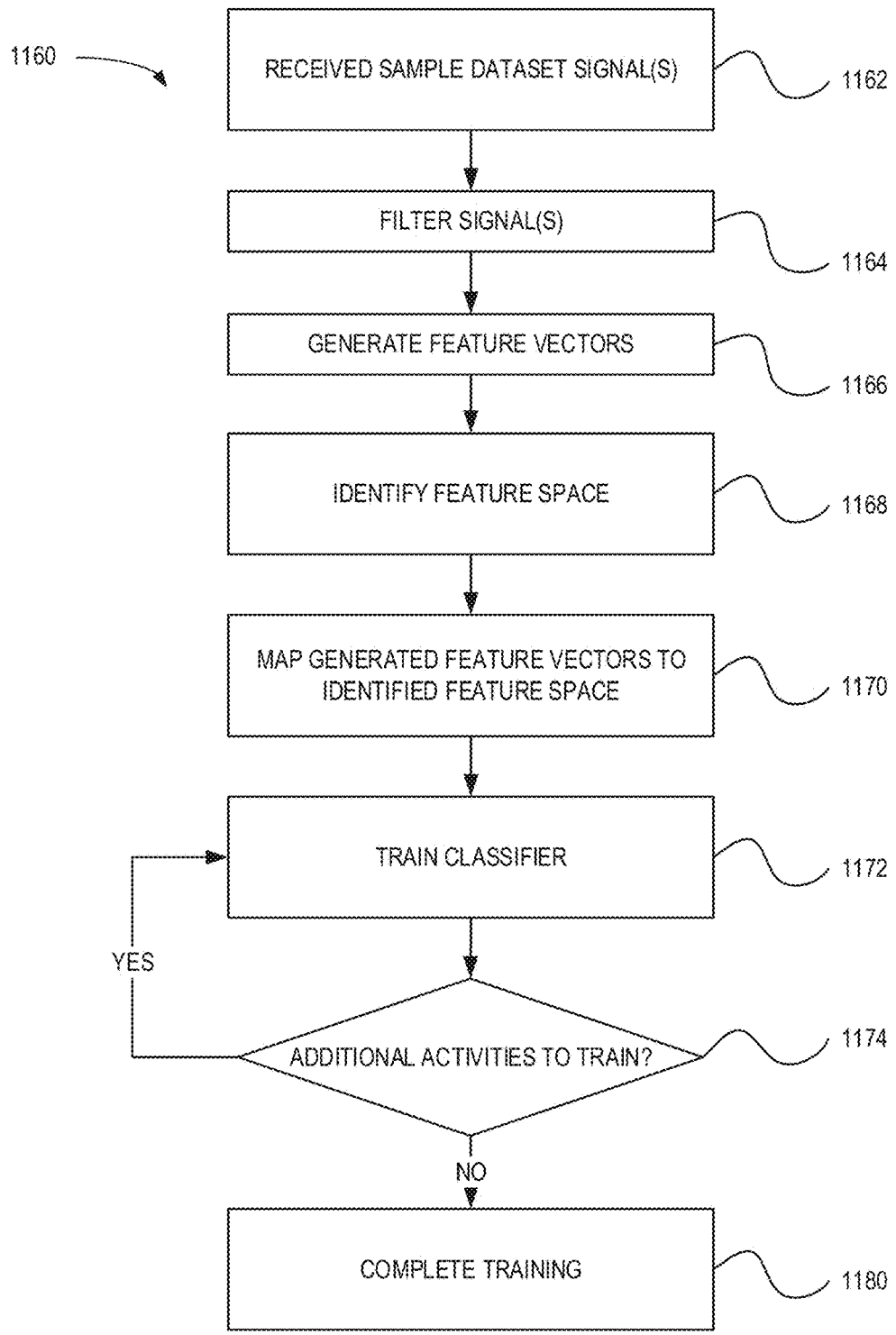
FIG. 11B illustrates an example process for identifying feature spaces for use in the process of FIG. 11A.

At 1134, the generated feature vectors are mapped onto the predetermined feature space determined, e.g., using blocks 1166, 1168 and 1170 of process 1160 of FIG. 11B. Mapping may be performed in several ways, depending on the approach used to predetermine the feature space.

In some embodiments, the generation of feature vectors at 1130 and mapping at 1134 may be merged, by computing only those feature values are required in the predetermined feature space.

Once the feature vectors have been mapped onto the predetermined feature space, classification of the feature vectors can be performed at 1150 using pre-trained classifiers. Classifiers may be trained as described with reference to FIG. 11B.

Accordingly, as described herein, the projected features of each feature vector can be computed at each time step, and the activity type computed by the hierarchical classifier.

At 1156, the selected activity type for the current time step can be compared to previously stored activity types for previous time steps. In similar fashion to the model-based approach, error can be reduced by using, for example, a voting procedure based on previously selected activity types. Accordingly, at 1156, previously stored activity types may be compared to the currently classified activity type. For example, the voting procedure may compare 3 previous activity type predictions.

In general, the predicted activity type for each time step is classified separately with the feature-based approach, while each signal portion (e.g., segment consisting of multiple time steps) is classified as a whole in the model-based approach. Regardless of whether segments or individual time samples are assessed, an overall classification of the activity type being performed need not rely solely on the current classified activity type. That is, past classification results can be taken into account and analyzed for a more accurate understanding of the activity. One approach is to average the current prediction and the previous predictions.

In some cases, however, activity types may be similar, and the feature vectors may be close to classification boundaries, resulting in a prediction sequence that toggles between the two activities. In such cases, the majority of the predictions may not provide a good indication of the original classification. In such cases, a Bayesian approach may be employed in place of a majority voting procedure. The Bayesian approach may aggregate the classification results over multiple time steps or segments. A Naïve Bayes classifier, or other classifiers such as Support Vector Machines, K-Nearest Neighbour, Artificial Neural Networks and Hidden Markov Models, can be trained to make the classification.

Referring now to FIG. 11B, there is described an example process 1060 for determining feature spaces and training classifiers to identify activity types, for use with process 1100.

Process 1160 begins at 1162 with the receipt of a sample dataset that can include sampled sensor signals from multiple users, or multiple sessions of users, or both.

At 1164, the signals may be filtered using an approach similar to 1120 of process 1100.

Likewise, at 1166, position signals can be computed from the filtered signals using an approach similar to 1130 of process 1100.

Because a high-dimensional feature vector can cause over-fitting, a predetermined feature space can be selected at 1168 to reduce the dimensions of the feature space, and thereby allow selecting the features that are best suited to distinguishing activity class or activity type.

Feature selection and feature projection are two approaches that can be used to reduce the dimension of the feature space and allow selection of features that facilitate classification.

The dataset of sample data obtained at 1162 may be analyzed and feature vectors computed as at 1130 of process 1100.

The resulting feature vectors can be provided in a matrix $D_f$ of feature vectors $v_f$, which includes multiple features for different time samples and different activity classes or types. An output matrix $L_f$ may be provided, which contains an activity class or activity type that is known a priori for each feature vector $v_f$ in the sample dataset $D_f$.

In one approach, an Analysis of Variance (ANOVA) as described by Gelman, Andrew, "Analysis of Variance—Why It Is More Important Than Ever," *Annals of Statistics* 33 (1): 1-53 (2005) can be used. ANOVA can determine the most informative (e.g., distinguishing) features of a feature set. In particular, ANOVA determines the probability that a particular feature in a plurality of feature vectors (e.g., mean) is generated from the same distribution. The smaller this probability value is, the more likely it is the feature under consideration originates from a different activity type than the reference feature(s) for a particular activity type. When an individual feature (e.g., mean) has a small probability for a given reference feature, it can be inferred that the particular feature will be a useful comparator for separating activity types (as compared to other features with a higher probability value across all activity types).

For example, the following procedure can identify the most discriminant features:

$$F_i = [f_{i_t}], t = 1 \ldots N$$

$$p_i = anova(F_i)$$

$$F_S = \arg \min_F p_i$$

where $F_i$ is the matrix of all the available samples of the feature $f_i$ in the training set, N is the number of available samples, $p_i$ is the probability value calculated for each feature separately using ANOVA, and $F_S$ are the features with the smallest probability p.

In training, ANOVA can be applied to the different activity types (or classes) simultaneously. The features identified using ANOVA analysis can be determined as the best distinguishing features for the various activity types. As described with reference to 1130 and 1134 of process 1100, other features subsequently can be discarded or not computed at all. For example, if ANOVA analysis identifies mean, variance, first and third Fourier transform coefficients as distinguishing features, then these may form the common feature space used for classification. Conversely, the second Fourier transform coefficient may be discarded and other features, such as maximum or minimum values, need not be computed at all.

Figure 16A:
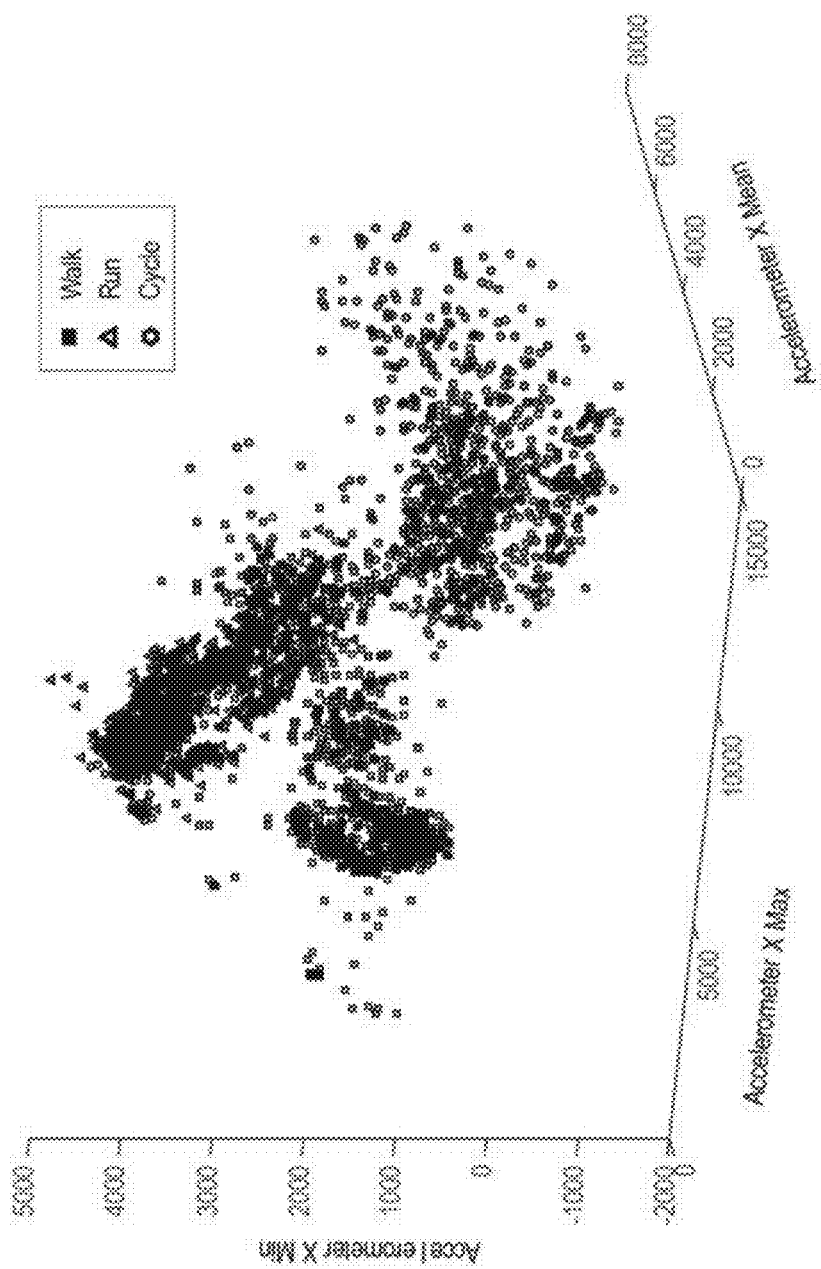
FIGS. 16A and 16B illustrate example datasets mapped into projected feature spaces in accordance with the process of FIG. 11A.

FIG. 16A illustrates an example dataset mapped into a projected feature space created using an ANOVA approach. Specifically, feature vectors from the example dataset were projected into a three-dimensional space derived using ANOVA. The activity type of each feature vector is identified by the marker in the plot 1600. Three different activity types were used, with three different markers applied in plot 1600 (i.e., square, triangle and hexagon). The separability of the data in the projected feature space can be seen clearly.

As an alternative to ANOVA, a Principal Component Analysis (PCA) may be used, as described by Smith, Lindsay I, *A Tutorial on Principal Components Analysis* (2002). PCA is an unsupervised approach for feature projection. Under PCA eigenvalues and eigenvectors are computed of a covariance matrix for a dataset. The eigenvectors are sorted based on eigenvalues in a descending manner. Each eigenvector can form the basis of a new dimension, onto which the dataset can be projected. Those dimensions which exhibit the most variant directions (e.g., the largest eigenvalues) in the dataset can be selected as the bases of a projected space. Other dimensions can be discarded to reduce data needs and computational complexity.

When training, the bases of the new projection space can be found as follows:

$$V = eig(cov(D_f - \overline{D}_f))$$

$$\tilde{D}_f = D_f \times sorted(V)$$

where $\overline{D}_f$ is the mean of data set $D_f$, $\tilde{D}_f$ is the projection of $D_f$ onto the new space and sorted(V) contains the sorted eigenvectors such that the eigenvectors corresponding to higher eigenvalues are ordered first.

In the example embodiments, PCA is applied to training data resulting in a feature space (i.e., projection space) generated using the first three dimensions identified as most variant. Once the predetermined feature space is found, the transformation can be performed on the streaming data to map the incoming data onto the predetermined feature space.

Figure 16B:
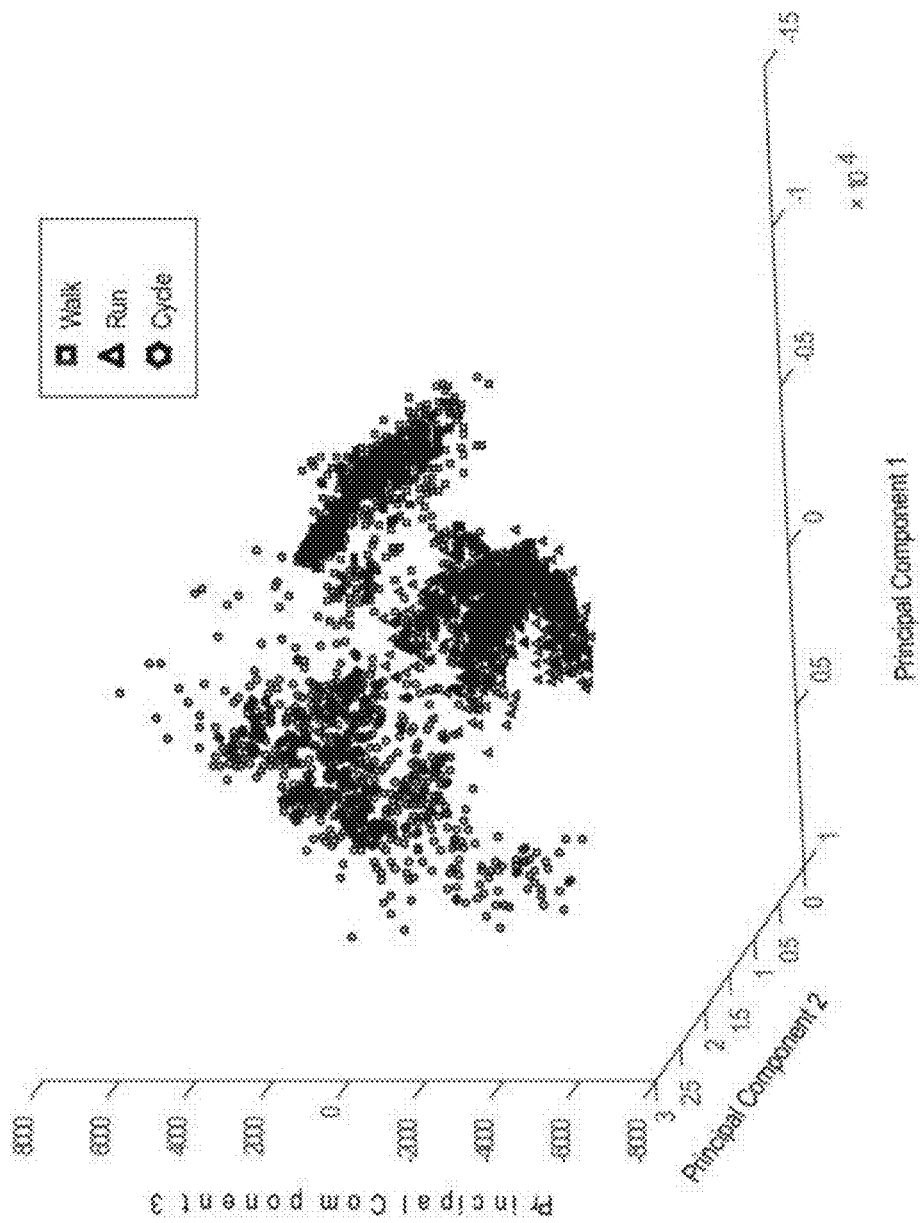

FIG. 16B illustrates an example dataset mapped into a projected feature space created using a PCA approach. As with ANOVA, feature vectors from the example dataset were projected into a three-dimensional space derived using PCA. The activity type of each feature vector is identified by the marker in the plot 1600. Three different activity types were used, with three different markers applied in plot 1600 (i.e., square, triangle and hexagon). The separability of the data in the projected feature space can be seen clearly.

Once each feature space has been determined, the feature vectors may be mapped onto the determined feature space at 1170.

Next, classifiers may be trained for distinguishing activity types in the feature space at 1172.

A hierarchical classification approach can be used as described above. Generally, each classifier can be trained to compare a single activity type to all remaining activity types. The preferred feature space for this binary comparison between a first activity type and remaining activity types is found for the training dataset. The process may be repeated at 1174, until enough classifiers have been trained to classify each activity type, whereupon the process may complete at 1180. Accordingly, at each level of the hierarchical classifier, a binary classifier is trained to separate one action from the remaining actions in the trained feature space. The sample data corresponding to the first activity type is removed from the data set, and additional feature spaces are identified for additional activity types in similar fashion. The procedure is repeated until the optimal feature space to separate the second activity from the remaining activities is found in the same manner, and the second layer's classifier is trained on this feature space. This procedure continues until a classifier has been trained for all for all activity types.

Figure 12:
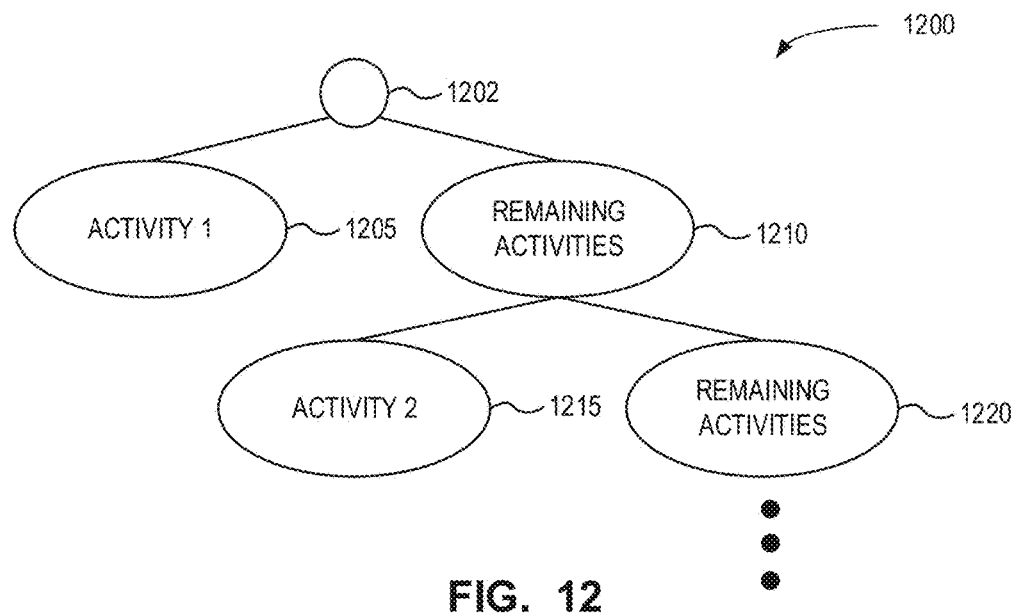
FIG. 12 illustrates an example hierarchical classification approach usable with the process of FIG. 11A.

FIG. 12 illustrates an example hierarchical classification approach. As shown, a first comparison is made at node 1202, which classifies between a first activity type 1205 and remaining activity types 1210. Next, a second comparison is made between remaining activity types 1210 and activity type 1215. Additional comparisons can be made sequentially thereafter.

Several classifier types are suitable for hierarchical classification. For example, Support Vector Machines (SVM) and Naïve Bayes (NB) classifiers can be used.

SVMs construct a half space in any dimension n, which can be used for the purpose of classification, or regression. In the example embodiments, a soft margin is employed so that in the absence of a hyperplane that can perfectly separate the data, the classifier will choose a hyperplane that maximizes the possibility of separating the data while still minimizing error.

When training the SVM, the matrix $D_f$ includes the projected features and $L_f$ includes the corresponding activity types of the data suitable for the binary classification at each level of the hierarchical classifier. The SVM is trained at each level of the hierarchical classifier using a dataset, to separate one activity type from all of the remaining activity types.

In a Naïve Bayes classifier, at each step, one activity type is compared to all remaining activity types. The Naïve Bayes classifier is trained on the identified feature space using the training data (e.g., at each level) to separate a particular activity type from the remaining activity types in the corresponding feature space.

Figure 13:
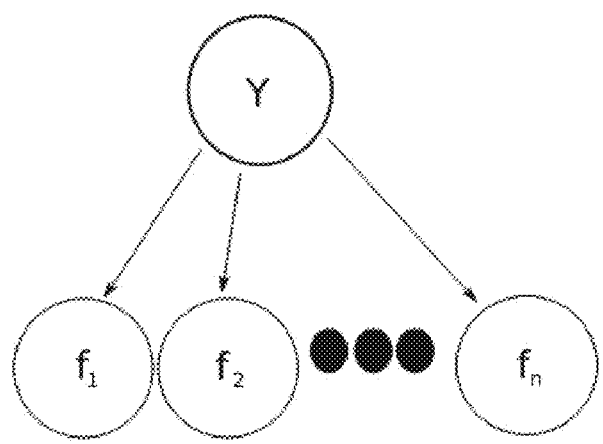
FIG. 13 illustrates another example classification approach usable with the process of FIG. 11A.

A Naïve Bayes classifier operates on the assumption that each input feature, f, is independent of the others:

$$p(f_i|f_1, \ldots, f_{i-1}, f_{i+1}, \ldots, f_n) = p(f_i)$$

$$p(y_i|f_1, \ldots, f_n) = p(y_i|f_1)p(y_i|f_2) \ldots p(y_i|f_n)$$

where p is the probability distribution, and $y_i$ is the ith output vector. The probability distribution may be a normal distribution, for example. Once the Naïve Bayes classifier is trained, each new sample point can be identified as belonging to a particular activity type. FIG. 13 illustrates a schematic model of a Naïve Bayes classifier.

In a K-Nearest Neighbour (K-NN) classifier, the K-NN classifier predicts the label of each point by utilizing the labels of its nearest neighbours in the training dataset. For example, let L(x) be the label predicted for sample x, then the K-NN classifier can be formulated as follows:

$$L(x) = \text{majority}(L(x_{K_{result}}))$$

where $X_{K_{result}}$ are the K nearest neighbour and are obtained from:

$$x_{K_{result}} = \arg\min_{\forall x_i \in Z} \|x - x_i\|$$

where Z is the training data and $\|x - x_i\|$ is the Euclidean distance between x and $x_i$. In the example embodiments, the nearest neighbour algorithm was used, with K=1, however other values can also be used. The K-NN, SVM, and NB approaches are described by Duda, Richard O., Peter E. Hart, and David G. Stork, *Pattern Classification* (2nd Edition), Wiley-Interscience, 2000.

The described example embodiments have been validated using experimental data. In one experiment, a ten-fold cross validation was performed in which 90% of a sample data set was used to train feature-based and model-based processors (i.e., "Cross Validation"). The remaining 10% of the data set was used to test the trained processors. In another experiment, sample data for multiple test subjects was used to train, and one test subject was left out of the training dataset and used to verify the trained processors (i.e., "Leave One Out").

The results of the first and second experiments are shown in Table 1:

TABLE 1

| Classifier | Projection Method | Cross Validation Accuracy | Leave One Out Accuracy |
|---|---|---|---|
| SVM | ANOVA | %83.49 ± %4.32 | %94.59 ± %6.79 |
| SVM | PCA | %81.63 ± %4.49 | %93.89 ± %7.80 |
| NB | ANOVA | %67.11 ± %7.56 | %87.78 ± %9.12 |
| NB | PCA | %68.63 ± %09.17 | %76.23 ± %29.53 |
| KNN | ANOVA | %79.99 ± %3.04 | %85.21 ± %12.39 |
| KNN | PCA | %81.27 ± %4.94 | %85.09 ± %10.67 |
| HMM | N/A | %93.75 ± %3.12 | %94.96 ± %4.41 |

As seen above, experimentation was performed for various postures when cycling. When a single accelerometer is located on the thigh of a user, cycling while standing may appear very similar to walking and running. To further validate the described example embodiments, additional data from standing cycling was obtained, and the validation repeated to produce the results shown in Table 2. It can be observed that the feature-based approach may be less accurate than the model-based approach at distinguishing standing cycling activity type.

TABLE 2

| Classifier | Projection Method | Cross Validation Accuracy | Leave One Out Accuracy |
|---|---|---|---|
| SVM | ANOVA | %41.34 ± %.8.69 | %72.74 ± %38.41 |
| SVM | PCA | %43.66 ± %.8.36 | %67.87 ± %38.7 |
| NB | ANOVA | %39.44 ± %5.19 | %68.49 ± %37.96 |
| NB | PCA | %43.21 ± %6.19 | %65.57 ± %43.93 |
| KNN | ANOVA | %45.44 ± %.4.88 | %82.15 ± 14.20 |
| KNN | PCA | %50.71 ± %.4.75 | 80.58 ± 3.10 |
| HMM | N/A | %98.63 ± %1.21 | %91.23 ± %8.85 |

Recognition of activity class or activity type represents one form of exercise metric that may be obtained. However, there are many other exercise metrics that may provide useful information to users, fitness coaches or clinicians, among others. For example, other metrics such as exercise cadence, calorie expenditure, muscle fatigue, muscle intensity, and the like can provide valuable insights to many parties.

Generally, in the field of wearable devices, such metrics have been difficult to acquire. This can be due to the device being mounted on or covering a limited part of the body, for example. Conventionally, it has been difficult for wearable devices to have a realistic understanding of the activity being performed by the user. For example, when cycling, a wrist-based activity tracker may perceive a cyclist to be stationary if the cyclist's arm maintains a constant velocity (i.e., does not accelerate), even where the cyclist is exerting effort to maintain that constant velocity. As a result, conventional wearable devices may lack accuracy. Moreover, processing power is often quite limited on such devices, requiring analysis algorithms to have low complexity and thus limiting the ability to improve accuracy.

The described embodiments generally facilitate determination of enhanced exercise metrics by considering multiple types of data. In some cases, as with activity type or activity class, these metrics may be computable from one form of data, such as acceleration signals from a wearable device. However, in other cases, the computation of these exercise metrics may take advantage of data from multiple signal types. For example, some exercise metrics may correlate accelerometer data with electromyographic data to determine the metric.

As shown in FIG. 3, a wearable device 300 can be provided with sensors or electrodes that can detect electromyographic signals. In addition, wearable device 300 may be provided with an IMU that has a 3-axis accelerometer.

In some cases, wearable device 300 can be positioned on a user's thigh, as illustrated in FIGS. 8A and 8B, for example when determining metrics related to cycling. In other cases, wearable device 300 can be positioned elsewhere on the user's body, depending on the type of metric to be determined.

Example embodiments for exercise metric computation are described herein using electromyography and accelerometer data. However, in other embodiments, additional sensors such as gyroscopes, magnetometers, extra EMG channels for different muscles, and different types of EMG sensors can also be utilized.

Figure 17:
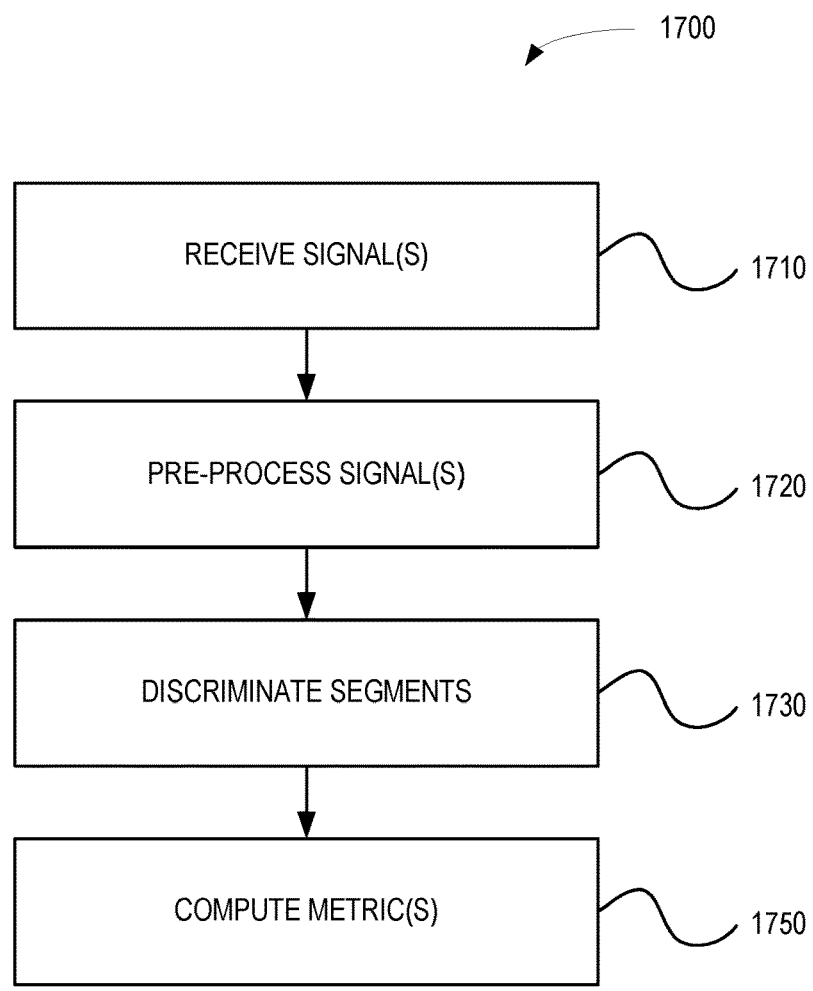
FIG. 17 illustrates an example process for computing exercise metrics using a wearable device.

Referring now to FIG. 17, there is illustrated an example process for computing exercise metrics using a wearable device positioned on a user's body. Process flow 1700 may be carried out using a wearable device, such as wearable device 300 or, in some cases, by a system such as system 100 described herein.

Process flow 1700 begins at 1710, with a wearable device receiving a plurality of signals from at least one sensor, e.g., accelerometer or EMG sensor, of the wearable device. The plurality of signals may include acceleration signals for at least one axis, or an EMG signal from at least one EMG sensor, or both. In some embodiments, acceleration signals may include several axes, such as three axes (e.g., x-, y- and z-axis).

In one example embodiment for cycling applications, where the wearable device is positioned on a user's thigh, the z-axis of the accelerometer may be oriented laterally outwardly from the user's leg (i.e., parallel to the ground) from the resting position. The x- and y-axes may be oriented towards the ground, each with a 45° angle relative to the vertical. EMG signals may be collected from the hamstring and quadriceps muscles.

Accelerometer data may be represented as:

$$D_{acc} = [D_{acc,x} D_{acc,y} D_{acc,z}]$$

where $D_{acc,x}$ is an acceleration signal vector for an x-axis of the accelerometer, comprising signal values for a given time period. Similarly, $D_{acc,y}$ is an acceleration signal vector for a y-axis, and $D_{acc,z}$ is an acceleration signal vector a z-axis. Likewise, EMG data may be represented as:

$$D_{emg} = [D_{emg,quad} D_{emg,ham}]$$

where $D_{emg,quad}$ is an EMG sensor vector for a quadriceps muscle for a given time period, and $D_{emg,ham}$ is an EMG sensor vector for a hamstring muscle.

Based on these data signals and their derivations, the described embodiments facilitate analysis of exercise metrics, such as cadence (revolutions per minute or steps per minute), speed, distance, calorie expenditure, muscle activation intensity, muscle coordination, muscle ratio, muscle fatigue, and muscle balance, activity type and others.

The vectors $D_{emg}$ and $D_{acc}$ represent time-series data (signals). These may be pre-processed at 1720 to reduce noise contribution. In some cases, pre-processing may condition the signals for further analysis.

In one example embodiment, pre-processing includes filtering to remove noise, high frequency signal components, and motion artifacts from the collected data.

For example, accelerometer signals may be low-pass filtered. Generally, the low-pass filter cut-off frequency should be chosen large enough to remove contributions not related to human motion. Generally, the cut-off frequency may be approximately 7 to 10 Hz. In one example, the cut-off frequency may be about 10 Hz.

Figure 20:
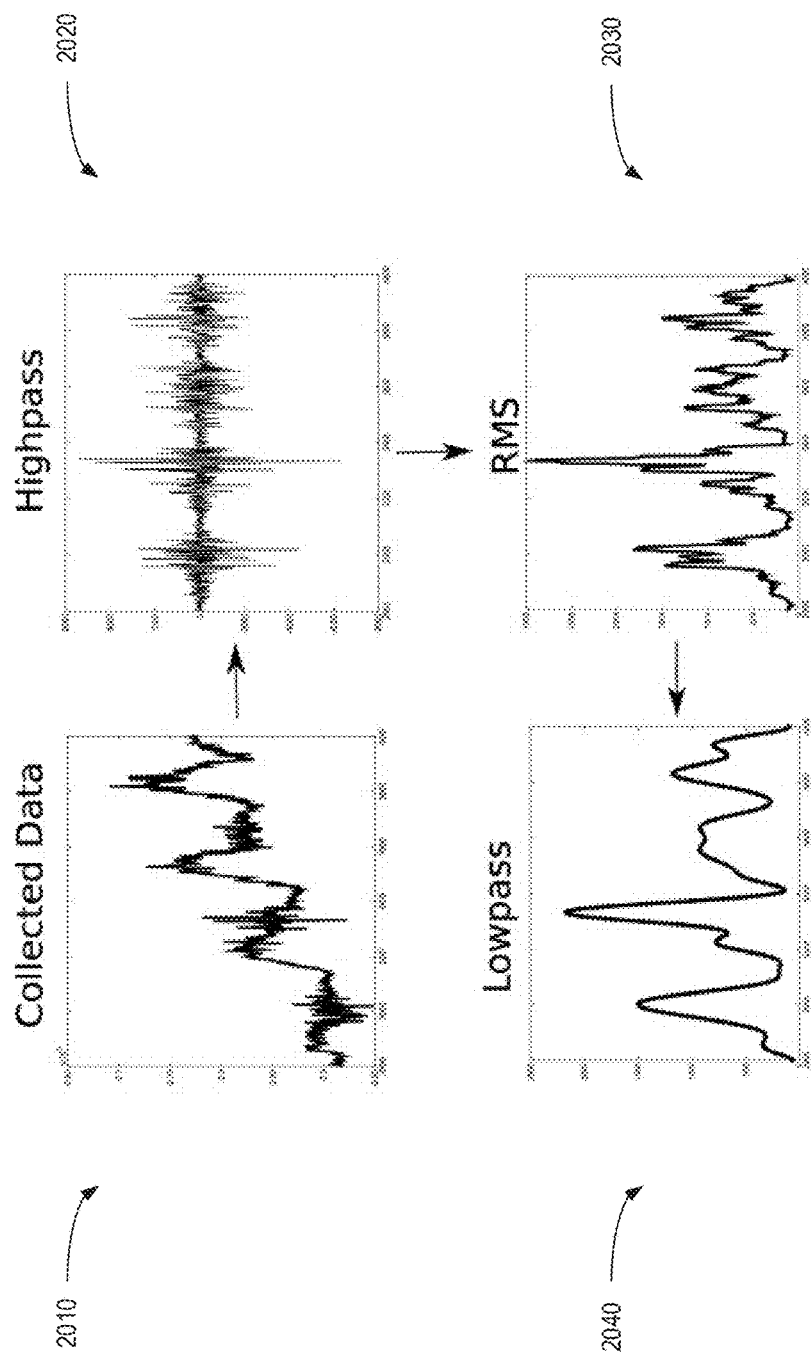
FIG. 20 illustrates example signal plots through successive filtering as in the process of FIG. 17.

EMG signals may also be pre-processed to remove motion artifacts. FIG. 20 illustrates signal plots through successive pre-processing acts. An unfiltered EMG signal is illustrated in plot 2010, in which motion artifacts are evident in the stepped nature of the signal. Motion artifacts can be filtered using a high-pass filter with cut-off frequency of a few hertz (e.g., about 3-4 Hz) to produce a first pre-processed signal as shown in plot 2020. Here it can be observed that the signals exhibit an erratic shape, which may be difficult to analyze accurately. Accordingly, after removal of motion artifacts, next a second pre-processed signal may be computed, by computing the energy of the first pre-processed signal using a root mean square (RMS) approach, to provide the signal of plot 2030:

$$EMG_{RMS}(t) = \sqrt{\frac{1}{n} v_{EMG}(t-n:t) v_{EMG}(t-n:t)^T}$$

where $EMG_{RMS}(t)$ is the RMS value of the EMG signal at time t, $v_{EMG}(t-n:t)$ is the vector of the EMG signal from time t−n to time t, and n is the width of the EMG signal considered for computing RMS value.

Finally, a third pre-processed signal may be produced by applying a low-pass filter with cut-off frequency of about 10 Hz to the second pre-processed signal, to remove high frequency components. The resulting third pre-processed signal is illustrated in plot 2040.

Some exercise metrics may use discrimination of segments in the signals at 1730. For example, signals that include a component of repetitive motion (e.g., cadence) may generate signal segments that correspond to successive periods of that repetitive action. However, not all exercise metrics may rely upon discriminating signal segments.

Signal segments can be discriminated in many ways. Two example approaches are described herein.

A first approach for signal segment discrimination employs an approach similar to the feature-based activity type recognition as described elsewhere herein. However, rather than mapping to a feature space and classifying based on an activity type directly, the mapping and classification may be trained to discriminate between active periods and inactive periods in the signal, which thereby delineates signal segments.

In particular, the discrimination task can be characterized as a two class problem, where one class contains the "active" portions of a signal segment (e.g., portions of the signal above a noise or measurement threshold), and the other class contains the "inactive" portions of a signal segment (e.g., portions of the signal below a noise or measurement threshold). In general, for metrics that use EMG data, EMG signals may be segmented to identify periods of muscle activity. Similarly, for metrics that use accelerometer-based data, accelerometer signals (or their derivations) may be segmented to identify repetitions in the signals.

To perform this classification, a set of signal attributes that separate the two classes can be identified, and this identified set of features can then be used to classify each incoming sample as active or inactive, as described by Lin, Jonathan Feng-Shun, Vladimir Joukov, and Dana Kulic, "Full-Body Multi-Primitive Segmentation Using Classifiers," In *Humanoid Robots (Humanoids), 2014 14th IEEE-RAS International Conference on*, 874-80. IEEE (2014).

The vector which contains the feature values at each time step is referred to as the feature vector:

$$v_{f_t} = [f_{1_t} \ldots f_{n_t}]$$

where $f_{i_t}$ is the ith feature value for time t, and n is the number of features computed or determined at each time step.

At each time step t, the feature vector, $v_{f_t}$ is formed from data samples, d, and the rate of change in the data samples, dd, for a window from −T to +T time around the current sample:

$$v_{f_t} = [d_{t-T}, \ldots, d_t, \ldots, d_{t+T}, \dot{d}_{t-T}, \ldots, \dot{d}_t, \ldots, \dot{d}_{t+T}],$$

where $d_{t-T}$ is the first data sample for the window, $\dot{d}_{t-T}$ is the rate of change from T time steps before the current sample. T may be a tunable parameter. For example, T may be between 5-20.

An ANOVA approach may be used to identify the most informative features of the feature set. For each set of features, ANOVA can determine the probability that the two classes, "active" signal portion and "inactive" signal portion, are generated from the same distribution. Therefore, the smaller this probability value is, the more likely it is that different sources have generated the two classes. Thus, when the probability value is small given a particular feature type, that feature type can be used to discriminate between the two classes better compared to features with larger probability values.

In the example embodiment, a pre-training may be performed, in which a feature vector may be calculated at each timestep for the training data set. For the training data set, data may be manually discriminated into active and inactive signal portions. Following ANOVA computation, the two feature types with the smallest probability compared to the rest of the features can be chosen for discrimination purposes:

$$F_i = [f_{i_t}] \; t = 1 \ldots N$$

$$p_i = anova(F_i)$$

$$F_S = \underset{F}{\mathrm{argmin}}\, p_i$$

where $F_i$ is all the available samples of the feature $f_i$ in the training set, N is the number of available samples, $p_i$ is the probability value calculated for each feature separately using ANOVA, and $top_{features}$ are the features with smallest probability p. The $top_{features}$ define the projected feature space to be used by a discrimination classifier.

To complete the discrimination, and separate the active signal portions from the inactive signal portions, a suitable classifier may be used. For example, a Naïve Bayes classifier can be used to discriminate. The Naïve Bayes classifier considers that each input feature, f, is independent of others. That is:

$$p(f_i|f_1, \ldots, f_{i-1}, f_{i+1}, \ldots, f_n) = p(f_i)$$

$$p(y_i|f_1, \ldots, f_n) = p(y_i|f_1)p(y|f_2) \ldots p(y_i|f_n)$$

where p is the probability distribution (e.g., normal distribution), and $y_i$ is the ith output vector. Once the NB classifier has been trained, each new sample can be labelled as belonging to an active or inactive signal portion. Accordingly, a plurality of signal segments can be generated.

Figure 21A:
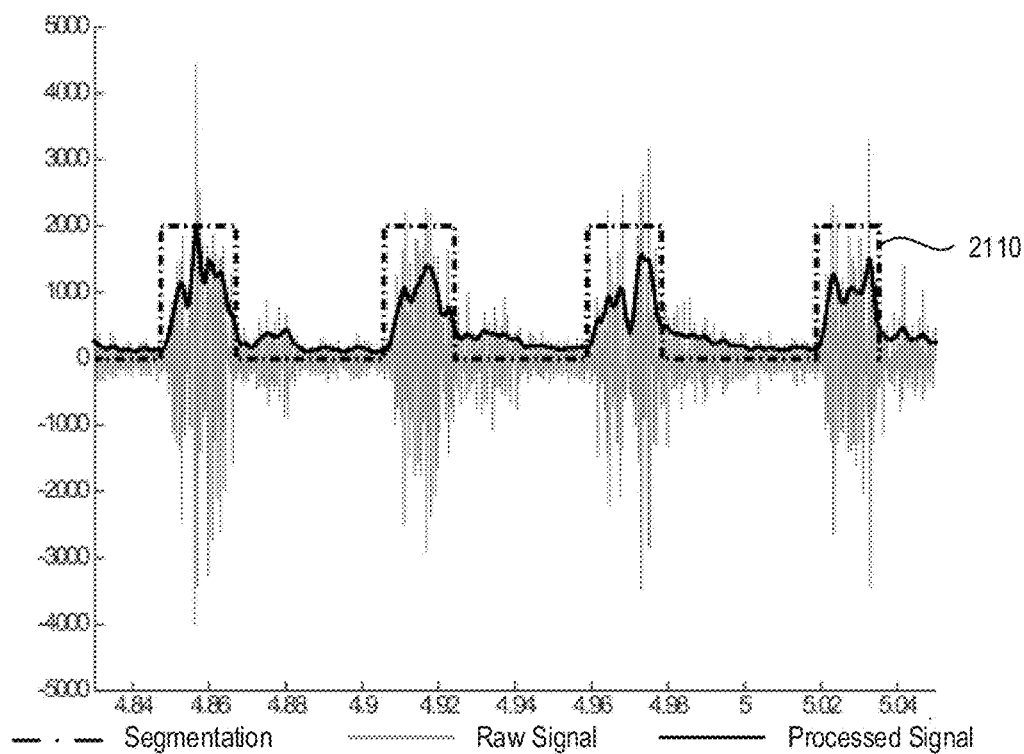
FIGS. 21A and 21B illustrate example signals prior to computing metrics and after discrimination has been performed as in the process of FIG. 18.
Figure 21B:
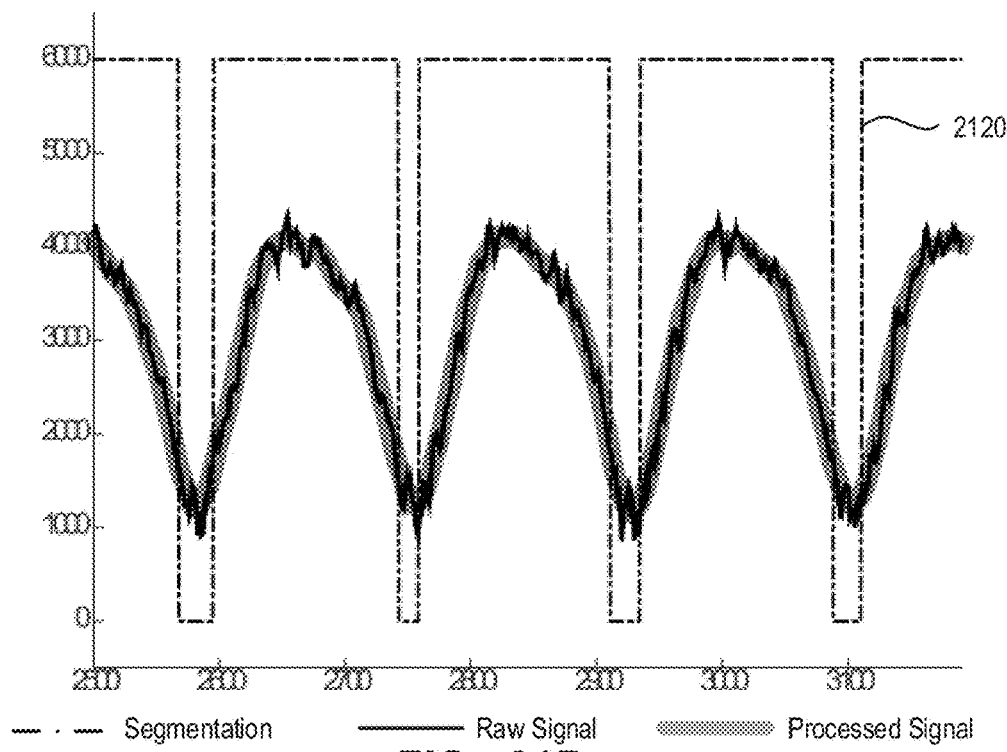

FIGS. 21A and 21B illustrate example EMG and accelerometer signals, respectively. Both FIGS. 21A and 21B illustrate raw signal waveforms, pre-processed signals, and segmented signals after discrimination has been performed using the feature-based approach. It can be appreciated that the discriminated signals 2110 and 2120 resemble discrete waveforms, with steep transitions that clearly delineate between "active" and "inactive" portions of the signal.

A second approach for signal segment discrimination employs an adaptive thresholding technique to perform the segmentation. The threshold may be calculated as the average of the maximum and minimum of the signal d in a window of size W, $$T(t) = \frac{\min(d(t-W:t)) + \max(d(t-W:t))}{2}$$

Accordingly, the width of each signal segment can be computed as:

$$Seg(t) = step(d(t) - T(t))$$

where Seg(t) is the segmentation result at time t, and step is the step function, which outputs a 0 value when its argument is less than or equal to 0, and outputs a 1 value when its argument is greater than 0. When Seg(t)=1 the signal portion at time t is considered "active" (e.g., relevant to the motion being performed). Conversely, when Seg(t)=0 the signal portion at time t is considered "inactive" (e.g., not relevant).

Figure 22A:
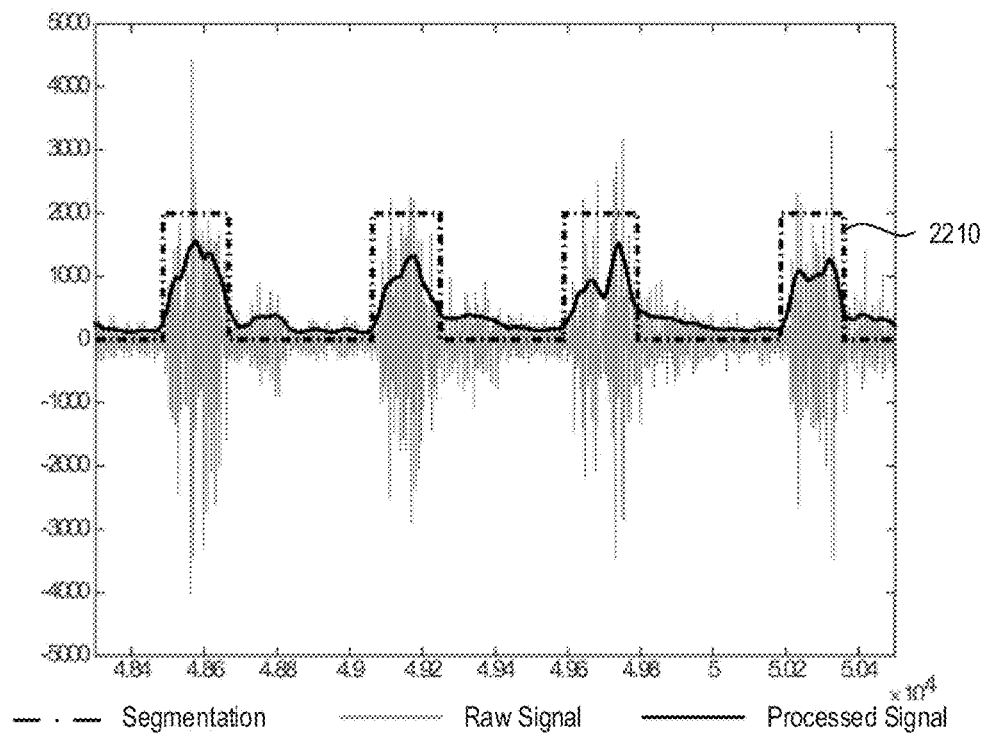
FIGS. 22A and 22B illustrate example signals prior to computing metrics and after discrimination has been performed as in the process of FIG. 19.
Figure 22B:
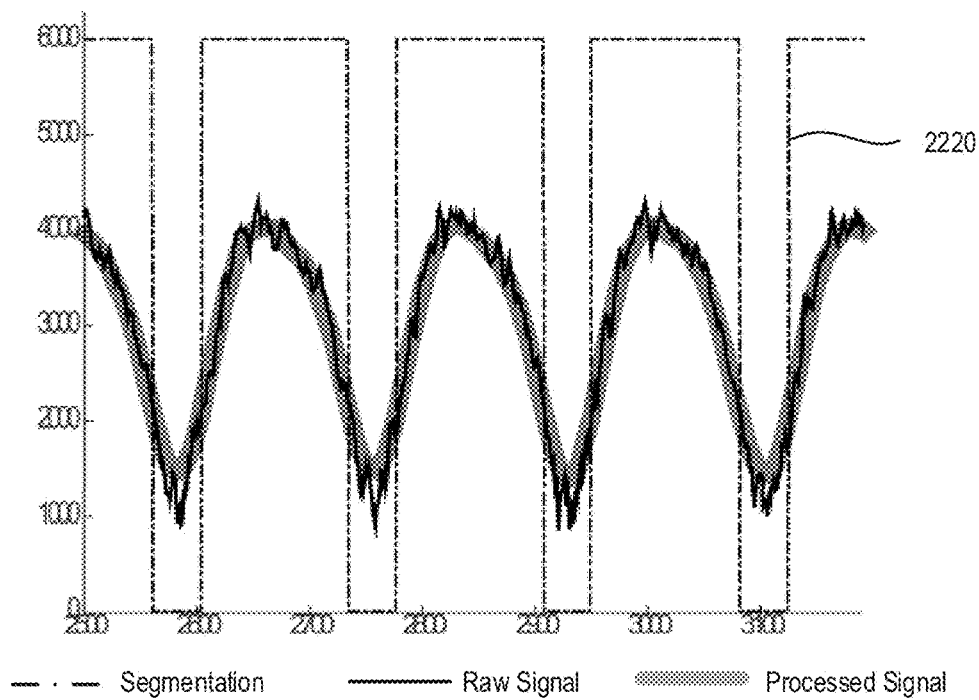

FIGS. 22A and 22B illustrate example EMG and accelerometer signals, respectively. Both FIGS. 22A and 22B illustrate raw signal waveforms, pre-processed signals, and segmented signals prior to computing metrics and after discrimination has been performed using the adaptive thresholding approach. It can be appreciated that the discriminated signals 2210 and 2220 resemble discrete waveforms, with steep transitions that clearly delineate between "active" and "inactive" portions of the signal.

Following signal segment discrimination, computation of at least one exercise metric based on the signal segments may be performed at 1750.

Various exercise metrics may be computed, which may use information from the plurality of signal segments, or from the plurality of pre-processed signals, or both. Likewise, the exercise metrics may be computed based on accelerometer data, EMG data or other sensor data, or some combination thereof.

Activity recognition can be carried out using acceleration or EMG signals, or both. Supervised modeling or classification algorithms can be trained to classify the actions being performed, as described herein with reference to FIGS. 10A to 11B.

Acceleration signals and EMG signals are time varying, which can result in temporal misalignments when computing exercise metrics. In such cases, time warping methods such as dynamic time warping (DTW) or its extensions, canonical time warping (CTW), generalized time warping (GTW), correlation optimized time warping (CoTW), or other methods can be used. These methods are optimization techniques that align (or temporally correlate) particular features or segments of data with respect to one another using warping. In some other embodiments, Kalman filters or other techniques can be used for fusing data.

Examples of exercise metrics that can be computed include cadence. An instantaneous cadence can be calculated in revolutions per minute (rpm), for cycling, or steps per minute (spm), for walking and running, by measuring the temporal distance between two consecutive signal segments in acceleration signals. Alternatively, velocity (integrated acceleration signal), or position (integrated velocity signal) can be used for computation. In some cases, where one muscle activation occurs per cycle, muscle activation segments can also be used to determine cadence. The temporal distance can be measured by comparing the beginnings of segments, middles of segments, ends of segments, or even the peaks within segments. Any axis showing periodic shapes, which can be correlated to steps or cycles, can be used. In one example, the velocity signal from an x-axis of the accelerometer can be used. Assuming $D(S_t)$ and $D(S_{t+1})$ are consecutive segments:

$$\text{cadence} = \frac{60}{F_s}(ind_{D(S_{t+1})} - ind_{D(S_t)})$$

where F is the sampling frequency, which can be set to 125 Hz, and $ind_{D(S_t)}$ and $ind_{D(S_{t+1})}$ are the time indices of the two segments.

Alternatively, other variations of cadence, for example revolutions per second, can be measured. Average cadence can be measured by averaging calculated cadence values over a certain time period, or by counting the number of revolutions/steps over that time.

Based on the placement of EMG sensors and, for example an activity type as determined using the described embodiments, the detected repetitions can be combined to illustrate a broad image of the user's activity. For example, consecutive contractions of the rectus femoris and hamstring muscles, in a cycling activity type, can denote that the measured repetitions to correspond to cycling repetitions. Conversely, if the activity type is running, the same measured repetitions may correspond to steps.

A speed, or velocity, can be calculated based the cadence metric in meters per second (m/s), kilometers per hour (km/h), miles per hour (mph), or other units. By estimating the approximate relationship between each step/cycle and traveled distance, speed can be calculated. For this metric, additional information such as gear ratio and wheel diameter (in case of cycling) or the person's height and average stride length (in case of walking and running) can be used to compute a more accurate measurement of speed.

A distance traveled can be calculated based on cadence, or a speed metric, by multiplying speeds and corresponding time intervals or number of cycles/steps by the approximate traveled distance per cycle/step.

A calorie expenditure can be approximated, based upon a user's weight, gender, height, speed, and traveled distance. Various formulas and coefficients may be used for this metric. For example, for male users, energy expenditure can be calculated using:

$$((-55.0969 + (0.6309 \times HR) + (0.1988 \times W) + (0.2017 \times A))/4.184) \times 60 \times T$$

and, for female users:

$$((-20.4022 + (0.4472 \times HR) - (0.1263 \times W) + (0.074 \times A))/4.184) \times 60 \times T$$

where HR is the heart rate (beats per minute), W is the weight (in kilograms), A is the age (in years), T is the exercise duration time (in hours).

When maximal oxygen consumption (VO2 max) is known, energy expenditure can optionally be calculated using, for male users:

$$((-95.7735 \times (0.634 \times HR) + (0.404 \times VO2\text{max}) + (0.394 \times W) + (0.271 \times A))/4.184) \times 60 \times T$$

and, for female users:

$$((-59.3954 + (0.45 \times HR) + (0.380 \times VO2\text{max}) + (0.103 \times W) + (0.274 \times A))/4.184) \times 60 \times T$$

A muscle activation intensity can be measured as the energy of an EMG signal (e.g., RMS) during each muscle activation/contraction (e.g., signal segment). The average intensity can be measured as the intensity over the length of the contraction or segment. Alternatively the total energy may be computed. A percentage value can be calculated by dividing intensity values by the user's maximum voluntary contraction (MVC), which can be calibrated at the beginning of an exercise (e.g., the user can be instructed to perform particular activities with maximum strength, which can be used as a reference to determine the amplitude of subsequent contractions of the muscles), or recalibrated during exercise based on a maximum excursion. Alternatively, the absolute value of the EMG samples can be used instead of the energy of the EMG. Muscle strength or power can be correlated with gross EMG amplitude, which can also be calibrated through a conventional cycling power meter.

A muscle coordination metric can be computed, based upon the time difference between activations of monitored muscles (e.g., for quadriceps and hamstring muscles). The timing difference can be measured in time units (e.g., seconds), percentage (e.g., by dividing the value by the time between muscle contractions, cadence, or a fixed reference timing), or degrees (by multiplying the percentage by $2\pi$ radians or 360°). This metric indicates how muscles of interest are being activated with respect to one another in terms of timing of contractions.

A muscle ratio may be computed as the percentage of the average activation intensity of muscle $M_1$ with respect to the total average activation intensities of muscles $M_1$ and $M_2$. For example, muscle ratio may be calculated as:

$$\text{quad}_{ratio} = \frac{I(D_{emg,quad})}{I(D_{emg,quad}) + I(D_{emg,ham})}$$

where I calculates the average or total energy of a given contraction. This metric can be used to determine the relative performance of muscles in terms of intensity of activation.

A muscle fatigue metric can be computed based on the shift in mean or median frequency of each muscle activation (e.g., for each signal segment). A shift may denote the onset of muscle fatigue. Standard power spectral density (PSD) analysis techniques such as fast Fourier transform (FFT) can be utilized for this purpose.

A muscle balance metric can be computed if two wearable devices are worn by the user (e.g., one on each leg), or if a single wearable device draws signals from opposing limbs. Corresponding contractions of corresponding muscles from left and right limbs can denote muscle balance.

A motion imbalance metric can be computed during activities such as walking, running, or cycling. In particular, lateral movement can be an indication of motion imbalance. Therefore, given accelerometer signals, the acceleration, velocity, or displacement along a particular axis (e.g., z-axis) can be interpreted as motion imbalance.

A muscle damage metric can be computed by analyzing muscle fiber activations, conduction velocities and firing rates. Values can be pre-stored when muscle tissue is healthy, and comparisons made over time. Alternatively particular spatiotemporal properties may be indicative of injury or damage.

A mechanical power metric can be computed by utilizing acceleration data and their processed derivations such as velocity and position, along with other information such as EMG signals, gear ratio and wheel diameter (for cycling) or stride length (for walking and running), slope of the ground, weight of the user, and other data if available.

A blood lactate metric can be computed by analyzing spatiotemporal properties of EMG signals.

In some embodiments, gestures and muscle activities may be monitored and used to control external devices. For example, gestures, rhythms, and amplitudes of muscle contractions may be used to control a variety of digital and physical devices such as music players, lighting and the like.

As described above, while EMG and accelerometer signals are described in the example embodiments, other types of data may be used to enhance accuracy. For example GNSS data may be used to verify or correct position signals.

Figure 18:
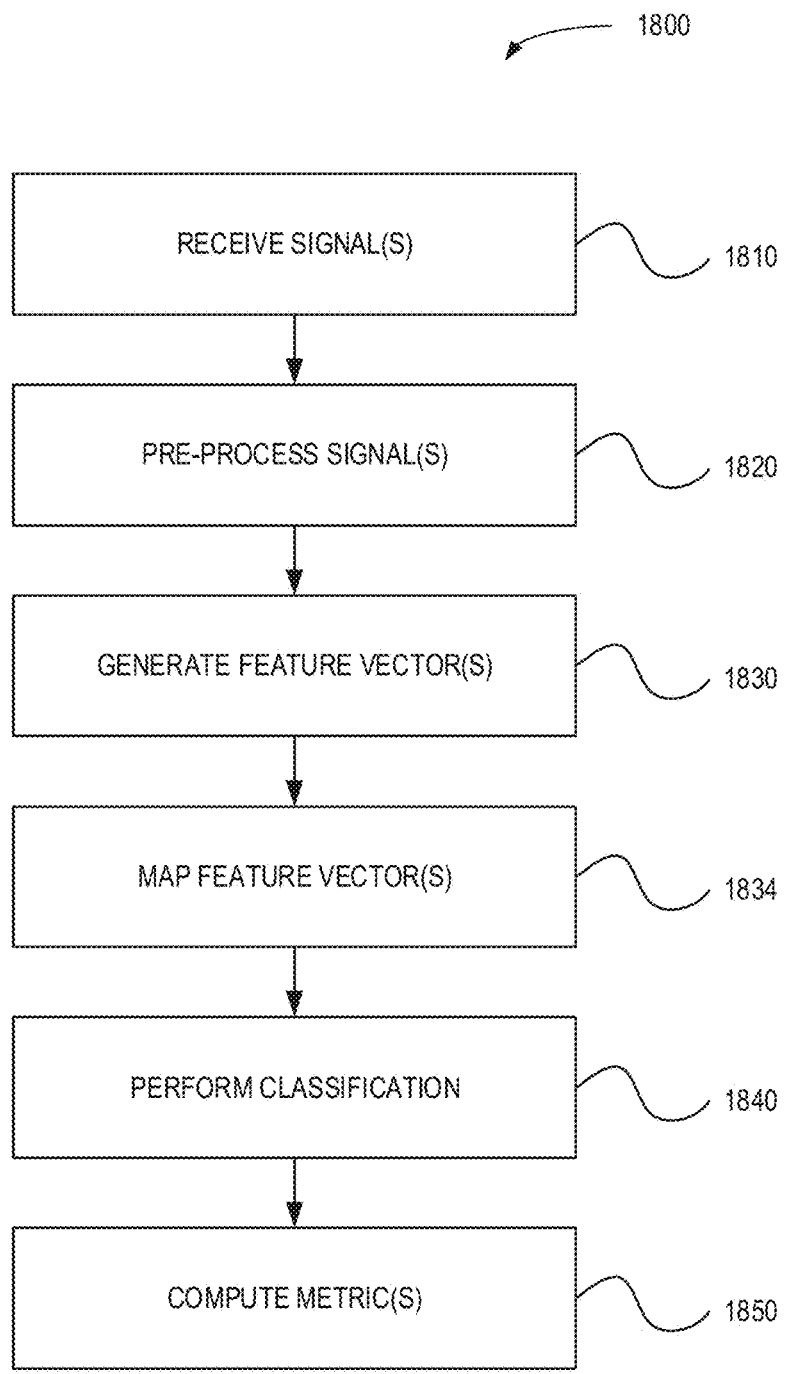
FIG. 18 illustrates another example process for computing exercise metrics using a wearable device.

Referring now to FIG. 18, there is illustrated an example process for analyzing activity of a user's body using a wearable device positioned on a user's limb. Process flow 1800 is an example embodiment of process flow 1700 and uses a feature-based discrimination approach. Process flow 1800 may be carried out using a wearable device as described herein.

Process flow begins at 1810 by receiving sensor signals, as at 1710 of flow 1700.

Next, at 1820, sensor signals may be processed to provide pre-processed signals, as at 1720 of flow 1700.

At 1830, feature vectors are generated from the filtered sensor signals. In some cases, feature vectors may be generated from raw sensor signals.

At 1834, feature vectors are mapped to the feature space identified during pre-training, e.g., using an ANOVA approach.

At 1840, a classifier is used to discriminate active and inactive signal portions and identify signal segments.

Finally, at 1850, one or more exercise metric may be computed, as at 1750 of flow 1700.

Figure 19:
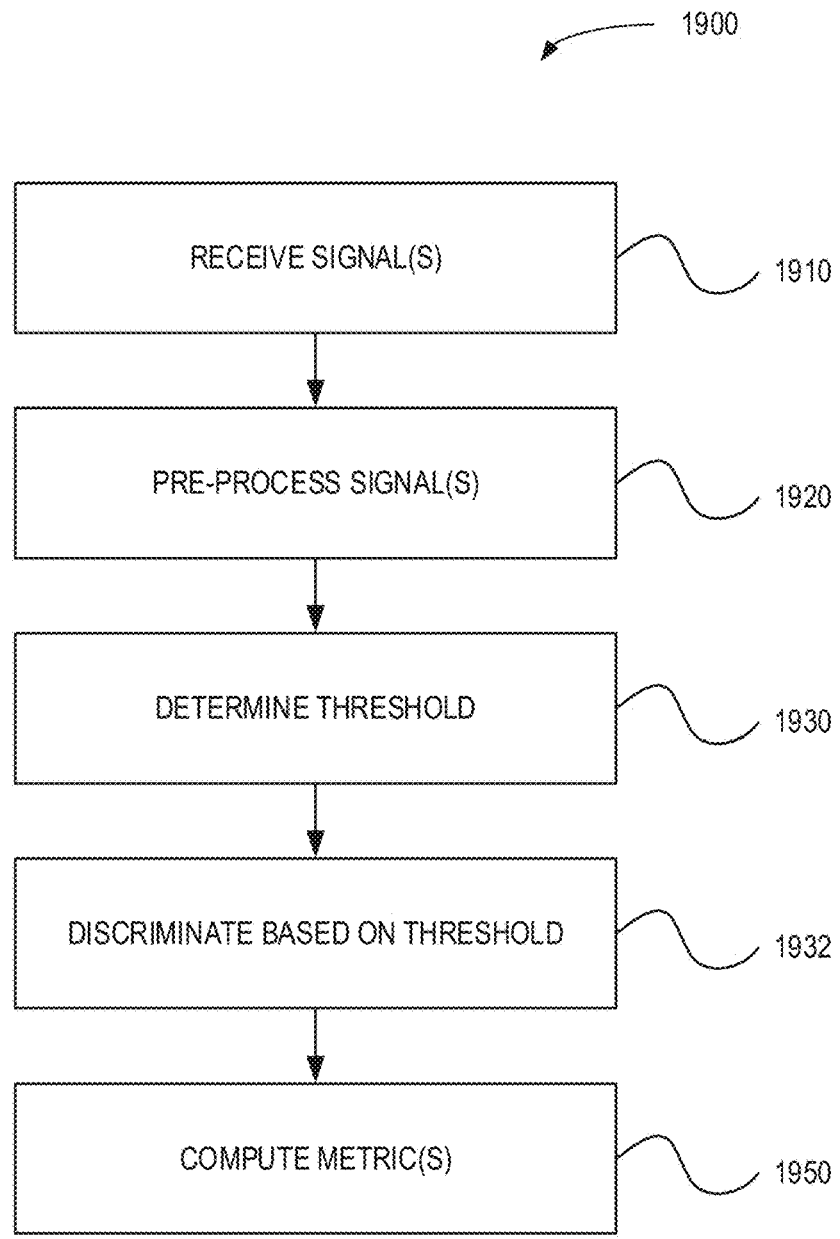
FIG. 19 illustrates another example process for computing exercise metrics using a wearable device.

Referring now to FIG. 19, there is illustrated an example process for analyzing activity of a user's body using a wearable device positioned on a user's limb. Process flow 1900 is an example embodiment of process flow 1700 and uses an adaptive threshold discrimination approach. Process flow 1900 may be carried out using a wearable device as described herein.

Process flow begins at 1910 by receiving sensor signals, as at 1710 of flow 1700.

Next, at 1920, sensor signals may be processed to provide pre-processed signals, as at 1720 of flow 1700.

At 1930, an adaptive threshold is generated from the filtered sensor signals as described herein. In some cases, the adaptive threshold may be generated from raw sensor signals. In still other cases, a fixed or predetermined threshold may be used. In general, spatiotemporal properties such as minimum, maximum, mean, median and their linear or non-linear functions may be used to determine the threshold.

At 1932, discrimination is performed to identify active and inactive signal portions and identify signal segments, based on portions of the signals that exceed the threshold.

Finally, at 1950, one or more exercise metric may be computed, as at 1750 of flow 1700.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A method of determining exercise metrics in real-time for a user's body using a wearable device, the method comprising:
receiving a plurality of signals from at least one sensor of the wearable device while the user is performing an exercise activity, wherein the at least one sensor comprises an accelerometer and a plurality of EMG sensors, and wherein the plurality of signals comprises acceleration signals and EMG signals;
pre-processing the plurality of signals to generate a plurality of pre-processed signals;
using a processor, discriminating the plurality of pre-processed signals to generate a plurality of signal segments for each of the plurality of pre-processed signals, wherein generating the plurality of signal segments comprises generating a plurality of feature vectors based on the plurality of pre-processed signals, wherein each feature vector comprises a plurality of feature values, and wherein each feature vector is associated with a time step of the pre-processed signals;

using the processor, temporally correlating a first plurality of signal segments from the plurality of signal segments, the first plurality of signal segments based on acceleration signals, with a second plurality of signal segments from the plurality of signal segments, the second plurality of signal segments based on EMG signals;

computing at least one exercise metric while the user is performing the exercise activity based on the first and second plurality of signal segments as temporally correlated; and outputting, via at least one of a display of the wearable device and a haptic feedback module of the wearable device, real-time feedback regarding the at least one exercise metric based on the computing.

2. The method of claim 1, wherein at least two of the EMG sensors are positioned to detect EMG signals from different muscles of the user.

3. The method of claim 2, wherein the at least one exercise metric comprises a muscle intensity metric.

4. The method of claim 2, wherein the at least one exercise metric comprises a muscle coordination metric.

5. The method of claim 2, wherein the at least one exercise metric comprises a muscle ratio metric.

6. The method of claim 2, wherein the at least one exercise metric comprises a muscle fatigue metric, and wherein the computing comprises computing a shift in a frequency characteristic of at least one EMG signal.

7. The method of claim 2, wherein generating the plurality of signal segments comprises determining a temporal distance between the plurality of signal segments.

8. The method of claim 1, wherein the at least one sensor comprises a sensor selected from the group consisting of a gyroscope and a magnetometer.

9. The method of claim 1, wherein each feature vector comprises time domain and frequency domain data based on the plurality of pre-processed signals.

10. The method of claim 1, wherein each feature vector is computed over a moving time window.

11. The method of claim 1, wherein generating the plurality of signal segments further comprises mapping the plurality of feature vectors onto a predetermined feature space.

12. The method of claim 11, wherein the mapping is predetermined by ANOVA computation over a training data set.

13. The method of claim 11, wherein the predetermined feature space is predetermined by Principal Component Analysis of a training data set.

14. The method of claim 1, wherein computing at least one exercise metric comprises performing, using the processor, hierarchical classification to compute a likeliest class for a current time step.

15. A wearable device for determining exercise metrics in real-time for a user's body, the wearable device comprising:
at least one sensor positionable on the user's limb;
an output module comprising at least one of a display and a haptic feedback module; and
a processor operatively coupled to the at least one sensor and the output module, the processor configured to:

receive a plurality of signals from at least one sensor of the wearable device while the user is performing an exercise activity;

pre-process the plurality of signals to generate a plurality of pre-processed signals;

discriminate the plurality of pre-processed signals to generate a plurality of signal segments for each of the plurality of pre-processed signals, wherein generating the plurality of signal segments comprises generating a plurality of feature vectors based on the plurality of pre-processed signals, wherein each feature vector comprises a plurality of feature values, and wherein each feature vector is associated with a time step of the pre-processed signals;

temporally correlate a first plurality of signal segments from the plurality of signal segments, the first plurality of signal segments based on acceleration signals, with a second plurality of signal segments from the plurality of signal segments, the second plurality of signal segments based on EMG signals;

compute at least one exercise metric while the user is performing the exercise activity based on the first and second plurality of signal segments as temporally correlated;

output, via the output module, real-time feedback regarding the at least one exercise metric based on the computing.

16. A non-transitory computer readable medium storing computer-executable instructions, which, when executed by a computer processor, cause the computer processor to carry out a method of determining exercise metrics in real-time for a user's body using a wearable device, the method comprising:

receiving a plurality of signals from at least one sensor of the wearable device while the user is performing an exercise activity;

pre-processing the plurality of signals to generate a plurality of pre-processed signals;

discriminating the plurality of pre-processed signals to generate a plurality of signal segments for each of the plurality of pre-processed signals, wherein generating the plurality of signal segments comprises generating a plurality of feature vectors based on the plurality of pre-processed signals, wherein each feature vector comprises a plurality of feature values, and wherein each feature vector is associated with a time step of the pre-processed signals;

temporally correlating a first plurality of signal segments from the plurality of signal segments, the first plurality of signal segments based on acceleration signals, with a second plurality of signal segments from the plurality of signal segments, the second plurality of signal segments based on EMG signals;

computing at least one exercise metric while the user is performing the exercise activity based on the first and second plurality of signal segments as temporally correlated; and outputting, via at least one of a display of the wearable device and a haptic feedback module of the wearable device, real-time feedback regarding the at least one exercise metric based on the computing.

* * * * *